US009550811B2

(12) United States Patent
Lange et al.

(10) Patent No.: US 9,550,811 B2
(45) Date of Patent: Jan. 24, 2017

(54) PEPTIDE SCAFFOLD DESIGN

(75) Inventors: Einar Tønnes Lange, Skien (NO); Maja Sommerfelt Grønvold, Risør (NO); Jens Olof Holmberg, Helsingborg (SE); Birger Sørensen, Skien (NO)

(73) Assignee: BIONOR IMMUNO AS, Skien (NO)

( * ) Notice: Subject to any disclaimer, the term of this patent is extended or adjusted under 35 U.S.C. 154(b) by 183 days.

(21) Appl. No.: 13/991,108

(22) PCT Filed: Dec. 2, 2011

(86) PCT No.: PCT/DK2011/050460
§ 371 (c)(1),
(2), (4) Date: Aug. 26, 2013

(87) PCT Pub. No.: WO2012/072088
PCT Pub. Date: Jun. 7, 2012

(65) Prior Publication Data

US 2013/0337002 A1 Dec. 19, 2013

Related U.S. Application Data

(60) Provisional application No. 61/475,965, filed on Apr. 15, 2011.

(30) Foreign Application Priority Data

Dec. 2, 2010 (EP) .................................... 10193479

(51) Int. Cl.

| | |
|---|---|
| ***A61K 48/00*** | (2006.01) |
| ***A61K 9/127*** | (2006.01) |
| ***C12N 15/85*** | (2006.01) |
| ***C12P 21/00*** | (2006.01) |
| ***A61K 31/7115*** | (2006.01) |
| ***C07K 14/005*** | (2006.01) |
| ***A61K 39/12*** | (2006.01) |
| ***A61K 39/145*** | (2006.01) |
| ***A61K 39/21*** | (2006.01) |
| ***A61K 39/29*** | (2006.01) |
| ***C07K 7/08*** | (2006.01) |
| *C12N 15/87* | (2006.01) |
| *A61K 39/00* | (2006.01) |

(52) U.S. Cl.
CPC ............. *C07K 14/005* (2013.01); *A61K 39/12* (2013.01); *A61K 39/145* (2013.01); *A61K 39/21* (2013.01); *A61K 39/29* (2013.01); *C07K 7/08* (2013.01); *A61K 39/00* (2013.01); *A61K 48/005* (2013.01); *A61K 48/0033* (2013.01); *A61K 48/0066* (2013.01); *C12N 15/87* (2013.01); *C12N 2710/16122* (2013.01); *C12N 2710/16134* (2013.01); *C12N 2710/20022* (2013.01); *C12N 2710/20034* (2013.01); *C12N 2740/16222* (2013.01); *C12N 2740/16234* (2013.01); *C12N 2760/16122* (2013.01); *C12N 2760/16134* (2013.01); *C12N 2770/24222* (2013.01); *C12N 2770/24234* (2013.01)

(58) Field of Classification Search
CPC ... C07K 14/005; C12N 15/87; A61K 48/0066; A61K 48/0033; A61K 48/005
USPC .......................................................... 424/189
See application file for complete search history.

(56) References Cited

U.S. PATENT DOCUMENTS

| | | | |
|---|---|---|---|
| 6,592,871 | B1 | 7/2003 | Seidel et al. |
| 7,393,831 | B2 | 7/2008 | Fournillier et al. |
| 8,242,084 | B2 | 8/2012 | Sugiyama et al. |
| 2009/0104216 | A1 | 4/2009 | Torres |
| 2010/0183647 | A1 | 7/2010 | Khanna et al. |

FOREIGN PATENT DOCUMENTS

| | | | |
|---|---|---|---|
| CN | 101412747 | A | 4/2009 |
| CN | 101851275 | A | 10/2010 |
| EP | 0923940 | A1 | 6/1999 |
| WO | WO 00/52040 | A1 | 9/2000 |
| WO | WO0052040 | * | 9/2000 |
| WO | WO 01/10456 | A2 | 2/2001 |
| WO | WO 02/090382 | A2 | 11/2002 |
| WO | WO 2004/063217 | A1 | 7/2004 |
| WO | WO 2005/099752 | A2 | 10/2005 |
| WO | WO 2008/107400 | A1 | 9/2008 |
| WO | WO2008107400 | * | 9/2008 |
| WO | WO 2009/002159 | A2 | 12/2008 |
| WO | WO 2009/012143 | A2 | 1/2009 |
| WO | WO 2009/027688 | A1 | 3/2009 |
| WO | WO 2010/056808 | A2 | 5/2010 |

(Continued)

OTHER PUBLICATIONS

Dakappagari, N. K., et al., "Intracellular delivery of a novel multiepitope peptide vaccine by an amphipathic peptide carrier enhances cytotoxic T-cell responses in IILA-A*201 mice", *Journal of Peptide Research*, Feb. 1, 2005, pp. 189-199, vol. 65, No. 2, Blackwell Publishing Ltd, Oxford; GB.

(Continued)

*Primary Examiner* — Janet L Andres
*Assistant Examiner* — Barry A Chestnut
(74) *Attorney, Agent, or Firm* — Womble Carlyle Sandridge & Rice LLP

(57) ABSTRACT

The present invention relates to novel peptides and methods for treatment, diagnosis and prognosis of virus infections including infections with HCV, HIV, CMV and Influenza. The invention further relates to methods for identifying and providing peptides useful for the treatment and diagnosis.

$$X^1\text{-}X^2\text{-}X^3\text{-}X^4\text{-}X^5 \quad (I)$$

16 Claims, No Drawings

(56) References Cited

FOREIGN PATENT DOCUMENTS

WO WO 2010/081095 A2 7/2010

OTHER PUBLICATIONS

Dakappagari, N., et al., "Elicitation of Polyclonal Cytotoxic T-Responses to HER-2 in HLA-A0201 Mice by a Novel Multiepitope Peptide Vaccine", *Biopolymers*, Jul. 23, 2003, 1 page (abstract), vol. 71, No. 3, John Wiley & Sons, Inc., US.

European Patent Office, Extended European Search Report for Application No. 11844256.5, Nov. 4, 2014, 7 pages, Germany.

Sundaram, R., et al., "A novel multivalent human CTL peptide construct elicits robust cellular immune responses in HLA-A*0201 transgenic mice: implications for HTLV-1 vaccine design", *Vaccine*, Jun. 20, 2003, pp. 2767-2781, vol. 21, No. 21-22, Elsevier Ltd, GB.

Assarsson, E., et al., "Immunomic Analysis of the Repertoire of T-Cell Specificities for Influenza A Virus in Humans," *Journal of Virology*, 2008 vol. 82(24), pp. 12241-12251.

Chen, H., et al., "Identification of HLA-A11-restricted CTL epitopes derived from HPV type 18 using DNA immunization," *Cancer Biology & Therapy*, 2009, vol. 8(21), pp. 2025-2032.

Khan, N., et al., "T Cell Recognition Patterns of Immunodominant Cytomegalovirus Antigens in Primary and Persistent Infection," *The Journal of Immunology*, 2007, vol. 178, pp. 4455-4465.

* cited by examiner

SEQUENCE LISTING

```
<160> NUMBER OF SEQ ID NOS: 199

<210> SEQ ID NO 1
<211> LENGTH: 3011
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
```

-continued

```
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495
```

-continued

```
Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910
```

-continued

```
Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                 1005

Glu Ile  Leu Leu Gly Pro Ala  Asp Gly Met Val Ser  Lys Gly Trp
    1010                 1015                 1020

Arg Leu  Leu Ala Pro Ile Thr  Ala Tyr Ala Gln Gln  Thr Arg Gly
    1025                 1030                 1035

Leu Leu  Gly Cys Ile Ile Thr  Ser Leu Thr Gly Arg  Asp Lys Asn
    1040                 1045                 1050

Gln Val  Glu Gly Glu Val Gln  Ile Val Ser Thr Ala  Thr Gln Thr
    1055                 1060                 1065

Phe Leu  Ala Thr Cys Ile Asn  Gly Val Cys Trp Thr  Val Tyr His
    1070                 1075                 1080

Gly Ala  Gly Thr Arg Thr Ile  Ala Ser Pro Lys Gly  Pro Val Ile
    1085                 1090                 1095

Gln Met  Tyr Thr Asn Val Asp  Gln Asp Leu Val Gly  Trp Pro Ala
    1100                 1105                 1110

Pro Gln  Gly Ser Arg Ser Leu  Thr Pro Cys Thr Cys  Gly Ser Ser
    1115                 1120                 1125

Asp Leu  Tyr Leu Val Thr Arg  His Ala Asp Val Ile  Pro Val Arg
    1130                 1135                 1140

Arg Arg  Gly Asp Ser Arg Gly  Ser Leu Leu Ser Pro  Arg Pro Ile
    1145                 1150                 1155

Ser Tyr  Leu Lys Gly Ser Ser  Gly Gly Pro Leu Leu  Cys Pro Ala
    1160                 1165                 1170

Gly His  Ala Val Gly Leu Phe  Arg Ala Ala Val Cys  Thr Arg Gly
    1175                 1180                 1185

Val Ala  Lys Ala Val Asp Phe  Ile Pro Val Glu Asn  Leu Glu Thr
    1190                 1195                 1200

Thr Met  Arg Ser Pro Val Phe  Thr Asp Asn Ser Ser  Pro Pro Ala
    1205                 1210                 1215

Val Pro  Gln Ser Phe Gln Val  Ala His Leu His Ala  Pro Thr Gly
    1220                 1225                 1230

Ser Gly  Lys Ser Thr Lys Val  Pro Ala Ala Tyr Ala  Ala Gln Gly
    1235                 1240                 1245

Tyr Lys  Val Leu Val Leu Asn  Pro Ser Val Ala Ala  Thr Leu Gly
    1250                 1255                 1260

Phe Gly  Ala Tyr Met Ser Lys  Ala His Gly Val Asp  Pro Asn Ile
    1265                 1270                 1275

Arg Thr  Gly Val Arg Thr Ile  Thr Thr Gly Ser Pro  Ile Thr Tyr
    1280                 1285                 1290

Ser Thr  Tyr Gly Lys Phe Leu  Ala Asp Gly Gly Cys  Ser Gly Gly
    1295                 1300                 1305

Ala Tyr  Asp Ile Ile Ile Cys  Asp Glu Cys His Ser  Thr Asp Ala
```

-continued

```
    1310                1315                1320

Thr Ser  Ile Leu Gly Ile Gly  Thr Val Leu Asp Gln  Ala Glu Thr
    1325                1330                1335

Ala Gly  Ala Arg Leu Val Val  Leu Ala Thr Ala Thr  Pro Pro Gly
    1340                1345                1350

Ser Val  Thr Val Ser His Pro  Asn Ile Glu Glu Val  Ala Leu Ser
    1355                1360                1365

Thr Thr  Gly Glu Ile Pro Phe  Tyr Gly Lys Ala Ile  Pro Leu Glu
    1370                1375                1380

Val Ile  Lys Gly Gly Arg His  Leu Ile Phe Cys His  Ser Lys Lys
    1385                1390                1395

Lys Cys  Asp Glu Leu Ala Ala  Lys Leu Val Ala Leu  Gly Ile Asn
    1400                1405                1410

Ala Val  Ala Tyr Tyr Arg Gly  Leu Asp Val Ser Val  Ile Pro Thr
    1415                1420                1425

Ser Gly  Asp Val Val Val Val  Ser Thr Asp Ala Leu  Met Thr Gly
    1430                1435                1440

Phe Thr  Gly Asp Phe Asp Ser  Val Ile Asp Cys Asn  Thr Cys Val
    1445                1450                1455

Thr Gln  Thr Val Asp Phe Ser  Leu Asp Pro Thr Phe  Thr Ile Glu
    1460                1465                1470

Thr Thr  Thr Leu Pro Gln Asp  Ala Val Ser Arg Thr  Gln Arg Arg
    1475                1480                1485

Gly Arg  Thr Gly Arg Gly Lys  Pro Gly Ile Tyr Arg  Phe Val Ala
    1490                1495                1500

Pro Gly  Glu Arg Pro Ser Gly  Met Phe Asp Ser Ser  Val Leu Cys
    1505                1510                1515

Glu Cys  Tyr Asp Ala Gly Cys  Ala Trp Tyr Glu Leu  Thr Pro Ala
    1520                1525                1530

Glu Thr  Thr Val Arg Leu Arg  Ala Tyr Met Asn Thr  Pro Gly Leu
    1535                1540                1545

Pro Val  Cys Gln Asp His Leu  Glu Phe Trp Glu Gly  Val Phe Thr
    1550                1555                1560

Gly Leu  Thr His Ile Asp Ala  His Phe Leu Ser Gln  Thr Lys Gln
    1565                1570                1575

Ser Gly  Glu Asn Phe Pro Tyr  Leu Val Ala Tyr Gln  Ala Thr Val
    1580                1585                1590

Cys Ala  Arg Ala Gln Ala Pro  Pro Pro Ser Trp Asp  Gln Met Trp
    1595                1600                1605

Lys Cys  Leu Ile Arg Leu Lys  Pro Thr Leu His Gly  Pro Thr Pro
    1610                1615                1620

Leu Leu  Tyr Arg Leu Gly Ala  Val Gln Asn Glu Val  Thr Leu Thr
    1625                1630                1635

His Pro  Ile Thr Lys Tyr Ile  Met Thr Cys Met Ser  Ala Asp Leu
    1640                1645                1650

Glu Val  Val Thr Ser Thr Trp  Val Leu Val Gly Gly  Val Leu Ala
    1655                1660                1665

Ala Leu  Ala Ala Tyr Cys Leu  Ser Thr Gly Cys Val  Val Ile Val
    1670                1675                1680

Gly Arg  Ile Val Leu Ser Gly  Lys Pro Ala Ile Ile  Pro Asp Arg
    1685                1690                1695

Glu Val  Leu Tyr Gln Glu Phe  Asp Glu Met Glu Glu  Cys Ser Gln
    1700                1705                1710
```

```
His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala
    1730                1735                1740

Glu Val Ile Thr Pro Ala Val Gln Thr Asn Trp Gln Lys Leu Glu
    1745                1750                1755

Val Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ala Val Thr Ser Pro Leu Thr Thr
    1790                1795                1800

Gly Gln Thr Leu Leu Phe Asn Ile Leu Gly Gly Trp Val Ala Ala
    1805                1810                1815

Gln Leu Ala Ala Pro Gly Ala Ala Thr Ala Phe Val Gly Ala Gly
    1820                1825                1830

Leu Ala Gly Ala Ala Ile Gly Ser Val Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Val Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp
    1970                1975                1980

Ile Cys Glu Val Leu Ser Asp Phe Lys Thr Trp Leu Lys Ala Lys
    1985                1990                1995

Leu Met Pro Gln Leu Pro Gly Ile Pro Phe Val Ser Cys Gln Arg
    2000                2005                2010

Gly Tyr Arg Gly Val Trp Arg Gly Asp Gly Ile Met His Thr Arg
    2015                2020                2025

Cys His Cys Gly Ala Glu Ile Thr Gly His Val Lys Asn Gly Thr
    2030                2035                2040

Met Arg Ile Val Gly Pro Arg Thr Cys Arg Asn Met Trp Ser Gly
    2045                2050                2055

Thr Phe Pro Ile Asn Ala Tyr Thr Thr Gly Pro Cys Thr Pro Leu
    2060                2065                2070

Pro Ala Pro Asn Tyr Lys Phe Ala Leu Trp Arg Val Ser Ala Glu
    2075                2080                2085

Glu Tyr Val Glu Ile Arg Arg Val Gly Asp Phe His Tyr Val Ser
    2090                2095                2100
```

-continued

```
Gly Met  Thr Thr Asp Asn Leu  Lys Cys Pro Cys Gln  Ile Pro Ser
    2105                 2110                 2115

Pro Glu  Phe Phe Thr Glu Leu  Asp Gly Val Arg Leu  His Arg Phe
    2120                 2125                 2130

Ala Pro  Pro Cys Lys Pro Leu  Leu Arg Glu Glu Val  Ser Phe Arg
    2135                 2140                 2145

Val Gly  Leu His Glu Tyr Pro  Val Gly Ser Gln Leu  Pro Cys Glu
    2150                 2155                 2160

Pro Glu  Pro Asp Val Ala Val  Leu Thr Ser Met Leu  Thr Asp Pro
    2165                 2170                 2175

Ser His  Ile Thr Ala Glu Ala  Ala Gly Arg Arg Leu  Ala Arg Gly
    2180                 2185                 2190

Ser Pro  Pro Ser Met Ala Ser  Ser Ser Ala Ser Gln  Leu Ser Ala
    2195                 2200                 2205

Pro Ser  Leu Lys Ala Thr Cys  Thr Ala Asn His Asp  Ser Pro Asp
    2210                 2215                 2220

Ala Glu  Leu Ile Glu Ala Asn  Leu Leu Trp Arg Gln  Glu Met Gly
    2225                 2230                 2235

Gly Asn  Ile Thr Arg Val Glu  Ser Glu Asn Lys Val  Val Ile Leu
    2240                 2245                 2250

Asp Ser  Phe Asp Pro Leu Val  Ala Glu Glu Asp Glu  Arg Glu Val
    2255                 2260                 2265

Ser Val  Pro Ala Glu Ile Leu  Arg Lys Ser Arg Arg  Phe Ala Arg
    2270                 2275                 2280

Ala Leu  Pro Val Trp Ala Arg  Pro Asp Tyr Asn Pro  Pro Leu Val
    2285                 2290                 2295

Glu Thr  Trp Lys Lys Pro Asp  Tyr Glu Pro Pro Val  Val His Gly
    2300                 2305                 2310

Cys Pro  Leu Pro Pro Pro Arg  Ser Pro Pro Val Pro  Pro Pro Arg
    2315                 2320                 2325

Lys Lys  Arg Thr Val Val Leu  Thr Glu Ser Thr Leu  Ser Thr Ala
    2330                 2335                 2340

Leu Ala  Glu Leu Ala Thr Lys  Ser Phe Gly Ser Ser  Ser Thr Ser
    2345                 2350                 2355

Gly Ile  Thr Gly Asp Asn Thr  Thr Thr Ser Ser Glu  Pro Ala Pro
    2360                 2365                 2370

Ser Gly  Cys Pro Pro Asp Ser  Asp Val Glu Ser Tyr  Ser Ser Met
    2375                 2380                 2385

Pro Pro  Leu Glu Gly Glu Pro  Gly Asp Pro Asp Leu  Ser Asp Gly
    2390                 2395                 2400

Ser Trp  Ser Thr Val Ser Ser  Gly Ala Asp Thr Glu  Asp Val Val
    2405                 2410                 2415

Cys Cys  Ser Met Ser Tyr Ser  Trp Thr Gly Ala Leu  Val Thr Pro
    2420                 2425                 2430

Cys Ala  Ala Glu Glu Gln Lys  Leu Pro Ile Asn Ala  Leu Ser Asn
    2435                 2440                 2445

Ser Leu  Leu Arg His His Asn  Leu Val Tyr Ser Thr  Thr Ser Arg
    2450                 2455                 2460

Ser Ala  Cys Gln Arg Gln Lys  Lys Val Thr Phe Asp  Arg Leu Gln
    2465                 2470                 2475

Val Leu  Asp Ser His Tyr Gln  Asp Val Leu Lys Glu  Val Lys Ala
    2480                 2485                 2490

Ala Ala  Ser Lys Val Lys Ala  Asn Leu Leu Ser Val  Glu Glu Ala
```

```
    2495                2500                2505

Cys Ser Leu Thr Pro Pro His Ser Ala Lys Ser Lys Phe Gly Tyr
    2510                2515                2520

Gly Ala Lys Asp Val Arg Cys His Ala Arg Lys Ala Val Ala His
    2525                2530                2535

Ile Asn Ser Val Trp Lys Asp Leu Leu Glu Asp Ser Val Thr Pro
    2540                2545                2550

Ile Asp Thr Thr Ile Met Ala Lys Asn Glu Val Phe Cys Val Gln
    2555                2560                2565

Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Ser Lys Leu Pro Leu Ala Val Met Gly Ser Ser Tyr Gly Phe
    2600                2605                2610

Gln Tyr Ser Pro Gly Gln Arg Val Glu Phe Leu Val Gln Ala Trp
    2615                2620                2625

Lys Ser Lys Lys Thr Pro Met Gly Phe Ser Tyr Asp Thr Arg Cys
    2630                2635                2640

Phe Asp Ser Thr Val Thr Glu Ser Asp Ile Arg Thr Glu Glu Ala
    2645                2650                2655

Ile Tyr Gln Cys Cys Asp Leu Asp Pro Gln Ala Arg Val Ala Ile
    2660                2665                2670

Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
    2735                2740                2745

Val Gln Glu Asp Ala Ala Ser Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asn Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895
```

```
Pro Gly  Glu Ile Asn Arg Val  Ala Ala Cys Leu Arg  Lys Leu Gly
    2900                2905                2910

Val Pro  Pro Leu Arg Ala Trp  Arg His Arg Ala Arg  Ser Val Arg
    2915                2920                2925

Ala Arg  Leu Leu Ser Arg Gly  Gly Arg Ala Ala Ile  Cys Gly Lys
    2930                2935                2940

Tyr Leu  Phe Asn Trp Ala Val  Arg Thr Lys Leu Lys  Leu Thr Pro
    2945                2950                2955

Ile Ala  Ala Ala Gly Arg Leu  Asp Leu Ser Gly Trp  Phe Thr Ala
    2960                2965                2970

Gly Tyr  Ser Gly Gly Asp Ile  Tyr His Ser Val Ser  His Ala Arg
    2975                2980                2985

Pro Arg  Trp Phe Trp Phe Cys  Leu Leu Leu Leu Ala  Ala Gly Val
    2990                2995                3000

Gly Ile  Tyr Leu Leu Pro Asn  Arg
    3005                3010


<210> SEQ ID NO 2
<211> LENGTH: 191
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190


<210> SEQ ID NO 3
<211> LENGTH: 3010
<212> TYPE: PRT
<213> ORGANISM: Hepatitis C virus

<400> SEQUENCE: 3

Met Ser Thr Asn Pro Lys Pro Gln Arg Lys Thr Lys Arg Asn Thr Asn
1               5                   10                  15
```

-continued

```
Arg Arg Pro Gln Asp Ile Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Val Ser Ala Tyr
            180                 185                 190

Glu Val Arg Asn Ala Ser Gly Met Tyr His Val Thr Asn Asp Cys Ser
        195                 200                 205

Asn Ser Ser Ile Val Tyr Glu Ala Ala Asp Met Ile Met His Thr Pro
    210                 215                 220

Gly Cys Val Pro Cys Val Arg Glu Asp Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Leu Arg Arg His Val Asp Leu Leu Val Gly Val Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly Arg Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Thr Gly Ser His
            340                 345                 350

Trp Gly Ile Leu Ala Gly Leu Ala Tyr Tyr Ser Met Val Gly Asn Trp
        355                 360                 365

Ala Lys Val Leu Ile Ala Met Leu Leu Phe Ala Gly Val Asp Gly Thr
    370                 375                 380

Thr His Val Thr Gly Gly Ala Gln Gly Arg Ala Ala Ser Ser Leu Thr
385                 390                 395                 400

Ser Leu Phe Ser Pro Gly Pro Val Gln His Leu Gln Leu Ile Asn Thr
                405                 410                 415

Asn Gly Ser Trp His Ile Asn Arg Thr Ala Leu Ser Cys Asn Asp Ser
            420                 425                 430
```

-continued

```
Leu Asn Thr Gly Phe Val Ala Ala Leu Phe Tyr Lys Tyr Arg Phe Asn
        435                 440                 445

Ala Ser Gly Cys Pro Glu Arg Leu Ala Thr Cys Arg Pro Ile Asp Thr
    450                 455                 460

Phe Ala Gln Gly Trp Gly Pro Ile Thr Tyr Thr Glu Pro His Asp Leu
465                 470                 475                 480

Asp Gln Arg Pro Tyr Cys Trp His Tyr Ala Pro Gln Pro Cys Gly Ile
                485                 490                 495

Val Pro Thr Leu Gln Val Cys Gly Pro Val Tyr Cys Phe Thr Pro Ser
            500                 505                 510

Pro Val Ala Val Gly Thr Thr Asp Arg Phe Gly Ala Pro Thr Tyr Arg
        515                 520                 525

Trp Gly Ala Asn Glu Thr Asp Val Leu Leu Leu Asn Asn Ala Gly Pro
    530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Gly Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Gly Ala Glu His Arg Leu
625                 630                 635                 640

Asp Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Ile Gln Tyr Leu Tyr Gly
    690                 695                 700

Ile Gly Ser Ala Val Val Ser Phe Ala Ile Lys Trp Glu Tyr Ile Val
705                 710                 715                 720

Leu Leu Phe Leu Leu Leu Ala Asp Ala Arg Val Cys Ala Cys Leu Trp
                725                 730                 735

Met Met Leu Leu Val Ala Gln Ala Glu Ala Ala Leu Glu Asn Leu Val
            740                 745                 750

Val Leu Asn Ala Ala Ser Val Ala Gly Ala His Gly Ile Leu Ser Phe
        755                 760                 765

Ile Val Phe Phe Cys Ala Ala Trp Tyr Ile Lys Gly Arg Leu Val Pro
    770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830

Pro His Tyr Lys Val Phe Leu Ala Arg Phe Ile Trp Trp Leu Gln Tyr
        835                 840                 845

Leu Ile Thr Arg Thr Glu Ala His Leu Gln Val Trp Val Pro Pro Leu
```

```
    850                 855                 860

Asn Val Arg Gly Gly Arg Asp Ala Ile Ile Leu Leu Thr Cys Val Val
865                 870                 875                 880

His Pro Glu Leu Ile Phe Asp Ile Thr Lys Tyr Leu Leu Ala Ile Phe
                885                 890                 895

Gly Pro Leu Met Val Leu Gln Ala Gly Ile Thr Arg Val Pro Tyr Phe
            900                 905                 910

Val Arg Ala Gln Gly Leu Ile Arg Ala Cys Met Leu Ala Arg Lys Val
        915                 920                 925

Val Gly Gly His Tyr Val Gln Met Val Phe Met Lys Leu Ala Ala Leu
    930                 935                 940

Ala Gly Thr Tyr Val Tyr Asp His Leu Thr Pro Leu Arg Asp Trp Ala
945                 950                 955                 960

His Thr Gly Leu Arg Asp Leu Ala Val Ala Val Glu Pro Val Val Phe
                965                 970                 975

Ser Asp Met Glu Thr Lys Val Ile Thr Trp Gly Ala Asp Thr Ala Ala
            980                 985                 990

Cys Gly Asp Ile Ile Leu Ala Leu  Pro Ala Ser Ala Arg  Arg Gly Lys
        995                 1000                1005

Glu Ile  Leu Leu Gly Pro Ala  Asp Ser Leu Glu Gly  Gln Gly Trp
    1010                 1015                 1020

Arg Leu  Leu Ala Pro Ile Thr  Ala Tyr Ser Gln Gln  Thr Arg Gly
    1025                 1030                 1035

Leu Leu  Gly Cys Ile Ile Thr  Ser Leu Thr Gly Arg  Asp Lys Asn
    1040                 1045                 1050

Gln Val  Glu Gly Glu Val Gln  Val Val Ser Thr Ala  Thr Gln Ser
    1055                 1060                 1065

Phe Leu  Ala Thr Cys Ile Asn  Gly Val Cys Trp Thr  Val Phe His
    1070                 1075                 1080

Gly Ala  Gly Ser Lys Thr Leu  Ala Gly Pro Lys Gly  Pro Ile Thr
    1085                 1090                 1095

Gln Met  Tyr Thr Asn Val Asp  Gln Asp Leu Val Gly  Trp Pro Ala
    1100                 1105                 1110

Pro Pro  Gly Ala Arg Ser Leu  Thr Pro Cys Thr Cys  Gly Ser Ser
    1115                 1120                 1125

Asp Leu  Tyr Leu Val Thr Arg  His Ala Asp Val Ile  Pro Val Arg
    1130                 1135                 1140

Arg Arg  Gly Asp Gly Arg Gly  Ser Leu Leu Pro Pro  Arg Pro Val
    1145                 1150                 1155

Ser Tyr  Leu Lys Gly Ser Ser  Gly Gly Pro Leu Leu  Cys Pro Ser
    1160                 1165                 1170

Gly His  Ala Val Gly Ile Leu  Pro Ala Ala Val Cys  Thr Arg Gly
    1175                 1180                 1185

Val Ala  Met Ala Val Glu Phe  Ile Pro Val Glu Ser  Met Glu Thr
    1190                 1195                 1200

Thr Met  Arg Ser Pro Val Phe  Thr Asp Asn Pro Ser  Pro Pro Ala
    1205                 1210                 1215

Val Pro  Gln Thr Phe Gln Val  Ala His Leu His Ala  Pro Thr Gly
    1220                 1225                 1230

Ser Gly  Lys Ser Thr Arg Val  Pro Ala Ala Tyr Ala  Ala Gln Gly
    1235                 1240                 1245

Tyr Lys  Val Leu Val Leu Asn  Pro Ser Val Ala Ala  Thr Leu Gly
    1250                 1255                 1260
```

```
Phe Gly Ala Tyr Met Ser Lys Ala His Gly Ile Asp Pro Asn Leu
    1265                 1270                 1275

Arg Thr Gly Val Arg Thr Ile Thr Thr Gly Ala Pro Ile Thr Tyr
    1280                 1285                 1290

Ser Thr Tyr Gly Lys Phe Leu Ala Asp Gly Gly Gly Ser Gly Gly
    1295                 1300                 1305

Ala Tyr Asp Ile Ile Met Cys Asp Glu Cys His Ser Thr Asp Ser
    1310                 1315                 1320

Thr Thr Ile Tyr Gly Ile Gly Thr Val Leu Asp Gln Ala Glu Thr
    1325                 1330                 1335

Ala Gly Ala Arg Leu Val Val Leu Ser Thr Ala Thr Pro Pro Gly
    1340                 1345                 1350

Ser Val Thr Val Pro His Leu Asn Ile Glu Glu Val Ala Leu Ser
    1355                 1360                 1365

Asn Thr Gly Glu Ile Pro Phe Tyr Gly Lys Ala Ile Pro Ile Glu
    1370                 1375                 1380

Ala Ile Lys Gly Gly Arg His Leu Ile Phe Cys His Ser Lys Lys
    1385                 1390                 1395

Lys Cys Asp Glu Leu Ala Ala Lys Leu Ser Gly Leu Gly Leu Asn
    1400                 1405                 1410

Ala Val Ala Tyr Tyr Arg Gly Leu Asp Val Ser Val Ile Pro Thr
    1415                 1420                 1425

Ser Gly Asp Val Val Val Val Ala Thr Asp Ala Leu Met Thr Gly
    1430                 1435                 1440

Phe Thr Gly Asp Phe Asp Ser Val Ile Asp Cys Asn Thr Cys Val
    1445                 1450                 1455

Thr Gln Thr Val Asp Phe Ser Leu Asp Pro Thr Phe Thr Ile Glu
    1460                 1465                 1470

Thr Thr Thr Val Pro Gln Asp Ala Val Ser Arg Ser Gln Arg Arg
    1475                 1480                 1485

Gly Arg Thr Gly Arg Gly Arg Ala Gly Ile Tyr Arg Phe Val Thr
    1490                 1495                 1500

Pro Gly Glu Arg Pro Ser Gly Met Phe Asp Ser Ser Val Leu Cys
    1505                 1510                 1515

Glu Cys Tyr Asp Ala Gly Cys Ala Trp Tyr Glu Leu Thr Pro Ala
    1520                 1525                 1530

Glu Thr Ser Val Arg Leu Arg Ala Tyr Leu Asn Thr Pro Gly Leu
    1535                 1540                 1545

Pro Val Cys Gln Asp His Leu Glu Phe Ser Glu Gly Val Phe Thr
    1550                 1555                 1560

Gly Leu Thr His Ile Asp Ala His Phe Leu Ser Gln Thr Lys Gln
    1565                 1570                 1575

Ala Gly Glu Asn Phe Pro Tyr Leu Val Ala Tyr Gln Ala Thr Val
    1580                 1585                 1590

Cys Ala Arg Ala Gln Ala Pro Pro Pro Ser Trp Asp Glu Met Trp
    1595                 1600                 1605

Arg Cys Leu Ile Arg Leu Lys Pro Thr Leu His Gly Pro Thr Pro
    1610                 1615                 1620

Leu Leu Tyr Arg Leu Gly Ala Val Gln Asn Glu Val Thr Leu Thr
    1625                 1630                 1635

His Pro Ile Thr Lys Phe Ile Met Thr Cys Met Ser Ala Asp Leu
    1640                 1645                 1650
```

-continued

```
Glu Val  Val Thr Ser Thr Trp  Val Leu Val Gly Gly  Val Leu Ala
    1655                 1660                 1665

Ala Leu  Ala Ala Tyr Cys Leu  Thr Thr Gly Ser Val  Val Ile Val
    1670                 1675                 1680

Gly Arg  Ile Ile Leu Ser Gly  Lys Pro Ala Ile Ile  Pro Asp Arg
    1685                 1690                 1695

Glu Val  Leu Tyr Gln Glu Phe  Asp Glu Met Glu Glu  Cys Ala Ser
    1700                 1705                 1710

His Leu  Pro Tyr Phe Glu Gln  Gly Met Gln Leu Ala  Glu Gln Phe
    1715                 1720                 1725

Lys Gln  Lys Ala Leu Gly Leu  Leu Gln Thr Ala Thr  Lys Gln Ala
    1730                 1735                 1740

Glu Ala  Ala Ala Pro Val Val  Glu Ser Lys Trp Arg  Ala Leu Glu
    1745                 1750                 1755

Thr Phe  Trp Ala Lys His Met  Trp Asn Phe Ile Ser  Gly Ile Gln
    1760                 1765                 1770

Tyr Leu  Ala Gly Leu Ser Thr  Leu Pro Gly Asn Pro  Ala Ile Arg
    1775                 1780                 1785

Ser Pro  Met Ala Phe Thr Ala  Ser Ile Thr Ser Pro  Leu Thr Thr
    1790                 1795                 1800

Gln His  Thr Leu Leu Phe Asn  Ile Leu Gly Gly Trp  Val Ala Ala
    1805                 1810                 1815

Gln Leu  Ala Pro Pro Ser Ala  Ala Ser Ala Phe Val  Gly Ala Gly
    1820                 1825                 1830

Ile Ala  Gly Ala Ala Val Gly  Thr Ile Gly Leu Gly  Lys Val Leu
    1835                 1840                 1845

Val Asp  Ile Leu Ala Gly Tyr  Gly Ala Gly Val Ala  Gly Ala Leu
    1850                 1855                 1860

Val Ala  Phe Lys Ile Met Ser  Gly Glu Met Pro Ser  Ala Glu Asp
    1865                 1870                 1875

Met Val  Asn Leu Leu Pro Ala  Ile Leu Ser Pro Gly  Ala Leu Val
    1880                 1885                 1890

Val Gly  Ile Val Cys Ala Ala  Ile Leu Arg Arg His  Val Gly Pro
    1895                 1900                 1905

Gly Glu  Gly Ala Val Gln Trp  Met Asn Arg Leu Ile  Ala Phe Ala
    1910                 1915                 1920

Ser Arg  Gly Asn His Val Ser  Pro Arg His Tyr Val  Pro Glu Ser
    1925                 1930                 1935

Glu Pro  Ala Ala Arg Val Thr  Gln Ile Leu Ser Ser  Leu Thr Ile
    1940                 1945                 1950

Thr Gln  Leu Leu Lys Arg Leu  His Gln Trp Ile Asn  Glu Asp Cys
    1955                 1960                 1965

Ser Thr  Pro Cys Ser Ser Ser  Trp Leu Arg Glu Ile  Trp Asp Trp
    1970                 1975                 1980

Ile Cys  Thr Val Leu Thr Asp  Phe Lys Thr Trp Leu  Gln Ser Lys
    1985                 1990                 1995

Leu Leu  Pro Arg Leu Pro Gly  Val Pro Phe Phe Ser  Cys Gln Arg
    2000                 2005                 2010

Gly Tyr  Lys Gly Val Trp Arg  Gly Asp Gly Ile Met  His Thr Thr
    2015                 2020                 2025

Cys Pro  Cys Gly Ala Gln Ile  Thr Gly His Val Lys  Asn Gly Ser
    2030                 2035                 2040

Met Arg  Ile Val Gly Pro Lys  Thr Cys Ser Asn Thr  Trp Tyr Gly
```

-continued

```
    2045                2050                2055

Thr Phe  Pro Ile Asn Ala Tyr  Thr Thr Gly Pro Cys  Thr Pro Ser
    2060                2065                2070

Pro Ala  Pro Asn Tyr Ser Lys  Ala Leu Trp Arg Val  Ala Ala Glu
    2075                2080                2085

Glu Tyr  Val Glu Val Thr Arg  Val Gly Asp Phe His  Tyr Val Thr
    2090                2095                2100

Gly Met  Thr Thr Asp Asn Val  Lys Cys Pro Cys Gln  Val Pro Ala
    2105                2110                2115

Pro Glu  Phe Phe Thr Glu Val  Asp Gly Val Arg Leu  His Arg Tyr
    2120                2125                2130

Ala Pro  Ala Cys Arg Pro Leu  Leu Arg Glu Glu Val  Val Phe Gln
    2135                2140                2145

Val Gly  Leu His Gln Tyr Leu  Val Gly Ser Gln Leu  Pro Cys Glu
    2150                2155                2160

Pro Glu  Pro Asp Val Ala Val  Leu Thr Ser Met Leu  Thr Asp Pro
    2165                2170                2175

Ser His  Ile Thr Ala Glu Thr  Ala Lys Arg Arg Leu  Ala Arg Gly
    2180                2185                2190

Ser Pro  Pro Ser Leu Ala Ser  Ser Ser Ala Ser Gln  Leu Ser Ala
    2195                2200                2205

Pro Ser  Leu Lys Ala Thr Cys  Thr Thr His His Asp  Ser Pro Asp
    2210                2215                2220

Ala Asp  Leu Ile Glu Ala Asn  Leu Leu Trp Arg Gln  Glu Met Gly
    2225                2230                2235

Gly Asn  Ile Thr Arg Val Glu  Ser Glu Asn Lys Val  Val Ile Leu
    2240                2245                2250

Asp Ser  Phe Asp Pro Leu Arg  Ala Glu Asp Asp Glu  Gly Glu Ile
    2255                2260                2265

Ser Val  Pro Ala Glu Ile Leu  Arg Lys Ser Arg Lys  Phe Pro Pro
    2270                2275                2280

Ala Leu  Pro Ile Trp Ala Pro  Pro Asp Tyr Asn Pro  Pro Leu Leu
    2285                2290                2295

Glu Ser  Trp Lys Asp Pro Asp  Tyr Val Pro Pro Val  Val His Gly
    2300                2305                2310

Cys Pro  Leu Pro Pro Thr Lys  Ala Pro Pro Ile Pro  Pro Pro Arg
    2315                2320                2325

Arg Lys  Arg Thr Val Val Leu  Thr Glu Ser Thr Val  Ser Ser Ala
    2330                2335                2340

Leu Ala  Glu Leu Ala Thr Lys  Thr Phe Gly Ser Ser  Gly Ser Ser
    2345                2350                2355

Ala Ile  Asp Ser Gly Thr Ala  Thr Ala Pro Pro Asp  Gln Ala Ser
    2360                2365                2370

Gly Asp  Gly Asp Arg Glu Ser  Asp Val Glu Ser Phe  Ser Ser Met
    2375                2380                2385

Pro Pro  Leu Glu Gly Glu Pro  Gly Asp Pro Asp Leu  Ser Asp Gly
    2390                2395                2400

Ser Trp  Ser Thr Val Ser Glu  Glu Ala Ser Glu Asp  Val Val Cys
    2405                2410                2415

Cys Ser  Met Ser Tyr Thr Trp  Thr Gly Ala Leu Ile  Thr Pro Cys
    2420                2425                2430

Ala Ala  Glu Glu Ser Lys Leu  Pro Ile Asn Pro Leu  Ser Asn Ser
    2435                2440                2445
```

-continued

```
Leu Leu Arg His His Asn Met Val Tyr Ala Thr Thr Ser Arg Ser
    2450                2455                2460

Ala Gly Leu Arg Gln Lys Lys Val Thr Phe Asp Arg Leu Gln Val
    2465                2470                2475

Leu Asp Asp His Tyr Arg Asp Val Leu Lys Glu Met Lys Ala Lys
    2480                2485                2490

Ala Ser Thr Val Lys Ala Lys Leu Leu Ser Val Glu Glu Ala Cys
    2495                2500                2505

Lys Leu Thr Pro Pro His Ser Ala Lys Ser Lys Phe Gly Tyr Gly
    2510                2515                2520

Ala Lys Asp Val Arg Ser Leu Ser Ser Arg Ala Val Thr His Ile
    2525                2530                2535

Arg Ser Val Trp Lys Asp Leu Leu Glu Asp Thr Glu Thr Pro Ile
    2540                2545                2550

Ser Thr Thr Ile Met Ala Lys Asn Glu Val Phe Cys Val Gln Pro
    2555                2560                2565

Glu Lys Gly Gly Arg Lys Pro Ala Arg Leu Ile Val Phe Pro Asp
    2570                2575                2580

Leu Gly Val Arg Val Cys Glu Lys Met Ala Leu Tyr Asp Val Val
    2585                2590                2595

Ser Thr Leu Pro Gln Ala Val Met Gly Ser Ser Tyr Gly Phe Gln
    2600                2605                2610

Tyr Ser Pro Lys Gln Arg Val Glu Phe Leu Val Asn Thr Trp Lys
    2615                2620                2625

Ser Lys Lys Cys Pro Met Gly Phe Ser Tyr Asp Thr Arg Cys Phe
    2630                2635                2640

Asp Ser Thr Val Thr Glu Asn Asp Ile Arg Val Glu Glu Ser Ile
    2645                2650                2655

Tyr Gln Cys Cys Asp Leu Ala Pro Glu Ala Lys Leu Ala Ile Lys
    2660                2665                2670

Ser Leu Thr Glu Arg Leu Tyr Ile Gly Gly Pro Leu Thr Asn Ser
    2675                2680                2685

Lys Gly Gln Asn Cys Gly Tyr Arg Arg Cys Arg Ala Ser Gly Val
    2690                2695                2700

Leu Thr Thr Ser Cys Gly Asn Thr Leu Thr Cys Tyr Leu Lys Ala
    2705                2710                2715

Thr Ala Ala Cys Arg Ala Ala Lys Leu Arg Asp Cys Thr Met Leu
    2720                2725                2730

Val Asn Gly Asp Asp Leu Val Val Ile Cys Glu Ser Ala Gly Thr
    2735                2740                2745

Gln Glu Asp Ala Ala Ser Leu Arg Val Phe Thr Glu Ala Met Thr
    2750                2755                2760

Arg Tyr Ser Ala Pro Pro Gly Asp Pro Pro Gln Pro Glu Tyr Asp
    2765                2770                2775

Leu Glu Leu Ile Thr Ser Cys Ser Ser Asn Val Ser Val Ala His
    2780                2785                2790

Asp Ala Ser Gly Lys Arg Val Tyr Tyr Leu Thr Arg Asp Pro Thr
    2795                2800                2805

Thr Pro Leu Ala Arg Ala Ala Trp Glu Thr Ala Arg His Thr Pro
    2810                2815                2820

Val Asn Ser Trp Leu Gly Asn Ile Ile Met Tyr Ala Pro Thr Leu
    2825                2830                2835
```

-continued

```
Trp Ala  Arg Met Ile Leu Met  Thr His Phe Phe Ser  Ile Leu Leu
    2840                 2845                 2850

Ala Gln  Glu Gln Leu Glu Lys  Thr Leu Asp Cys Gln  Ile Tyr Gly
    2855                 2860                 2865

Ala Cys  Tyr Ser Ile Glu Pro  Leu Asp Leu Pro Gln  Ile Ile Glu
    2870                 2875                 2880

Arg Leu  His Gly Leu Ser Ala  Phe Ser Leu His Ser  Tyr Ser Pro
    2885                 2890                 2895

Gly Glu  Ile Asn Arg Val Ala  Ser Cys Leu Arg Lys  Leu Gly Val
    2900                 2905                 2910

Pro Pro  Leu Arg Ala Trp Arg  His Arg Ala Arg Ser  Val Arg Ala
    2915                 2920                 2925

Lys Leu  Leu Ser Gln Gly Gly  Arg Ala Ala Thr Cys  Gly Lys Tyr
    2930                 2935                 2940

Leu Phe  Asn Trp Ala Val Arg  Thr Lys Leu Lys Leu  Thr Pro Ile
    2945                 2950                 2955

Pro Ala  Ala Ser Arg Leu Asp  Leu Ser Gly Trp Phe  Val Ala Gly
    2960                 2965                 2970

Tyr Ser  Gly Gly Asp Ile Tyr  His Ser Leu Ser Arg  Ala Arg Pro
    2975                 2980                 2985

Arg Trp  Phe Met Leu Cys Leu  Leu Leu Leu Ser Val  Gly Val Gly
    2990                 2995                 3000

Ile Tyr  Leu Leu Pro Asn Arg
    3005                 3010
```

<210> SEQ ID NO 4
<211> LENGTH: 486
<212> TYPE: PRT
<213> ORGANISM: influenza A virus

<400> SEQUENCE: 4

```
Met Ala Ser Gln Gly Thr Lys Arg Ser Tyr Glu Gln Met Glu Thr Ser
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190
```

```
Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser
                485
```

<210> SEQ ID NO 5
<211> LENGTH: 97
<212> TYPE: PRT
<213> ORGANISM: influenza A virus

<400> SEQUENCE: 5

```
Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
```

```
65                  70                  75                  80

Gln Asn Ala Val Asp Ala Asp Asp Ser His Phe Val Ser Ile Glu Leu
                85                  90                  95

Glu


<210> SEQ ID NO 6
<211> LENGTH: 498
<212> TYPE: PRT
<213> ORGANISM: influenza A virus

<400> SEQUENCE: 6

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp His Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
```

```
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 7
<211> LENGTH: 97
<212> TYPE: PRT
<213> ORGANISM: influenza A virus

<400> SEQUENCE: 7

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu


<210> SEQ ID NO 8
<211> LENGTH: 498
<212> TYPE: PRT
<213> ORGANISM: influenza A virus

<400> SEQUENCE: 8

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60
```

-continued

```
Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
```

```
                485                 490                 495

Asp Asn


<210> SEQ ID NO 9
<211> LENGTH: 97
<212> TYPE: PRT
<213> ORGANISM: influenza A virus

<400> SEQUENCE: 9

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Phe Ile Leu Trp Ile Leu Asp Arg Leu Phe Phe
        35                  40                  45

Lys Cys Ile Tyr Arg Phe Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Ala Asp Asp Ser His Phe Val Ser Ile Glu Leu
                85                  90                  95

Glu


<210> SEQ ID NO 10
<211> LENGTH: 498
<212> TYPE: PRT
<213> ORGANISM: influenza A virus

<400> SEQUENCE: 10

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205
```

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Ile Ala Ser Gly
        275                 280                 285

Tyr Asn Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Asp Lys Pro Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Met Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 11
<211> LENGTH: 551
<212> TYPE: PRT
<213> ORGANISM: Human herpesvirus 5

<400> SEQUENCE: 11

Met Ala Ser Val Leu Gly Pro Ile Ser Gly His Val Leu Lys Ala Val
1               5                   10                  15

Phe Ser Arg Gly Asp Thr Pro Val Leu Pro His Glu Thr Arg Leu Leu
            20                  25                  30

Gln Thr Gly Ile His Val Arg Val Ser Gln Pro Ser Leu Ile Leu Val
        35                  40                  45

Ser Gln Tyr Thr Pro Asp Ser Thr Pro Cys His Arg Gly Asp Asn Gln
    50                  55                  60

Leu Gln Val Gln His Thr Tyr Phe Thr Gly Ser Glu Val Glu Asn Val
65                  70                  75                  80

-continued

```
Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
            100                 105                 110

Ile Pro Ser Ile Asn Val His His Tyr Pro Ser Ala Ala Glu Arg Lys
        115                 120                 125

His Arg His Leu Pro Val Ala Asp Ala Val Ile His Ala Ser Gly Lys
    130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
        195                 200                 205

Ile Gly Asp Gln Tyr Val Lys Val Tyr Leu Glu Ser Phe Cys Glu Asp
    210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
                245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
        275                 280                 285

His Glu His Phe Gly Leu Leu Cys Pro Lys Ser Ile Pro Gly Leu Ser
    290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Leu Gln Arg Gly Pro Gln
            340                 345                 350

Tyr Ser Glu His Pro Thr Phe Thr Ser Gln Tyr Arg Ile Gln Gly Lys
        355                 360                 365

Leu Glu Tyr Arg His Thr Trp Asp Arg His Asp Glu Gly Ala Ala Gln
    370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Gly Ala Met
                405                 410                 415

Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
        435                 440                 445

Glu Ser Thr Val Ala Pro Glu Glu Asp Thr Asp Glu Asp Ser Asp Asn
    450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
```

-continued

```
            500                 505                 510

Ile Phe Ala Glu Leu Glu Gly Val Trp Gln Pro Ala Ala Gln Pro Lys
        515                 520                 525

Arg Arg Arg His Arg Gln Asp Ala Leu Pro Gly Pro Cys Ile Ala Ser
    530                 535                 540

Thr Pro Lys Lys His Arg Gly
545                 550
```

<210> SEQ ID NO 12
<211> LENGTH: 158
<212> TYPE: PRT
<213> ORGANISM: Human papillomavirus type 16

<400> SEQUENCE: 12

```
Met His Gln Lys Arg Thr Ala Met Phe Gln Asp Pro Gln Glu Arg Pro
1               5                   10                  15

Gly Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

<210> SEQ ID NO 13
<211> LENGTH: 97
<212> TYPE: PRT
<213> ORGANISM: Influenza A virus

<400> SEQUENCE: 13

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu
```

<210> SEQ ID NO 14

<211> LENGTH: 759
<212> TYPE: PRT
<213> ORGANISM: Influenza A virus

<400> SEQUENCE: 14

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Lys Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Gly Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
```

385 390 395 400

Ala Met Val Phe Ser Gln Glu Asp Cys Met Ile Lys Ala Val Arg Gly
405 410 415

Asp Leu Asn Phe Val Asn Arg Ala Asn Gln Arg Leu Asn Pro Met His
420 425 430

Gln Leu Leu Arg His Phe Gln Lys Asp Ala Lys Val Leu Phe Gln Asn
435 440 445

Trp Gly Val Glu Pro Ile Asp Asn Val Met Gly Met Ile Gly Ile Leu
450 455 460

Pro Asp Met Thr Pro Ser Ile Glu Met Ser Met Arg Gly Val Arg Ile
465 470 475 480

Ser Lys Met Gly Val Asp Glu Tyr Ser Ser Thr Glu Arg Val Val Val
485 490 495

Ser Ile Asp Arg Phe Leu Arg Val Arg Asp Gln Arg Gly Asn Val Leu
500 505 510

Leu Ser Pro Glu Glu Val Ser Glu Thr Gln Gly Thr Glu Lys Leu Thr
515 520 525

Ile Thr Tyr Ser Ser Ser Met Met Trp Glu Ile Asn Gly Pro Glu Ser
530 535 540

Val Leu Val Asn Thr Tyr Gln Trp Ile Ile Arg Asn Trp Glu Thr Val
545 550 555 560

Lys Ile Gln Trp Ser Gln Asn Pro Thr Met Leu Tyr Asn Lys Met Glu
565 570 575

Phe Glu Pro Phe Gln Ser Leu Val Pro Lys Ala Ile Arg Gly Gln Tyr
580 585 590

Ser Gly Phe Val Arg Thr Leu Phe Gln Gln Met Arg Asp Val Leu Gly
595 600 605

Thr Phe Asp Thr Ala Gln Ile Ile Lys Leu Leu Pro Phe Ala Ala Ala
610 615 620

Pro Pro Lys Gln Ser Arg Met Gln Phe Ser Ser Phe Thr Val Asn Val
625 630 635 640

Arg Gly Ser Gly Met Arg Ile Leu Val Arg Gly Asn Ser Pro Val Phe
645 650 655

Asn Tyr Asn Lys Ala Thr Lys Arg Leu Thr Val Leu Gly Lys Asp Ala
660 665 670

Gly Thr Leu Thr Glu Asp Pro Asp Glu Gly Thr Ala Gly Val Glu Ser
675 680 685

Ala Val Leu Arg Gly Phe Leu Ile Leu Gly Lys Glu Asp Arg Arg Tyr
690 695 700

Gly Pro Ala Leu Ser Ile Asn Glu Leu Ser Asn Leu Ala Lys Gly Glu
705 710 715 720

Lys Ala Asn Val Leu Ile Gly Gln Gly Asp Val Val Leu Val Met Lys
725 730 735

Arg Lys Arg Asp Ser Ser Ile Leu Thr Asp Ser Gln Thr Ala Thr Lys
740 745 750

Arg Ile Arg Met Ala Ile Asn
755

<210> SEQ ID NO 15
<211> LENGTH: 716
<212> TYPE: PRT
<213> ORGANISM: Influenza A virus

<400> SEQUENCE: 15

-continued

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
```

420 425 430

Ala Pro Ile Glu His Ile Ala Ser Met Arg Arg Asn Tyr Phe Thr Ser
435 440 445

Glu Val Ser His Cys Arg Ala Thr Glu Tyr Ile Met Lys Gly Val Tyr
450 455 460

Ile Asn Thr Ala Leu Leu Asn Ala Ser Cys Ala Ala Met Asp Asp Phe
465 470 475 480

Gln Leu Ile Pro Met Ile Ser Lys Cys Arg Thr Lys Glu Gly Arg Arg
485 490 495

Lys Thr Asn Leu Tyr Gly Phe Ile Ile Lys Gly Arg Ser His Leu Arg
500 505 510

Asn Asp Thr Asp Val Val Asn Phe Val Ser Met Glu Phe Ser Leu Thr
515 520 525

Asp Pro Arg Leu Glu Pro His Lys Trp Glu Lys Tyr Cys Val Leu Glu
530 535 540

Ile Gly Asp Met Leu Leu Arg Ser Ala Ile Gly Gln Val Ser Arg Pro
545 550 555 560

Met Phe Leu Tyr Val Arg Thr Asn Gly Thr Ser Lys Ile Lys Met Lys
565 570 575

Trp Gly Met Glu Met Arg Arg Cys Leu Leu Gln Ser Leu Gln Gln Ile
580 585 590

Glu Ser Met Ile Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Lys Gly Val Glu Glu Ser Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Asn Leu Glu Pro Gly Thr Phe Asp Leu Gly Gly Leu Tyr Glu
675 680 685

Ala Ile Glu Glu Cys Leu Ile Asn Asp Pro Trp Val Leu Leu Asn Ala
690 695 700

Ser Trp Phe Asn Ser Phe Leu Thr His Ala Leu Ser
705 710 715

<210> SEQ ID NO 16
<211> LENGTH: 230
<212> TYPE: PRT
<213> ORGANISM: Influenza A virus

<400> SEQUENCE: 16

Met Asp Pro Asn Thr Val Ser Ser Phe Gln Val Asp Cys Phe Leu Trp
1 5 10 15

His Val Arg Lys Arg Val Ala Asp Gln Glu Leu Gly Asp Ala Pro Phe
20 25 30

Leu Asp Arg Leu Arg Arg Asp Gln Lys Ser Leu Arg Gly Arg Gly Ser
35 40 45

Thr Leu Gly Leu Asp Ile Glu Thr Ala Thr Arg Ala Gly Lys Gln Ile
50 55 60

Val Glu Arg Ile Leu Lys Glu Glu Ser Asp Glu Ala Leu Lys Met Thr
65 70 75 80

-continued

```
Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230


<210> SEQ ID NO 17
<211> LENGTH: 121
<212> TYPE: PRT
<213> ORGANISM: Influenza A virus

<400> SEQUENCE: 17

Met Asp Pro Asn Thr Val Ser Ser Phe Gln Asp Ile Leu Leu Arg Met
1               5                   10                  15

Ser Lys Met Gln Leu Glu Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Val Thr Glu Asn Ser Phe Glu Gln
                85                  90                  95

Ile Thr Phe Met Gln Ala Leu His Leu Leu Leu Glu Val Glu Gln Glu
            100                 105                 110

Ile Arg Thr Phe Ser Phe Gln Leu Ile
        115                 120


<210> SEQ ID NO 18
<211> LENGTH: 454
<212> TYPE: PRT
<213> ORGANISM: Influenza A virus

<400> SEQUENCE: 18

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45
```

```
Cys Asn Gln Asn Ile Ile Thr Tyr Lys Asn Ser Thr Trp Val Lys Asp
    50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ala Leu Leu Asn Asp Arg
        115                 120                 125

His Ser Asn Gly Thr Val Lys Asp Arg Ser Pro Tyr Arg Ala Leu Met
    130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
            180                 185                 190

Tyr Asn Gly Ile Ile Thr Glu Thr Ile Lys Ser Trp Arg Lys Lys Ile
        195                 200                 205

Leu Arg Thr Gln Glu Ser Glu Cys Ala Cys Val Asn Gly Ser Cys Phe
    210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
            260                 265                 270

Val Met Cys Val Cys Arg Asp Asn Trp His Gly Ser Asn Arg Pro Trp
        275                 280                 285

Val Ser Phe Asp Gln Asn Leu Asp Tyr Gln Ile Gly Tyr Ile Cys Ser
    290                 295                 300

Gly Val Phe Gly Asp Asn Pro Arg Pro Lys Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
            340                 345                 350

Arg His Gly Phe Glu Met Ile Trp Asp Pro Asn Gly Trp Thr Glu Thr
        355                 360                 365

Asp Ser Lys Phe Ser Val Arg Gln Asp Val Val Ala Met Thr Asp Trp
    370                 375                 380

Ser Gly Tyr Ser Gly Ser Phe Val Gln His Pro Glu Leu Thr Gly Leu
385                 390                 395                 400

Asp Cys Ile Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
            420                 425                 430

Val Asn Ser Asp Thr Val Asp Trp Ser Trp Pro Asp Gly Ala Glu Leu
        435                 440                 445

Pro Phe Thr Ile Asp Lys
    450
```

-continued

<210> SEQ ID NO 19
<211> LENGTH: 566
<212> TYPE: PRT
<213> ORGANISM: Influenza A virus

<400> SEQUENCE: 19

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Glu Lys Glu Gly Ser Tyr Pro
                165                 170                 175

Lys Leu Lys Asn Ser Tyr Val Asn Lys Lys Gly Lys Glu Val Leu Val
            180                 185                 190

Leu Trp Gly Ile His His Pro Ser Asn Ser Lys Asp Gln Gln Asn Ile
        195                 200                 205

Tyr Gln Asn Glu Asn Ala Tyr Val Ser Val Val Thr Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Lys Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

-continued

```
Thr Gln Asn Ala Ile Asn Gly Ile Thr Asn Lys Val Asn Ser Val Ile
385                 390                 395                 400

Glu Lys Met Asn Ile Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 20
<211> LENGTH: 252
<212> TYPE: PRT
<213> ORGANISM: Influenza A virus

<400> SEQUENCE: 20

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

Ala Gly Ser Ser Glu Gln Ala Ala Glu Ala Met Glu Val Ala Ser Gln
195 200 205

Ala Arg Gln Met Val Gln Ala Met Arg Thr Ile Gly Thr His Pro Ser
210 215 220

Ser Ser Ala Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 21
<211> LENGTH: 87
<212> TYPE: PRT
<213> ORGANISM: Influenza A virus

<400> SEQUENCE: 21

Met Gly Gln Glu Gln Asp Thr Pro Trp Ile Leu Ser Thr Gly His Ile
1 5 10 15

Ser Thr Gln Lys Arg Gln Asp Gly Gln Gln Thr Pro Lys Leu Glu His
20 25 30

Arg Asn Ser Thr Arg Leu Met Gly His Cys Gln Lys Thr Met Asn Gln
35 40 45

Val Val Met Pro Lys Gln Ile Val Tyr Trp Lys Gln Trp Leu Ser Leu
50 55 60

Arg Asn Pro Ile Leu Val Phe Leu Lys Thr Arg Val Leu Lys Arg Trp
65 70 75 80

Arg Leu Phe Ser Lys His Glu
85

<210> SEQ ID NO 22
<211> LENGTH: 757
<212> TYPE: PRT
<213> ORGANISM: Influenza A virus

<400> SEQUENCE: 22

Met Asp Val Asn Pro Thr Leu Leu Phe Leu Lys Val Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Ala Arg Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Ile Glu Thr Met Glu
100 105 110

Val Val Gln Gln Thr Arg Val Asp Lys Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Lys Lys
165 170 175

```
Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Arg
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Leu Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu His Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ser Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590
```

-continued

```
Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755


<210> SEQ ID NO 23
<211> LENGTH: 498
<212> TYPE: PRT
<213> ORGANISM: Influenza A virus

<400> SEQUENCE: 23

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205
```

```
Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 24
<211> LENGTH: 759
<212> TYPE: PRT
<213> ORGANISM: Influenza A virus

<400> SEQUENCE: 24

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80
```

```
Met Ser Asp Ala Gly Ser Asp Arg Val Met Val Ser Pro Leu Ala Val
                85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Ile Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Val Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Asn Val Met Gly Met Ile Gly Val Leu
    450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495
```

```
Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Thr Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 25
<211> LENGTH: 562
<212> TYPE: PRT
<213> ORGANISM: Influenza A virus

<400> SEQUENCE: 25

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Tyr Ser Leu Cys Tyr Pro Gly Ser Phe Asn Asp
            100                 105                 110
```

```
Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Trp Ala Cys Ala Val Ser Gly Lys Pro Ser Phe Phe Arg Asn
145                 150                 155                 160

Met Val Trp Leu Thr Arg Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Ala Glu Gln Arg Ala Leu Tyr Gln Asn Val
        195                 200                 205

Gly Thr Tyr Val Ser Val Ala Thr Ser Thr Leu Tyr Lys Arg Ser Ile
    210                 215                 220

Pro Glu Ile Ala Ala Arg Pro Lys Val Asn Gly Leu Gly Arg Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Val Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asn Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asn Glu Cys Met Asp Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525
```

-continued

```
Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 26
<211> LENGTH: 252
<212> TYPE: PRT
<213> ORGANISM: Influenza A virus

<400> SEQUENCE: 26

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Ala Val Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr Pro Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 27
<211> LENGTH: 97
<212> TYPE: PRT
<213> ORGANISM: Influenza A virus

<400> SEQUENCE: 27

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Phe Ile Leu Trp Ile Leu Asp Arg Leu Phe Phe
```

35 40 45

Lys Cys Ile Tyr Arg Phe Phe Lys His Gly Leu Lys Arg Gly Pro Ser
50 55 60

Thr Glu Gly Val Pro Glu Ser Met Arg Glu Glu Tyr Arg Lys Glu Gln
65 70 75 80

Gln Ser Ala Val Asp Ala Asp Asp Ser His Phe Val Ser Ile Glu Leu
85 90 95

Glu

<210> SEQ ID NO 28
<211> LENGTH: 716
<212> TYPE: PRT
<213> ORGANISM: Influenza A virus

<400> SEQUENCE: 28

Met Glu Asp Phe Val Arg Gln Cys Phe Asn Pro Met Ile Val Glu Leu
1 5 10 15

Ala Glu Lys Ala Met Lys Glu Tyr Gly Glu Asp Leu Lys Ile Glu Thr
20 25 30

Asn Lys Phe Ala Ala Ile Cys Thr His Leu Glu Val Cys Phe Met Tyr
35 40 45

Ser Asp Phe His Phe Ile Asn Glu Gln Gly Glu Ser Ile Met Val Glu
50 55 60

Leu Asp Asp Pro Asn Ala Leu Leu Lys His Arg Phe Glu Ile Ile Glu
65 70 75 80

Gly Arg Asp Arg Thr Met Ala Trp Thr Val Val Asn Ser Ile Cys Asn
85 90 95

Thr Thr Gly Ala Glu Lys Pro Lys Phe Leu Pro Asp Leu Tyr Asp Tyr
100 105 110

Lys Glu Asn Arg Phe Ile Glu Ile Gly Val Thr Arg Arg Glu Val His
115 120 125

Ile Tyr Tyr Leu Glu Lys Ala Asn Lys Ile Lys Ser Glu Asn Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Asn Arg Gly Leu Trp Asp Ser Phe Arg
180 185 190

Gln Ser Glu Arg Gly Glu Glu Thr Ile Glu Glu Arg Phe Glu Ile Thr
195 200 205

Gly Thr Met Arg Arg Leu Ala Asp Gln Ser Leu Pro Pro Asn Phe Ser
210 215 220

Cys Leu Glu Asn Phe Arg Ala Tyr Val Asp Gly Phe Glu Pro Asn Gly
225 230 235 240

Tyr Ile Glu Gly Lys Leu Ser Gln Met Ser Lys Glu Val Asn Ala Lys
245 250 255

Ile Glu Pro Phe Leu Lys Thr Thr Pro Arg Pro Ile Arg Leu Pro Asp
260 265 270

Gly Pro Pro Cys Phe Gln Arg Ser Lys Phe Leu Leu Met Asp Ala Leu
275 280 285

Lys Leu Ser Ile Glu Asp Pro Ser His Glu Gly Glu Gly Ile Pro Leu
290 295 300

Tyr Asp Ala Ile Lys Cys Met Arg Thr Phe Phe Gly Trp Lys Glu Pro

-continued 305 310 315 320

Tyr Ile Val Lys Pro His Glu Lys Gly Ile Asn Pro Asn Tyr Leu Leu
325 330 335

Ser Trp Lys Gln Val Leu Ala Glu Leu Gln Asp Ile Glu Asn Glu Glu
340 345 350

Lys Ile Pro Arg Thr Lys Asn Met Lys Lys Thr Ser Gln Leu Lys Trp
355 360 365

Ala Leu Gly Glu Asn Met Ala Pro Glu Lys Val Asp Phe Asp Asn Cys
370 375 380

Arg Asp Ile Ser Asp Leu Lys Gln Tyr Asp Ser Asp Glu Pro Glu Leu
385 390 395 400

Arg Ser Leu Ser Ser Trp Ile Gln Asn Glu Phe Asn Lys Ala Cys Glu
405 410 415

Leu Thr Asp Ser Ile Trp Ile Glu Leu Asp Glu Ile Gly Glu Asp Val
420 425 430

Ala Pro Ile Glu His Ile Ala Ser Met Arg Arg Asn Tyr Phe Thr Ala
435 440 445

Glu Val Ser His Cys Arg Ala Thr Glu Tyr Ile Met Lys Gly Val Tyr
450 455 460

Ile Asn Thr Ala Leu Leu Asn Ala Ser Cys Ala Ala Met Asp Asp Phe
465 470 475 480

Gln Leu Ile Pro Met Ile Ser Lys Cys Arg Thr Lys Glu Gly Arg Arg
485 490 495

Lys Thr Asn Leu Tyr Gly Phe Ile Ile Lys Gly Arg Ser His Leu Arg
500 505 510

Asn Asp Thr Asp Val Val Asn Phe Val Ser Met Glu Phe Ser Leu Thr
515 520 525

Asp Pro Arg Leu Glu Pro His Lys Trp Glu Lys Tyr Cys Val Leu Glu
530 535 540

Ile Gly Asp Met Leu Leu Arg Ser Ala Ile Gly Gln Met Ser Arg Pro
545 550 555 560

Met Phe Leu Tyr Val Arg Thr Asn Gly Thr Ser Lys Ile Lys Met Lys
565 570 575

Trp Gly Met Glu Met Arg Pro Cys Leu Leu Gln Ser Leu Gln Gln Ile
580 585 590

Glu Ser Met Val Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Lys Gly Val Glu Glu Gly Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Val Val Gln Ala Leu
660 665 670

Arg Asp Asn Leu Glu Pro Gly Thr Phe Asp Leu Gly Gly Leu Tyr Glu
675 680 685

Ala Ile Glu Glu Cys Leu Ile Asn Asp Pro Trp Val Leu Leu Asn Ala
690 695 700

Ser Trp Phe Asn Ser Phe Leu Thr His Ala Leu Arg
705 710 715

<210> SEQ ID NO 29

<211> LENGTH: 90
<212> TYPE: PRT
<213> ORGANISM: Influenza A virus

<400> SEQUENCE: 29

```
Met Gly Gln Glu Gln Asp Thr Pro Trp Thr Gln Ser Thr Glu His Ile
1               5                   10                  15

Asn Ile Gln Lys Arg Gly Ser Gly Gln Gln Thr Arg Lys Leu Glu Arg
            20                  25                  30

Pro Asn Leu Thr Gln Leu Met Asp His Tyr Leu Arg Thr Met Asn Gln
        35                  40                  45

Val Asp Met His Lys Gln Thr Ala Ser Trp Lys Gln Trp Leu Ser Leu
    50                  55                  60

Arg Asn His Thr Gln Glu Ser Leu Lys Ile Arg Val Leu Lys Arg Trp
65                  70                  75                  80

Lys Leu Phe Asn Lys Gln Glu Trp Thr Asn
                85                  90
```

<210> SEQ ID NO 30
<211> LENGTH: 757
<212> TYPE: PRT
<213> ORGANISM: Influenza A virus

<400> SEQUENCE: 30

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val His Phe Val Glu
                245                 250                 255
```

Thr Leu Ala Arg Asn Ile Cys Glu Lys Leu Glu Gln Ser Gly Leu Pro
260 265 270

Val Gly Gly Asn Glu Lys Lys Ala Lys Leu Ala Asn Val Val Arg Lys
275 280 285

Met Met Thr Asn Ser Gln Asp Thr Glu Leu Ser Phe Thr Ile Thr Gly
290 295 300

Asp Asn Thr Lys Trp Asn Glu Asn Gln Asn Pro Arg Val Phe Leu Ala
305 310 315 320

Met Ile Thr Tyr Ile Thr Arg Asn Gln Pro Glu Trp Phe Arg Asn Val
325 330 335

Leu Ser Ile Ala Pro Ile Met Phe Ser Asn Lys Met Ala Arg Leu Gly
340 345 350

Lys Gly Tyr Met Phe Glu Ser Lys Ser Met Lys Leu Arg Thr Gln Ile
355 360 365

Pro Ala Glu Met Leu Ala Ser Ile Asp Leu Lys Tyr Phe Asn Glu Ser
370 375 380

Thr Arg Lys Lys Ile Glu Lys Ile Arg Pro Leu Leu Ile Asp Gly Thr
385 390 395 400

Val Ser Leu Ser Pro Gly Met Met Met Gly Met Phe Asn Met Leu Ser
405 410 415

Thr Val Leu Gly Val Ser Ile Leu Asn Leu Gly Gln Lys Lys Tyr Thr
420 425 430

Lys Thr Thr Tyr Trp Trp Asp Gly Leu Gln Ser Ser Asp Asp Phe Ala
435 440 445

Leu Ile Val Asn Ala Pro Asn His Glu Gly Ile Gln Ala Gly Val Asn
450 455 460

Arg Phe Tyr Arg Thr Cys Lys Leu Val Gly Ile Asn Met Ser Lys Lys
465 470 475 480

Lys Ser Tyr Ile Asn Arg Thr Gly Thr Phe Glu Phe Thr Ser Phe Phe
485 490 495

Tyr Arg Tyr Gly Phe Val Ala Asn Phe Ser Met Glu Leu Pro Ser Phe
500 505 510

Gly Val Ser Gly Ile Asn Glu Ser Ala Asp Met Ser Ile Gly Val Thr
515 520 525

Val Ile Lys Asn Asn Met Ile Asn Asn Asp Leu Gly Pro Ala Thr Ala
530 535 540

Gln Met Ala Leu Gln Leu Phe Ile Lys Asp Tyr Arg Tyr Thr Tyr Arg
545 550 555 560

Cys His Arg Gly Asp Thr Gln Ile Gln Thr Arg Arg Ser Phe Glu Leu
565 570 575

Lys Lys Leu Trp Glu Gln Thr Arg Ser Lys Ala Gly Leu Leu Val Ser
580 585 590

Asp Gly Gly Ser Asn Leu Tyr Asn Ile Arg Asn Leu His Ile Pro Glu
595 600 605

Val Cys Leu Lys Trp Glu Leu Met Asp Glu Asp Tyr Gln Gly Arg Leu
610 615 620

Cys Asn Pro Leu Asn Pro Phe Val Ser His Lys Glu Ile Glu Ser Val
625 630 635 640

Asn Asn Ala Val Val Met Pro Ala His Gly Pro Ala Lys Ser Met Glu
645 650 655

Tyr Asp Ala Val Ala Thr Thr His Ser Trp Thr Pro Lys Arg Asn Arg
660 665 670

```
Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755


<210> SEQ ID NO 31
<211> LENGTH: 121
<212> TYPE: PRT
<213> ORGANISM: Influenza A virus

<400> SEQUENCE: 31

Met Asp Ser Asn Thr Val Ser Ser Phe Gln Asp Ile Leu Leu Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Ile Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120


<210> SEQ ID NO 32
<211> LENGTH: 237
<212> TYPE: PRT
<213> ORGANISM: Influenza A virus

<400> SEQUENCE: 32

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Asp Leu Asp Ile Glu Ala Ala Thr Arg Val Gly Lys Gln Ile
    50                  55                  60

Val Glu Arg Ile Leu Lys Glu Glu Ser Asp Glu Ala Leu Lys Met Thr
65                  70                  75                  80

Met Ala Ser Ala Pro Ala Ser Arg Tyr Leu Thr Asp Met Thr Ile Glu
                85                  90                  95

Glu Leu Ser Arg Asp Trp Phe Met Leu Met Pro Lys Gln Lys Val Glu
            100                 105                 110
```

```
Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Arg Ser Ser Asn Glu
        195                 200                 205

Asn Gly Arg Pro Pro Leu Thr Pro Lys Gln Lys Arg Lys Met Ala Arg
    210                 215                 220

Thr Ile Arg Ser Lys Val Arg Arg Asp Lys Met Ala Asp
225                 230                 235


<210> SEQ ID NO 33
<211> LENGTH: 498
<212> TYPE: PRT
<213> ORGANISM: Influenza A virus

<400> SEQUENCE: 33

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255
```

Ile Phe Leu Ala Arg Ser Ala Leu Ile Leu Arg Gly Ser Val Ala His
260 265 270

Lys Ser Cys Leu Pro Ala Cys Val Tyr Gly Pro Ala Ile Ala Ser Gly
275 280 285

Tyr Asn Phe Glu Lys Glu Gly Tyr Ser Leu Val Gly Ile Asp Pro Phe
290 295 300

Lys Leu Leu Gln Asn Ser Gln Val Tyr Ser Leu Ile Arg Pro Asn Glu
305 310 315 320

Asn Pro Ala His Lys Ser Gln Leu Val Trp Met Ala Cys Asn Ser Ala
325 330 335

Ala Phe Glu Asp Leu Arg Val Leu Ser Phe Ile Arg Gly Thr Lys Val
340 345 350

Ser Pro Arg Gly Lys Leu Ser Thr Arg Gly Val Gln Ile Ala Ser Asn
355 360 365

Glu Asn Met Asp Thr Met Glu Ser Ser Thr Leu Glu Leu Arg Ser Arg
370 375 380

Tyr Trp Ala Ile Arg Thr Arg Ser Gly Gly Asn Thr Asn Gln Gln Arg
385 390 395 400

Ala Ser Ala Gly Gln Ile Ser Val Gln Pro Ala Phe Ser Val Gln Arg
405 410 415

Asn Leu Pro Phe Asp Lys Pro Thr Ile Met Ala Ala Phe Thr Gly Asn
420 425 430

Thr Glu Gly Arg Thr Ser Asp Met Arg Ala Glu Ile Ile Arg Met Met
435 440 445

Glu Gly Ala Lys Pro Glu Glu Met Ser Phe Gln Gly Arg Gly Val Phe
450 455 460

Glu Leu Ser Asp Glu Lys Ala Thr Asn Pro Ile Val Pro Ser Phe Asp
465 470 475 480

Met Ser Asn Glu Gly Ser Tyr Phe Phe Gly Asp Asn Ala Glu Glu Tyr
485 490 495

Asp Asn

<210> SEQ ID NO 34
<211> LENGTH: 469
<212> TYPE: PRT
<213> ORGANISM: Influenza A virus

<400> SEQUENCE: 34

Met Asn Pro Asn Gln Lys Ile Ile Thr Ile Gly Ser Val Ser Leu Thr
1 5 10 15

Ile Ala Thr Val Cys Phe Leu Met Gln Ile Ala Ile Leu Val Thr Thr
20 25 30

Val Thr Leu His Phe Lys Gln His Glu Cys Asp Ser Pro Ala Ser Asn
35 40 45

Gln Val Met Pro Cys Glu Pro Ile Ile Ile Glu Arg Asn Ile Thr Glu
50 55 60

Ile Val Tyr Leu Asn Asn Thr Thr Ile Glu Lys Glu Ile Cys Pro Glu
65 70 75 80

Val Val Glu Tyr Arg Asn Trp Ser Lys Pro Gln Cys Gln Ile Thr Gly
85 90 95

Phe Ala Pro Phe Ser Lys Asp Asn Ser Ile Arg Leu Ser Ala Gly Gly
100 105 110

Asp Ile Trp Val Thr Arg Glu Pro Tyr Val Ser Cys Asp Pro Gly Lys
115 120 125

```
Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Val
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asp
        195                 200                 205

Gly Arg Leu Met Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335

Cys Arg Asn Pro Asn Asn Glu Arg Gly Asn Pro Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asn Asn Trp Ser Gly Tyr Ser Gly Ile Phe Ser Val Glu Gly Lys Arg
                405                 410                 415

Cys Ile Asn Arg Cys Phe Tyr Val Glu Leu Ile Arg Gly Arg Gln Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465


<210> SEQ ID NO 35
<211> LENGTH: 121
<212> TYPE: PRT
<213> ORGANISM: Influenza A virus

<400> SEQUENCE: 35

Met Asp Ser Asn Thr Val Ser Ser Phe Gln Asp Ile Leu Leu Arg Met
1               5                   10                  15

Ser Lys Met Gln Leu Gly Ser Ser Ser Glu Asp Leu Asn Gly Met Ile
```

```
            20                  25                  30

Thr Gln Phe Glu Ser Leu Lys Ile Tyr Arg Asp Ser Leu Gly Glu Ala
        35                  40                  45

Val Met Arg Met Gly Asp Leu His Leu Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Thr Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120


<210> SEQ ID NO 36
<211> LENGTH: 230
<212> TYPE: PRT
<213> ORGANISM: Influenza A virus

<400> SEQUENCE: 36

Met Asp Ser Asn Thr Val Ser Ser Phe Gln Val Asp Cys Phe Leu Trp
1               5                   10                  15

His Ile Arg Lys Gln Val Val Asp Gln Glu Leu Ser Asp Ala Pro Phe
            20                  25                  30

Leu Asp Arg Leu Arg Arg Asp Gln Arg Ser Leu Arg Gly Arg Gly Asn
        35                  40                  45

Thr Leu Gly Leu Asp Ile Lys Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Val Ser Thr Pro Ala Ser Arg Tyr Ile Thr Asp Met Thr Ile Glu
                85                  90                  95

Glu Leu Ser Arg Asn Trp Phe Met Leu Met Pro Lys Gln Lys Val Glu
            100                 105                 110

Gly Pro Leu Cys Ile Arg Met Asp Gln Ala Ile Met Glu Lys Asn Ile
        115                 120                 125

Met Leu Lys Ala Asn Phe Ser Val Ile Phe Asp Arg Leu Glu Thr Ile
    130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Asn Leu Gln Arg Phe Ala Trp Arg Ser Ser Asn Glu
        195                 200                 205

Asn Gly Gly Pro Pro Leu Thr Pro Lys Gln Lys Arg Lys Met Ala Arg
    210                 215                 220

Thr Ala Arg Ser Lys Val
225                 230


<210> SEQ ID NO 37
<211> LENGTH: 566
<212> TYPE: PRT
<213> ORGANISM: Influenza A virus
```

<400> SEQUENCE: 37

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Ser Ile Gly Ser Arg Pro Arg Ile Arg
225                 230                 235                 240

Asp Val Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415
```

```
Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 38
<211> LENGTH: 97
<212> TYPE: PRT
<213> ORGANISM: Influenza A virus

<400> SEQUENCE: 38

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu


<210> SEQ ID NO 39
<211> LENGTH: 252
<212> TYPE: PRT
<213> ORGANISM: Influenza A virus

<400> SEQUENCE: 39

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60
```

-continued

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Lys Ala
85 90 95

Val Lys Leu Tyr Arg Lys Leu Lys Arg Glu Ile Thr Phe His Gly Ala
100 105 110

Lys Glu Ile Ala Leu Ser Tyr Ser Ala Gly Ala Leu Ala Ser Cys Met
115 120 125

Gly Leu Ile Tyr Asn Arg Met Gly Ala Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Val Ala Thr Thr Asn Pro Leu Ile Lys His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Ile Ala Ser Gln
195 200 205

Ala Arg Gln Met Val Gln Ala Met Arg Ala Val Gly Thr His Pro Ser
210 215 220

Ser Ser Thr Gly Leu Arg Asp Asp Leu Leu Glu Asn Leu Gln Thr Tyr
225 230 235 240

Gln Lys Arg Met Gly Val Gln Met Gln Arg Phe Lys
245 250

<210> SEQ ID NO 40
<211> LENGTH: 90
<212> TYPE: PRT
<213> ORGANISM: Influenza A virus

<400> SEQUENCE: 40

Met Glu Gln Glu Gln Asp Thr Pro Trp Thr Gln Ser Thr Glu His Thr
1 5 10 15

Asn Ile Gln Arg Arg Gly Ser Gly Arg Gln Ile Gln Lys Leu Gly His
20 25 30

Pro Asn Ser Thr Gln Leu Met Asp His Tyr Leu Arg Ile Met Ser Gln
35 40 45

Val Asp Met His Lys Gln Thr Val Ser Trp Arg Leu Trp Pro Ser Leu
50 55 60

Lys Asn Pro Thr Gln Val Ser Leu Arg Thr His Ala Leu Lys Gln Trp
65 70 75 80

Lys Ser Phe Asn Lys Gln Gly Trp Thr Asn
85 90

<210> SEQ ID NO 41
<211> LENGTH: 757
<212> TYPE: PRT
<213> ORGANISM: Influenza A virus

<400> SEQUENCE: 41

Met Asp Val Asn Pro Thr Leu Leu Phe Leu Lys Val Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

-continued

```
Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Val Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
```

-continued 465 470 475 480

Lys Ser Tyr Ile Asn Lys Thr Gly Thr Phe Glu Phe Thr Ser Phe Phe
485 490 495

Tyr Arg Tyr Gly Phe Val Ala Asn Phe Ser Met Glu Leu Pro Ser Phe
500 505 510

Gly Val Ser Gly Ile Asn Glu Ser Ala Asp Met Ser Ile Gly Val Thr
515 520 525

Val Ile Lys Asn Asn Met Ile Asn Asn Asp Leu Gly Pro Ala Thr Ala
530 535 540

Gln Met Ala Leu Gln Leu Phe Ile Lys Asp Tyr Arg Tyr Thr Tyr Arg
545 550 555 560

Cys His Arg Gly Asp Thr Gln Ile Gln Thr Arg Arg Ser Phe Glu Leu
565 570 575

Lys Lys Leu Trp Asp Gln Thr Gln Ser Arg Ala Gly Leu Leu Val Ser
580 585 590

Asp Gly Gly Pro Asn Leu Tyr Asn Ile Arg Asn Leu His Ile Pro Glu
595 600 605

Val Cys Leu Lys Trp Glu Leu Met Asp Glu Asn Tyr Arg Gly Arg Leu
610 615 620

Cys Asn Pro Leu Asn Pro Phe Val Ser His Lys Glu Ile Glu Ser Val
625 630 635 640

Asn Asn Ala Val Val Met Pro Ala His Gly Pro Ala Lys Ser Met Glu
645 650 655

Tyr Asp Ala Val Ala Thr Thr His Ser Trp Asn Pro Lys Arg Asn Arg
660 665 670

Ser Ile Leu Asn Thr Ser Gln Arg Gly Ile Leu Glu Asp Glu Gln Met
675 680 685

Tyr Gln Lys Cys Cys Asn Leu Phe Glu Lys Phe Phe Pro Ser Ser Ser
690 695 700

Tyr Arg Arg Pro Ile Gly Ile Ser Ser Met Val Glu Ala Met Val Ser
705 710 715 720

Arg Ala Arg Ile Asp Ala Arg Ile Asp Phe Glu Ser Gly Arg Ile Lys
725 730 735

Lys Glu Glu Phe Ser Glu Ile Met Lys Ile Cys Ser Thr Ile Glu Glu
740 745 750

Leu Arg Arg Gln Lys
755

<210> SEQ ID NO 42
<211> LENGTH: 498
<212> TYPE: PRT
<213> ORGANISM: Influenza A virus

<400> SEQUENCE: 42

Met Ala Ser Gln Gly Thr Lys Arg Ser Tyr Glu Gln Met Glu Thr Asp
1 5 10 15

Gly Asp Arg Gln Asn Ala Thr Glu Ile Arg Ala Ser Val Gly Lys Met
20 25 30

Ile Asp Gly Ile Gly Arg Phe Tyr Ile Gln Met Cys Thr Glu Leu Lys
35 40 45

Leu Ser Asp His Glu Gly Arg Leu Ile Gln Asn Ser Leu Thr Ile Glu
50 55 60

Lys Met Val Leu Ser Ala Phe Asp Glu Arg Arg Asn Lys Tyr Leu Glu
65 70 75 80

-continued

```
Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 43
<211> LENGTH: 469
<212> TYPE: PRT
<213> ORGANISM: Influenza A virus

<400> SEQUENCE: 43

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Met Cys Pro Lys
65                  70                  75                  80

Leu Ala Glu Tyr Arg Asn Trp Ser Lys Pro Gln Cys Asp Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Ile His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
```

-continued

```
    370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465


<210> SEQ ID NO 44
<211> LENGTH: 716
<212> TYPE: PRT
<213> ORGANISM: Influenza A virus

<400> SEQUENCE: 44

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Val Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Asn Thr His
    130                 135                 140

Ile His Ile Phe Ser Phe Thr Gly Glu Glu Ile Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
            180                 185                 190

Gln Ser Glu Arg Gly Glu Glu Thr Ile Glu Glu Lys Phe Glu Ile Ser
        195                 200                 205

Gly Thr Met Arg Arg Leu Ala Asp Gln Ser Leu Pro Pro Lys Phe Ser
    210                 215                 220

Cys Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Lys Thr Thr Pro Arg Pro Ile Lys Leu Pro Asn
            260                 265                 270
```

-continued

```
Gly Pro Pro Cys Tyr Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Ile Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asn Cys
    370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Ile Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Ile Lys Glu Lys Asp Met Thr
        595                 600                 605

Lys Glu Phe Phe Glu Asn Lys Ser Glu Ala Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
```

```
    690                 695                 700

Ser Trp Phe Asn Ser Phe Leu Thr His Ala Leu Lys
705                 710                 715


<210> SEQ ID NO 45
<211> LENGTH: 759
<212> TYPE: PRT
<213> ORGANISM: Influenza A virus

<400> SEQUENCE: 45

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Ala Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350
```

-continued

```
Lys Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Val Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Ser Val Met Gly Met Val Gly Val Leu
    450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Arg Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
                565                 570                 575

Phe Glu Pro Phe Gln Ser Leu Val Pro Lys Ala Ile Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Ile Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 46
<211> LENGTH: 580
<212> TYPE: PRT
<213> ORGANISM: CMV virus

<400> SEQUENCE: 46

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Gly Asp Ile Leu Ala Gln Ala Val Asn His Ala
                85                  90                  95

Gly Ile Asp Ser Ser Ser Thr Gly His Thr Leu Thr Thr His Ser Cys
            100                 105                 110

Ser Val Ser Ser Ala Pro Leu Asn Lys Pro Thr Pro Thr Ser Val Ala
        115                 120                 125

Val Thr Asn Thr Pro Leu Pro Gly Ala Ser Ala Thr Pro Glu Leu Ser
    130                 135                 140

Pro Arg Lys Lys Pro Arg Lys Thr Thr Arg Pro Phe Lys Val Ile Ile
145                 150                 155                 160

Lys Pro Pro Val Pro Pro Ala Pro Ile Met Leu Pro Leu Ile Lys Gln
                165                 170                 175

Glu Asp Ile Lys Pro Glu Pro Asp Phe Thr Ile Gln Tyr Arg Asn Lys
            180                 185                 190

Ile Ile Asp Thr Ala Gly Cys Ile Val Ile Ser Asp Ser Glu Glu Glu
        195                 200                 205

Gln Gly Glu Glu Val Glu Thr Arg Gly Ala Thr Ala Ser Ser Pro Ser
    210                 215                 220

Thr Gly Ser Gly Thr Pro Arg Val Thr Ser Pro Thr His Pro Leu Ser
225                 230                 235                 240

Gln Met Asn His Pro Pro Leu Pro Asp Pro Leu Ala Arg Pro Asp Glu
                245                 250                 255

Asp Ser Ser Ser Ser Ser Ser Ser Ser Cys Ser Ser Ala Ser Asp Ser
            260                 265                 270

Glu Ser Glu Ser Glu Glu Met Lys Cys Ser Ser Gly Gly Gly Ala Ser
        275                 280                 285

Val Thr Ser Ser His His Gly Arg Gly Gly Phe Gly Ser Ala Ala Ser
    290                 295                 300

Ser Ser Leu Leu Ser Cys Gly His Gln Ser Ser Gly Gly Ala Ser Thr
305                 310                 315                 320

Gly Pro Arg Lys Lys Lys Ser Lys Arg Ile Ser Glu Leu Asp Asn Glu
                325                 330                 335

Lys Val Arg Asn Ile Met Lys Asp Lys Asn Thr Pro Phe Cys Thr Pro
            340                 345                 350

Asn Val Gln Thr Arg Arg Gly Arg Val Lys Ile Asp Glu Val Ser Arg
        355                 360                 365

Met Phe Arg Asn Thr Asn Arg Ser Leu Glu Tyr Lys Asn Leu Pro Phe
    370                 375                 380
```

Thr Ile Pro Ser Met His Gln Val Leu Asp Glu Ala Ile Lys Ala Cys
385 390 395 400

Lys Thr Met Gln Val Asn Asn Lys Gly Ile Gln Ile Ile Tyr Thr Arg
405 410 415

Asn His Glu Val Lys Ser Glu Val Asp Ala Val Arg Cys Arg Leu Gly
420 425 430

Thr Met Cys Asn Leu Ala Leu Ser Thr Pro Phe Leu Met Glu His Thr
435 440 445

Met Pro Val Thr His Pro Pro Glu Val Ala Gln Arg Thr Ala Asp Ala
450 455 460

Cys Asn Glu Gly Val Lys Ala Ala Trp Ser Leu Lys Glu Leu His Thr
465 470 475 480

His Gln Leu Cys Pro Arg Ser Ser Asp Tyr Arg Asn Met Ile Ile His
485 490 495

Ala Ala Thr Pro Val Asp Leu Leu Gly Ala Leu Asn Leu Cys Leu Pro
500 505 510

Leu Met Gln Lys Phe Pro Lys Gln Val Met Val Arg Ile Phe Ser Thr
515 520 525

Asn Gln Gly Gly Phe Met Leu Pro Ile Tyr Glu Thr Ala Ala Lys Ala
530 535 540

Tyr Ala Val Gly Gln Phe Glu Gln Pro Thr Glu Thr Pro Pro Glu Asp
545 550 555 560

Leu Asp Thr Leu Ser Leu Ala Ile Glu Ala Ala Ile Gln Asp Leu Arg
565 570 575

Asn Lys Ser Gln
580

<210> SEQ ID NO 47
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 47

Arg Arg Gly Tyr Ile Pro Leu Val Gly Ala Pro Leu Gly Asx Gly Arg
1 5 10 15

Val Ala Arg Ala Leu Ala His Gly Val Arg Val
20 25

<210> SEQ ID NO 48
<211> LENGTH: 25
<212> TYPE: PRT
<213> ORGANISM: Artificial
<220> FEATURE:
<223> OTHER INFORMATION: Artificial peptide sequence derived from antigen

<400> SEQUENCE: 48

Arg Gly Tyr Ile Pro Leu Val Gly Ala Pro Leu Gly Arg Arg Val Ala
1 5 10 15

Arg Ala Leu Ala His Gly Val Arg Val
20 25

<210> SEQ ID NO 49
<211> LENGTH: 27
<212> TYPE: PRT
<213> ORGANISM: Artificial
<220> FEATURE:

<223> OTHER INFORMATION: Artificial peptide sequence derived from
antigen

<400> SEQUENCE: 49

Arg Gly Tyr Ile Pro Leu Val Gly Ala Pro Leu Gly Arg Arg Arg Val
1 5 10 15

Ala Arg Ala Leu Ala His Gly Val Arg Val Arg
20 25

<210> SEQ ID NO 50
<211> LENGTH: 26
<212> TYPE: PRT
<213> ORGANISM: Artificial
<220> FEATURE:
<223> OTHER INFORMATION: Artificial peptide sequence derived from
antigen

<400> SEQUENCE: 50

Arg Arg Gly Tyr Ile Pro Leu Val Gly Ala Pro Leu Gly Arg Arg Val
1 5 10 15

Ala Arg Ala Leu Ala His Gly Val Arg Val
20 25

<210> SEQ ID NO 51
<211> LENGTH: 27
<212> TYPE: PRT
<213> ORGANISM: Artificial
<220> FEATURE:
<223> OTHER INFORMATION: Artificial peptide sequence derived from
antigen

<400> SEQUENCE: 51

Arg Arg Gly Tyr Ile Pro Leu Val Gly Ala Pro Leu Gly Arg Arg Arg
1 5 10 15

Val Ala Arg Ala Leu Ala His Gly Val Arg Val
20 25

<210> SEQ ID NO 52
<211> LENGTH: 26
<212> TYPE: PRT
<213> ORGANISM: Artificial
<220> FEATURE:
<223> OTHER INFORMATION: Artificial peptide sequence derived from
antigen

<400> SEQUENCE: 52

Asx Arg Gly Tyr Ile Pro Leu Val Gly Ala Pro Leu Gly Arg Arg Val
1 5 10 15

Ala Arg Ala Leu Ala His Gly Val Arg Val
20 25

<210> SEQ ID NO 53
<211> LENGTH: 27
<212> TYPE: PRT
<213> ORGANISM: Artificial
<220> FEATURE:
<223> OTHER INFORMATION: Artificial peptide sequence derived from
antigen

<400> SEQUENCE: 53

Arg Arg Arg Gly Tyr Ile Pro Leu Val Gly Ala Pro Leu Gly Asx Arg
1 5 10 15

Val Ala Arg Ala Leu Ala His Gly Val Arg Val
20 25

<210> SEQ ID NO 54
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 54

```
Arg Gly Tyr Ile Pro Leu Val Gly Ala Pro Leu Gly Lys Lys Lys Val
1               5                   10                  15

Ala Arg Ala Leu Ala His Gly Val Arg Val
            20                  25
```

<210> SEQ ID NO 55
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 55

```
Arg Gly Tyr Ile Pro Leu Val Gly Ala Pro Leu Gly Arg Arg Arg Val
1               5                   10                  15

Ala Arg Ala Leu Ala His Gly Val Arg Val
            20                  25
```

<210> SEQ ID NO 56
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 56

```
Lys Lys Gly Tyr Ile Pro Leu Val Gly Ala Pro Leu Gly Lys Lys Val
1               5                   10                  15

Ala Arg Ala Leu Ala His Gly Val Arg Val
            20                  25
```

<210> SEQ ID NO 57
<211> LENGTH: 25
<212> TYPE: PRT
<213> ORGANISM: Artificial
<220> FEATURE:
<223> OTHER INFORMATION: Artificial peptide sequence derived from antigen

<400> SEQUENCE: 57

```
Trp Gly Tyr Ile Pro Leu Val Gly Ala Pro Leu Gly Arg Arg Val Ala
1               5                   10                  15

Arg Ala Leu Ala His Gly Val Arg Val
            20                  25
```

<210> SEQ ID NO 58
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 58

```
Trp Trp Gly Tyr Ile Pro Leu Val Gly Ala Pro Leu Gly Arg Arg Val
1               5                   10                  15

Ala Arg Ala Leu Ala His Gly Val Arg Val
            20                  25


<210> SEQ ID NO 59
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 59

Glu Glu Gly Tyr Ile Pro Leu Val Gly Ala Pro Leu Gly Glu Glu Val
1               5                   10                  15

Ala Arg Ala Leu Ala His Gly Val Arg Val
            20                  25


<210> SEQ ID NO 60
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 60

Gly Gly Gly Tyr Ile Pro Leu Val Gly Ala Pro Leu Gly Gly Gly Val
1               5                   10                  15

Ala Arg Ala Leu Ala His Gly Val Arg Val
            20                  25


<210> SEQ ID NO 61
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 61

Glu Glu Gly Tyr Ile Pro Leu Val Gly Ala Pro Leu Gly Arg Arg Val
1               5                   10                  15

Ala Arg Ala Leu Ala His Gly Val Arg Val
            20                  25


<210> SEQ ID NO 62
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 62

Arg Arg Gly Tyr Ile Pro Leu Val Gly Ala Pro Leu Gly Leu Arg Arg
1               5                   10                  15

Val Ala Arg Ala Leu Ala His Gly Val Arg Val
            20                  25


<210> SEQ ID NO 63
<211> LENGTH: 26
<212> TYPE: PRT
<213> ORGANISM: Artificial
```

```
<220> FEATURE:
<223> OTHER INFORMATION: Artificial peptide sequence derived from
      antigen

<400> SEQUENCE: 63

Trp Trp Gly Tyr Ile Pro Leu Val Gly Ala Pro Leu Gly Arg Arg Val
1               5                   10                  15

Ala Arg Ala Leu Ala His Gly Val Arg Val
            20                  25


<210> SEQ ID NO 64
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 64

Trp Trp Gly Tyr Ile Pro Leu Val Gly Ala Pro Leu Gly Arg Arg Arg
1               5                   10                  15

Val Ala Arg Ala Leu Ala His Gly Val Arg Val
            20                  25


<210> SEQ ID NO 65
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 65

Trp Trp Gly Tyr Ile Pro Leu Val Gly Ala Pro Leu Gly Arg Val Ala
1               5                   10                  15

Arg Ala Leu Ala His Gly Val Arg Val
            20                  25


<210> SEQ ID NO 66
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 66

Arg Gly Tyr Ile Pro Leu Val Gly Ala Pro Leu Gly Arg Arg Val Ala
1               5                   10                  15

Arg Ala Leu Ala His Gly Val Arg Val
            20                  25


<210> SEQ ID NO 67
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 67

Arg Arg Gly Tyr Leu Pro Ala Val Gly Ala Pro Ile Gly Asx Arg Val
1               5                   10                  15

Ile Arg Val Ile Ala His Gly Leu Arg Leu
            20                  25
```

```
<210> SEQ ID NO 68
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 68

Arg Arg Gly Tyr Ile Pro Leu Val Gly Ala Pro Leu Gly Asx Arg Val
1               5                   10                  15

Ala Arg Ala Leu Ala His Gly Val Arg Val
            20                  25


<210> SEQ ID NO 69
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 69

Gly Tyr Ile Pro Leu Val Gly Ala Pro Leu Gly Gly Val Ala Arg Ala
1               5                   10                  15

Leu Ala His Gly Val Arg Val
            20


<210> SEQ ID NO 70
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 70

Trp Trp Gly Tyr Leu Pro Ala Val Gly Ala Pro Ile Arg Arg Val Ile
1               5                   10                  15

Arg Val Ile Ala His Gly Leu Arg Leu
            20                  25


<210> SEQ ID NO 71
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 71

Gly Tyr Ile Pro Leu Val Gly Ala Pro Leu Gly Gly Val Ala Arg Ala
1               5                   10                  15

Leu Ala His Gly Val Arg Val
            20


<210> SEQ ID NO 72
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 72
```

```
Arg Arg Gly Tyr Ile Pro Leu Val Gly Ala Pro Leu Gly Asx Gly Arg
1               5                   10                  15

Val Ala Arg Ala Leu Ala His Gly Val Arg Val
            20                  25


<210> SEQ ID NO 73
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 73

Arg Gly Tyr Ile Pro Leu Val Gly Ala Pro Leu Gly Arg Arg Val Ala
1               5                   10                  15

Arg Ala Leu Ala His Gly Val Arg Val
            20                  25


<210> SEQ ID NO 74
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 74

Arg Gly Tyr Ile Pro Leu Val Gly Ala Pro Leu Gly Arg Arg Arg Val
1               5                   10                  15

Ala Arg Ala Leu Ala His Gly Val Arg Val
            20                  25


<210> SEQ ID NO 75
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 75

Arg Arg Gly Tyr Ile Pro Leu Val Gly Ala Pro Leu Gly Arg Arg Val
1               5                   10                  15

Ala Arg Ala Leu Ala His Gly Val Arg Val
            20                  25


<210> SEQ ID NO 76
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 76

Arg Arg Gly Tyr Ile Pro Leu Val Gly Ala Pro Leu Gly Arg Arg Arg
1               5                   10                  15

Val Ala Arg Ala Leu Ala His Gly Val Arg Val
            20                  25


<210> SEQ ID NO 77
<211> LENGTH: 26
<212> TYPE: PRT
```

<213> ORGANISM: Artificial
<220> FEATURE:
<223> OTHER INFORMATION: Artificial peptide sequence derived from antigen

<400> SEQUENCE: 77

Asx Arg Gly Tyr Ile Pro Leu Val Gly Ala Pro Leu Gly Arg Arg Val
1 5 10 15

Ala Arg Ala Leu Ala His Gly Val Arg Val
20 25

<210> SEQ ID NO 78
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 78

Arg Arg Arg Gly Tyr Ile Pro Leu Val Gly Ala Pro Leu Gly Asx Arg
1 5 10 15

Val Ala Arg Ala Leu Ala His Gly Val Arg Val
20 25

<210> SEQ ID NO 79
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 79

Arg Gly Tyr Ile Pro Leu Val Gly Ala Pro Leu Gly Lys Lys Lys Val
1 5 10 15

Ala Arg Ala Leu Ala His Gly Val Arg Val
20 25

<210> SEQ ID NO 80
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 80

Arg Gly Tyr Ile Pro Leu Val Gly Ala Pro Leu Gly Arg Arg Arg Val
1 5 10 15

Ala Arg Ala Leu Ala His Gly Val Arg Val
20 25

<210> SEQ ID NO 81
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 81

Lys Lys Gly Tyr Ile Pro Leu Val Gly Ala Pro Leu Gly Lys Lys Val
1 5 10 15

Ala Arg Ala Leu Ala His Gly Val Arg Val 20 25

<210> SEQ ID NO 82
<211> LENGTH: 25
<212> TYPE: PRT
<213> ORGANISM: Artificial
<220> FEATURE:
<223> OTHER INFORMATION: Artificial peptide sequence derived from antigen

<400> SEQUENCE: 82

Trp Gly Tyr Ile Pro Leu Val Gly Ala Pro Leu Gly Arg Arg Val Ala
1 5 10 15

Arg Ala Leu Ala His Gly Val Arg Val
20 25

<210> SEQ ID NO 83
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 83

Trp Trp Gly Tyr Ile Pro Leu Val Gly Ala Pro Leu Gly Arg Arg Val
1 5 10 15

Ala Arg Ala Leu Ala His Gly Val Arg Val
20 25

<210> SEQ ID NO 84
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 84

Arg Arg Gly Tyr Ile Pro Leu Val Gly Ala Pro Leu Gly Leu Arg Arg
1 5 10 15

Val Ala Arg Ala Leu Ala His Gly Val Arg Val
20 25

<210> SEQ ID NO 85
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 85

Arg Arg Asn Tyr Val Thr Gly Asn Ile Pro Gly Asx Arg Gly Ile Thr
1 5 10 15

Phe Ser Ile Phe Leu Ile Val Ser
20

<210> SEQ ID NO 86
<211> LENGTH: 23
<212> TYPE: PRT
<213> ORGANISM: Artificial
<220> FEATURE:
<223> OTHER INFORMATION: Artificial peptide sequence derived from antigen

<400> SEQUENCE: 86

Trp Trp Asn Tyr Ala Thr Gly Asn Leu Pro Gly Arg Arg Cys Ser Phe
1 5 10 15

Ser Ile Phe Leu Leu Ala Leu
20

<210> SEQ ID NO 87
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 87

Trp Trp Asn Tyr Val Thr Gly Asn Ile Pro Gly Asx Arg Gly Ile Thr
1 5 10 15

Phe Ser Ile Phe Leu Ile Val Ser
20

<210> SEQ ID NO 88
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 88

Trp Trp Asn Tyr Val Thr Gly Asn Ile Pro Gly Arg Arg Gly Ile Thr
1 5 10 15

Phe Ser Ile Phe Leu Ile Val Ser
20

<210> SEQ ID NO 89
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 89

Arg Arg Asn Tyr Ala Thr Gly Asn Leu Pro Gly Arg Arg Gly Cys Ser
1 5 10 15

Phe Ser Ile Phe Leu Leu Ala Leu
20

<210> SEQ ID NO 90
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 90

Arg Arg Val Thr Gly Asn Ile Pro Gly Ser Thr Tyr Ser Gly Asx Arg
1 5 10 15

Gly Ile Thr Phe Ser Ile Tyr Leu Ile Val Ser
20 25

<210> SEQ ID NO 91
<211> LENGTH: 27

<212> TYPE: PRT
<213> ORGANISM: Artificial
<220> FEATURE:
<223> OTHER INFORMATION: Artificial peptide sequence derived from antigen

<400> SEQUENCE: 91

Arg Arg Ile Arg Asn Leu Gly Arg Val Ile Glu Thr Leu Thr Gly Asx
1               5                   10                  15

Arg Leu Glx Gly Tyr Ile Pro Leu Ile Gly Ala
            20                  25

<210> SEQ ID NO 92
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 92

Arg Arg Ser Arg Asn Leu Gly Lys Val Ile Asp Thr Leu Thr Cys Asx
1               5                   10                  15

Arg Leu Met Gly Tyr Ile Pro Leu Val Gly Ala
            20                  25

<210> SEQ ID NO 93
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 93

Ser Arg Asn Leu Gly Lys Val Ile Asp Thr Leu Thr Cys Gly Phe Ala
1               5                   10                  15

Asp Leu Met Gly Tyr Ile Pro Leu Val Gly Ala
            20                  25

<210> SEQ ID NO 94
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 94

Trp Trp Ile Arg Asn Leu Gly Arg Val Ile Glu Thr Leu Thr Arg Arg
1               5                   10                  15

Leu Glx Gly Tyr Ile Pro Leu Ile Gly Ala
            20                  25

<210> SEQ ID NO 95
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 95

Trp Trp Ser Arg Asn Leu Gly Lys Val Ile Asp Thr Leu Thr Cys Arg
1               5                   10                  15

```
Arg Leu Met Gly Tyr Ile Pro Leu Val Gly Ala
            20                  25


<210> SEQ ID NO 96
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 96

Arg Arg Gly Gly Gly Gln Ile Ile Gly Gly Asn Tyr Leu Ile Pro Arg
1               5                   10                  15

Asx Pro Asx Ile Gly Val Arg Ala Thr Asx
            20                  25


<210> SEQ ID NO 97
<211> LENGTH: 25
<212> TYPE: PRT
<213> ORGANISM: Artificial
<220> FEATURE:
<223> OTHER INFORMATION: Artificial peptide sequence derived from
      antigen

<400> SEQUENCE: 97

Gly Gly Gly Gln Ile Val Gly Gly Val Tyr Leu Leu Pro Arg Arg Gly
1               5                   10                  15

Pro Arg Leu Gly Val Arg Ala Thr Arg
            20                  25


<210> SEQ ID NO 98
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 98

Arg Arg Gly Gly Gly Gln Ile Val Gly Gly Val Tyr Leu Leu Pro Arg
1               5                   10                  15

Arg Gly Pro Arg Leu Gly Val Arg Ala Thr Arg
            20                  25


<210> SEQ ID NO 99
<211> LENGTH: 26
<212> TYPE: PRT
<213> ORGANISM: Artificial
<220> FEATURE:
<223> OTHER INFORMATION: Artificial peptide sequence derived from
      antigen

<400> SEQUENCE: 99

Trp Trp Gly Gly Gly Gln Ile Val Gly Gly Val Tyr Leu Leu Pro Arg
1               5                   10                  15

Arg Gly Pro Arg Leu Gly Val Arg Ala Thr
            20                  25


<210> SEQ ID NO 100
<211> LENGTH: 21
<212> TYPE: PRT
<213> ORGANISM: Artificial
<220> FEATURE:
<223> OTHER INFORMATION: Artificial peptide sequence derived from
      antigen
```

<400> SEQUENCE: 100

Asx Arg Leu Ile Phe Leu Ala Arg Ser Ala Leu Ile Val Arg Gly Ser
1 5 10 15

Val Ala His Lys Ser
20

<210> SEQ ID NO 101
<211> LENGTH: 21
<212> TYPE: PRT
<213> ORGANISM: Artificial
<220> FEATURE:
<223> OTHER INFORMATION: Artificial peptide sequence derived from antigen

<400> SEQUENCE: 101

Glu Asp Leu Ile Phe Leu Ala Arg Ser Ala Leu Ile Leu Arg Gly Ser
1 5 10 15

Val Ala His Lys Ser
20

<210> SEQ ID NO 102
<211> LENGTH: 28
<212> TYPE: PRT
<213> ORGANISM: Artificial
<220> FEATURE:
<223> OTHER INFORMATION: Artificial peptide sequence derived from antigen

<400> SEQUENCE: 102

Asx Arg Leu Ile Phe Leu Ala Arg Ser Ala Leu Ile Leu Asx Gly Arg
1 5 10 15

Ser Ala Leu Ile Leu Arg Gly Ser Val Ala His Lys
20 25

<210> SEQ ID NO 103
<211> LENGTH: 23
<212> TYPE: PRT
<213> ORGANISM: Artificial
<220> FEATURE:
<223> OTHER INFORMATION: Artificial peptide sequence derived from antigen

<400> SEQUENCE: 103

Ser Ala Tyr Glu Arg Met Cys Asn Ile Leu Lys Gly Lys Phe Gln Thr
1 5 10 15

Ala Ala Gln Arg Ala Met Met
20

<210> SEQ ID NO 104
<211> LENGTH: 23
<212> TYPE: PRT
<213> ORGANISM: Artificial
<220> FEATURE:
<223> OTHER INFORMATION: Artificial peptide sequence derived from antigen

<400> SEQUENCE: 104

Ser Ala Tyr Glu Arg Glx Val Asn Ile Leu Lys Gly Lys Phe Gln Thr
1 5 10 15

Ala Ala Gln Arg Ala Val Glx
20

<210> SEQ ID NO 105

-continued

<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 105

Asx Arg Thr Ala Tyr Glu Arg Glx Cys Asn Ile Leu Asx Arg Gly Arg
1 5 10 15

Phe Gln Thr Val Val Gln Asx Ala
20

<210> SEQ ID NO 106
<211> LENGTH: 25
<212> TYPE: PRT
<213> ORGANISM: Artificial
<220> FEATURE:
<223> OTHER INFORMATION: Artificial peptide sequence derived from antigen

<400> SEQUENCE: 106

Asx Arg Ile Ala Tyr Glu Arg Met Cys Asn Ile Leu Leu Asx Arg Gly
1 5 10 15

Lys Phe Gln Thr Ala Ala Gln Arg Ala
20 25

<210> SEQ ID NO 107
<211> LENGTH: 21
<212> TYPE: PRT
<213> ORGANISM: Artificial
<220> FEATURE:
<223> OTHER INFORMATION: Artificial peptide sequence derived from antigen

<400> SEQUENCE: 107

Ile Ala Tyr Glu Arg Met Cys Asn Ile Leu Lys Gly Lys Phe Gln Thr
1 5 10 15

Ala Ala Gln Arg Ala
20

<210> SEQ ID NO 108
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 108

Leu Phe Phe Lys Cys Ile Tyr Arg Leu Phe Lys His Gly Leu Lys Arg
1 5 10 15

Gly Pro Ser Thr Glu Gly Val Pro Glu Ser Met
20 25

<210> SEQ ID NO 109
<211> LENGTH: 30
<212> TYPE: PRT
<213> ORGANISM: Artificial
<220> FEATURE:
<223> OTHER INFORMATION: Artificial peptide sequence derived from antigen

<400> SEQUENCE: 109

Asx Arg Arg Leu Phe Phe Lys Thr Ile Thr Arg Leu Phe Asx His Gly
1 5 10 15

```
Leu Arg Arg Leu Leu Ser Thr Glu Gly Val Pro Asn Ser Glx
            20                  25                  30


<210> SEQ ID NO 110
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 110

Asx Arg Gly Leu Glu Pro Leu Val Ile Ala Gly Ile Leu Ala Arg Arg
1               5                   10                  15

Gly Ser Leu Val Gly Leu Leu His Ile Val Leu
            20                  25


<210> SEQ ID NO 111
<211> LENGTH: 27
<212> TYPE: PRT
<213> ORGANISM: Artificial
<220> FEATURE:
<223> OTHER INFORMATION: Artificial peptide sequence derived from
      antigen

<400> SEQUENCE: 111

Asx Arg Gly Ser Asp Pro Leu Val Val Ala Ala Ser Ile Val Arg Arg
1               5                   10                  15

Ala Ser Ile Val Gly Ile Leu His Leu Ile Leu
            20                  25


<210> SEQ ID NO 112
<211> LENGTH: 22
<212> TYPE: PRT
<213> ORGANISM: Artificial
<220> FEATURE:
<223> OTHER INFORMATION: Artificial peptide sequence derived from
      antigen

<400> SEQUENCE: 112

Arg Asn Leu Val Pro Met Val Ala Thr Val Arg Arg Asn Leu Val Pro
1               5                   10                  15

Met Val Ala Thr Val Asx
            20


<210> SEQ ID NO 113
<211> LENGTH: 23
<212> TYPE: PRT
<213> ORGANISM: Artificial
<220> FEATURE:
<223> OTHER INFORMATION: Artificial peptide sequence derived from
      antigen

<400> SEQUENCE: 113

Arg Asn Leu Val Pro Met Val Ala Thr Val Asx Arg Arg Asn Leu Val
1               5                   10                  15

Pro Met Val Ala Thr Val Asx
            20


<210> SEQ ID NO 114
<211> LENGTH: 22
<212> TYPE: PRT
<213> ORGANISM: Artificial
<220> FEATURE:
<223> OTHER INFORMATION: Artificial peptide sequence derived from
```

antigen

<400> SEQUENCE: 114

Arg Asn Ile Val Pro Glx Val Val Thr Ala Arg Arg Asn Ile Val Pro
1 5 10 15

Glx Val Val Thr Ala Asx
20

<210> SEQ ID NO 115
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 115

Pro Glu Val Ile Pro Met Phe Ser Ala Leu Ser Glu Gly Ala Thr Pro
1 5 10 15

Gln Asp Leu Asn Thr Met Leu Asn
20

<210> SEQ ID NO 116
<211> LENGTH: 27
<212> TYPE: PRT
<213> ORGANISM: Artificial
<220> FEATURE:
<223> OTHER INFORMATION: Artificial peptide sequence derived from antigen
<220> FEATURE:
<221> NAME/KEY: misc_feature
<222> LOCATION: (6)..(6)
<223> OTHER INFORMATION: Xaa can be any naturally occurring amino acid

<400> SEQUENCE: 116

Arg Phe Ile Ile Pro Xaa Phe Thr Ala Leu Ser Gly Gly Arg Arg Ala
1 5 10 15

Leu Leu Tyr Gly Ala Thr Pro Tyr Ala Ile Gly
20 25

<210> SEQ ID NO 117
<211> LENGTH: 20
<212> TYPE: PRT
<213> ORGANISM: Artificial
<220> FEATURE:
<223> OTHER INFORMATION: Artificial peptide sequence derived from antigen

<400> SEQUENCE: 117

Lys Ala Leu Gly Pro Ala Ala Thr Leu Glu Glu Met Met Thr Ala Cys
1 5 10 15

Gln Gly Val Gly
20

<210> SEQ ID NO 118
<211> LENGTH: 21
<212> TYPE: PRT
<213> ORGANISM: Artificial
<220> FEATURE:
<223> OTHER INFORMATION: Artificial peptide sequence derived from antigen

<400> SEQUENCE: 118

Arg Arg Gly Pro Val Val His Leu Thr Leu Arg Arg Arg Gly Gln Ala
1 5 10 15

Gly Asp Asp Phe Ser
20

<210> SEQ ID NO 119
<211> LENGTH: 21
<212> TYPE: PRT
<213> ORGANISM: Artificial
<220> FEATURE:
<223> OTHER INFORMATION: Artificial peptide sequence derived from antigen

<400> SEQUENCE: 119

Arg Arg Gly Pro Val Val His Leu Thr Leu Arg Arg Arg Gly Gln Ala
1 5 10 15

Gly Asp Asp Phe Ser
20

<210> SEQ ID NO 120
<211> LENGTH: 22
<212> TYPE: PRT
<213> ORGANISM: Artificial
<220> FEATURE:
<223> OTHER INFORMATION: Artificial peptide sequence derived from antigen

<400> SEQUENCE: 120

Arg Arg Gly Pro Val Val His Leu Thr Leu Arg Gly Arg Arg Gly Gln
1 5 10 15

Ala Gly Asp Asp Phe Ser
20

<210> SEQ ID NO 121
<211> LENGTH: 26
<212> TYPE: PRT
<213> ORGANISM: Artificial
<220> FEATURE:
<223> OTHER INFORMATION: Artificial peptide sequence derived from antigen

<400> SEQUENCE: 121

Arg Arg Leu Glu Cys Val Tyr Cys Lys Gln Gln Leu Leu Arg Arg Glu
1 5 10 15

Val Tyr Asp Phe Ala Phe Arg Asp Leu Cys
20 25

<210> SEQ ID NO 122
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 122

Arg Arg Gly Val Tyr Asp Phe Ala Phe Arg Asp Leu Cys Arg Arg Gly
1 5 10 15

Phe Ala Phe Arg Asp Leu Cys Ile Val Tyr Arg
20 25

<210> SEQ ID NO 123
<211> LENGTH: 27
<212> TYPE: PRT
<213> ORGANISM: Artificial
<220> FEATURE:
<223> OTHER INFORMATION: Artificial peptide sequence derived from antigen

<400> SEQUENCE: 123

Arg Arg Gly Val Phe Asp Tyr Ala Phe Arg Asp Ile Asn Arg Arg Gly
1 5 10 15

Phe Ala Tyr Arg Asp Ile Asn Leu Ala Tyr Arg
20 25

<210> SEQ ID NO 124
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 124

Arg Arg Gly Ala Thr Pro Val Asp Leu Leu Gly Ala Arg Arg Gly Ala
1 5 10 15

Leu Asn Leu Cys Leu Pro Met Arg
20

<210> SEQ ID NO 125
<211> LENGTH: 24
<212> TYPE: PRT
<213> ORGANISM: Artificial
<220> FEATURE:
<223> OTHER INFORMATION: Artificial peptide sequence derived from antigen

<400> SEQUENCE: 125

Arg Arg Gly Val Thr Pro Ala Gly Leu Ile Gly Val Arg Arg Gly Ala
1 5 10 15

Leu Gln Ile Asx Leu Pro Leu Arg
20

<210> SEQ ID NO 126
<211> LENGTH: 98
<212> TYPE: PRT
<213> ORGANISM: Human papillomavirus type 16

<400> SEQUENCE: 126

Met His Gly Asp Thr Pro Thr Leu His Glu Tyr Met Leu Asp Leu Gln
1 5 10 15

Pro Glu Thr Thr Asp Leu Tyr Cys Tyr Glu Gln Leu Asn Asp Ser Ser
20 25 30

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

Leu Arg Leu Cys Val Gln Ser Thr His Val Asp Ile Arg Thr Leu Glu
65 70 75 80

Asp Leu Leu Met Gly Thr Leu Gly Ile Val Cys Pro Ile Cys Ser Gln
85 90 95

Lys Pro

<210> SEQ ID NO 127
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 127

Gly Tyr Ile Pro Leu Val Gly Ala Pro Leu Gly
1 5 10

<210> SEQ ID NO 128
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 128

Gly Tyr Leu Pro Ala Val Gly Ala Pro Ile Gly
1 5 10

<210> SEQ ID NO 129
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 129

Gly Tyr Leu Pro Ala Val Gly Ala Pro Ile
1 5 10

<210> SEQ ID NO 130
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 130

Asn Tyr Val Thr Gly Asn Ile Pro Gly
1 5

<210> SEQ ID NO 131
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 131

Asn Tyr Ala Thr Gly Asn Leu Pro Gly
1 5

<210> SEQ ID NO 132
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 132

Asn Tyr Ala Thr Gly Asn Leu Pro Gly
1 5

<210> SEQ ID NO 133
<211> LENGTH: 11

```
<212> TYPE: PRT
<213> ORGANISM: Artificial
<220> FEATURE:
<223> OTHER INFORMATION: Artificial peptide sequence derived from
      antigen

<400> SEQUENCE: 133

Val Thr Gly Asn Ile Pro Gly Ser Thr Tyr Ser
1               5                   10


<210> SEQ ID NO 134
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 134

Ile Arg Asn Leu Gly Arg Val Ile Glu Thr Leu Thr Gly
1               5                   10


<210> SEQ ID NO 135
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 135

Ser Arg Asn Leu Gly Lys Val Ile Asp Thr Leu Thr Cys
1               5                   10


<210> SEQ ID NO 136
<211> LENGTH: 12
<212> TYPE: PRT
<213> ORGANISM: Artificial
<220> FEATURE:
<223> OTHER INFORMATION: Artificial peptide sequence derived from
      antigen

<400> SEQUENCE: 136

Ile Arg Asn Leu Gly Arg Val Ile Glu Thr Leu Thr
1               5                   10


<210> SEQ ID NO 137
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 137

Gly Gly Gly Gln Ile Ile Gly Gly Asn Tyr Leu Ile Pro
1               5                   10


<210> SEQ ID NO 138
<211> LENGTH: 13
<212> TYPE: PRT
<213> ORGANISM: Artificial
<220> FEATURE:
<223> OTHER INFORMATION: Artificial peptide sequence derived from
      antigen

<400> SEQUENCE: 138

Gly Gly Gly Gln Ile Val Gly Gly Val Tyr Leu Leu Pro
```

1 5 10

<210> SEQ ID NO 139
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 139

Leu Ile Phe Leu Ala Arg Ser Ala Leu Ile Val
1 5 10

<210> SEQ ID NO 140
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 140

Leu Ile Phe Leu Ala Arg Ser Ala Leu Ile Leu
1 5 10

<210> SEQ ID NO 141
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 141

Leu Ile Phe Leu Ala Arg Ser Ala Leu Ile Leu
1 5 10

<210> SEQ ID NO 142
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 142

Ser Ala Tyr Glu Arg Met Cys Asn Ile Leu
1 5 10

<210> SEQ ID NO 143
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 143

Ser Ala Tyr Glu Arg Glx Val Asn Ile Leu
1 5 10

<210> SEQ ID NO 144
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 144

Thr Ala Tyr Glu Arg Glx Cys Asn Ile Leu
1 5 10

<210> SEQ ID NO 145
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 145

Ile Ala Tyr Glu Arg Met Cys Asn Ile Leu
1 5 10

<210> SEQ ID NO 146
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 146

Ile Ala Tyr Glu Arg Met Cys Asn Ile Leu
1 5 10

<210> SEQ ID NO 147
<211> LENGTH: 14
<212> TYPE: PRT
<213> ORGANISM: Artificial
<220> FEATURE:
<223> OTHER INFORMATION: Artificial peptide sequence derived from antigen

<400> SEQUENCE: 147

Leu Phe Phe Lys Cys Ile Tyr Arg Leu Phe Lys His Gly Leu
1 5 10

<210> SEQ ID NO 148
<211> LENGTH: 14
<212> TYPE: PRT
<213> ORGANISM: Artificial
<220> FEATURE:
<223> OTHER INFORMATION: Artificial peptide sequence derived from antigen

<400> SEQUENCE: 148

Leu Phe Phe Lys Thr Ile Thr Arg Leu Phe Asx His Gly Leu
1 5 10

<210> SEQ ID NO 149
<211> LENGTH: 12
<212> TYPE: PRT
<213> ORGANISM: Artificial
<220> FEATURE:
<223> OTHER INFORMATION: Artificial peptide sequence derived from antigen

<400> SEQUENCE: 149

Gly Leu Glu Pro Leu Val Ile Ala Gly Ile Leu Ala
1 5 10

<210> SEQ ID NO 150

<211> LENGTH: 12
<212> TYPE: PRT
<213> ORGANISM: Artificial
<220> FEATURE:
<223> OTHER INFORMATION: Artificial peptide sequence derived from antigen

<400> SEQUENCE: 150

Gly Ser Asp Pro Leu Val Val Ala Ala Ser Ile Val
1 5 10

<210> SEQ ID NO 151
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 151

Asn Leu Val Pro Met Val Ala Thr Val
1 5

<210> SEQ ID NO 152
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 152

Asn Leu Val Pro Met Val Ala Thr Val
1 5

<210> SEQ ID NO 153
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 153

Asn Ile Val Pro Glx Val Val Thr Ala
1 5

<210> SEQ ID NO 154
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 154

Pro Glu Val Ile Pro Met Phe Ser Ala Leu Ser
1 5 10

<210> SEQ ID NO 155
<211> LENGTH: 11
<212> TYPE: PRT
<213> ORGANISM: Artificial
<220> FEATURE:
<223> OTHER INFORMATION: Artificial peptide sequence derived from antigen
<220> FEATURE:
<221> NAME/KEY: misc_feature
<222> LOCATION: (5)..(5)

<223> OTHER INFORMATION: Xaa can be any naturally occurring amino acid

<400> SEQUENCE: 155

Phe Ile Ile Pro Xaa Phe Thr Ala Leu Ser Gly
1 5 10

<210> SEQ ID NO 156
<211> LENGTH: 8
<212> TYPE: PRT
<213> ORGANISM: Artificial
<220> FEATURE:
<223> OTHER INFORMATION: Artificial peptide sequence derived from antigen

<400> SEQUENCE: 156

Ala Leu Gly Pro Ala Ala Thr Leu
1 5

<210> SEQ ID NO 157
<211> LENGTH: 8
<212> TYPE: PRT
<213> ORGANISM: Artificial
<220> FEATURE:
<223> OTHER INFORMATION: Artificial peptide sequence derived from antigen

<400> SEQUENCE: 157

Gly Pro Val Val His Leu Thr Leu
1 5

<210> SEQ ID NO 158
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 158

Leu Glu Cys Val Tyr Cys Lys Gln Gln Leu Leu
1 5 10

<210> SEQ ID NO 159
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 159

Gly Val Tyr Asp Phe Ala Phe Arg Asp Leu Cys
1 5 10

<210> SEQ ID NO 160
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 160

Gly Val Phe Asp Tyr Ala Phe Arg Asp Ile Asn
1 5 10

<210> SEQ ID NO 161
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 161

Gly Ala Thr Pro Val Asp Leu Leu Gly Ala
1 5 10

<210> SEQ ID NO 162
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 162

Gly Val Thr Pro Ala Gly Leu Ile Gly Val
1 5 10

<210> SEQ ID NO 163
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 163

Val Ala Arg Ala Leu Ala His Gly Val Arg Val
1 5 10

<210> SEQ ID NO 164
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 164

Val Ile Arg Val Ile Ala His Gly Leu Arg Leu
1 5 10

<210> SEQ ID NO 165
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 165

Gly Ile Thr Phe Ser Ile Phe Leu Ile Val Ser
1 5 10

<210> SEQ ID NO 166
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 166

Cys Ser Phe Ser Ile Phe Leu Leu Ala Leu
1 5 10

<210> SEQ ID NO 167
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 167

Gly Cys Ser Phe Ser Ile Phe Leu Leu Ala Leu
1 5 10

<210> SEQ ID NO 168
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 168

Gly Ile Thr Phe Ser Ile Tyr Leu Ile Val Ser
1 5 10

<210> SEQ ID NO 169
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 169

Leu Glx Gly Tyr Ile Pro Leu Ile Gly Ala
1 5 10

<210> SEQ ID NO 170
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 170

Leu Met Gly Tyr Ile Pro Leu Val Gly Ala
1 5 10

<210> SEQ ID NO 171
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 171

Leu Glx Gly Tyr Ile Pro Leu Ile Gly Ala
1 5 10

<210> SEQ ID NO 172
<211> LENGTH: 9
<212> TYPE: PRT
<213> ORGANISM: Artificial

<220> FEATURE:
<223> OTHER INFORMATION: Artificial peptide sequence derived from antigen

<400> SEQUENCE: 172

Pro Asx Ile Gly Val Arg Ala Thr Asx
1 5

<210> SEQ ID NO 173
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 173

Gly Pro Arg Leu Gly Val Arg Ala Thr Arg
1 5 10

<210> SEQ ID NO 174
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 174

Gly Pro Arg Leu Gly Val Arg Ala Thr
1 5

<210> SEQ ID NO 175
<211> LENGTH: 8
<212> TYPE: PRT
<213> ORGANISM: Artificial
<220> FEATURE:
<223> OTHER INFORMATION: Artificial peptide sequence derived from antigen

<400> SEQUENCE: 175

Arg Gly Ser Val Ala His Lys Ser
1 5

<210> SEQ ID NO 176
<211> LENGTH: 12
<212> TYPE: PRT
<213> ORGANISM: Artificial
<220> FEATURE:
<223> OTHER INFORMATION: Artificial peptide sequence derived from antigen

<400> SEQUENCE: 176

Ser Ala Leu Ile Leu Arg Gly Ser Val Ala His Lys
1 5 10

<210> SEQ ID NO 177
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 177

Phe Gln Thr Ala Ala Gln Arg Ala Met Met
1 5 10

-continued

<210> SEQ ID NO 178
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 178

Phe Gln Thr Ala Ala Gln Arg Ala Val Glx
1 5 10

<210> SEQ ID NO 179
<211> LENGTH: 8
<212> TYPE: PRT
<213> ORGANISM: Artificial
<220> FEATURE:
<223> OTHER INFORMATION: Artificial peptide sequence derived from antigen

<400> SEQUENCE: 179

Phe Gln Thr Val Val Gln Asx Ala
1 5

<210> SEQ ID NO 180
<211> LENGTH: 8
<212> TYPE: PRT
<213> ORGANISM: Artificial
<220> FEATURE:
<223> OTHER INFORMATION: Artificial peptide sequence derived from antigen

<400> SEQUENCE: 180

Phe Gln Thr Ala Ala Gln Arg Ala
1 5

<210> SEQ ID NO 181
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 181

Gly Pro Ser Thr Glu Gly Val Pro Glu Ser Met
1 5 10

<210> SEQ ID NO 182
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 182

Leu Leu Ser Thr Glu Gly Val Pro Asn Ser Glx
1 5 10

<210> SEQ ID NO 183
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 183

Gly Ser Leu Val Gly Leu Leu His Ile Val Leu
1 5 10

<210> SEQ ID NO 184
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 184

Ala Ser Ile Val Gly Ile Leu His Leu Ile Leu
1 5 10

<210> SEQ ID NO 185
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 185

Asn Leu Val Pro Met Val Ala Thr Val
1 5

<210> SEQ ID NO 186
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 186

Asn Ile Val Pro Glx Val Val Thr Ala
1 5

<210> SEQ ID NO 187
<211> LENGTH: 10
<212> TYPE: PRT
<213> ORGANISM: Artificial
<220> FEATURE:
<223> OTHER INFORMATION: Artificial peptide sequence derived from antigen

<400> SEQUENCE: 187

Thr Pro Gln Asp Leu Asn Thr Met Leu Asn
1 5 10

<210> SEQ ID NO 188
<211> LENGTH: 12
<212> TYPE: PRT
<213> ORGANISM: Artificial
<220> FEATURE:
<223> OTHER INFORMATION: Artificial peptide sequence derived from antigen

<400> SEQUENCE: 188

Ala Leu Leu Tyr Gly Ala Thr Pro Tyr Ala Ile Gly
1 5 10

<210> SEQ ID NO 189
<211> LENGTH: 9
<212> TYPE: PRT

<213> ORGANISM: Artificial
<220> FEATURE:
<223> OTHER INFORMATION: Artificial peptide sequence derived from antigen

<400> SEQUENCE: 189

Met Met Thr Ala Cys Gln Gly Val Gly
1 5

<210> SEQ ID NO 190
<211> LENGTH: 8
<212> TYPE: PRT
<213> ORGANISM: Artificial
<220> FEATURE:
<223> OTHER INFORMATION: Artificial peptide sequence derived from antigen

<400> SEQUENCE: 190

Gly Gln Ala Gly Asp Asp Phe Ser
1 5

<210> SEQ ID NO 191
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 191

Glu Val Tyr Asp Phe Ala Phe Arg Asp Leu Cys
1 5 10

<210> SEQ ID NO 192
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 192

Gly Phe Ala Phe Arg Asp Leu Cys Ile Val Tyr
1 5 10

<210> SEQ ID NO 193
<211> LENGTH: 11
<212> TYPE: PRT
<213> ORGANISM: Artificial
<220> FEATURE:
<223> OTHER INFORMATION: Artificial peptide sequence derived from antigen

<400> SEQUENCE: 193

Gly Phe Ala Tyr Arg Asp Ile Asn Leu Ala Tyr
1 5 10

<210> SEQ ID NO 194
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 194

Gly Ala Leu Asn Leu Cys Leu Pro Met
1 5

<210> SEQ ID NO 195
<211> LENGTH: 9
<212> TYPE: PRT
<213> ORGANISM: Artificial
<220> FEATURE:
<223> OTHER INFORMATION: Artificial peptide sequence derived from antigen

<400> SEQUENCE: 195

Gly Ala Leu Gln Ile Asx Leu Pro Leu
1 5

<210> SEQ ID NO 196
<211> LENGTH: 27
<212> TYPE: PRT
<213> ORGANISM: Artificial Sequence
<220> FEATURE:
<223> OTHER INFORMATION: Artificial peptide sequence derived from antigen

<400> SEQUENCE: 196

Arg Gly Tyr Leu Pro Ala Val Gly Ala Pro Ile Gly Arg Arg Arg Val
1 5 10 15

Ile Arg Val Ile Ala His Gly Leu Arg Leu Arg
20 25

<210> SEQ ID NO 197
<211> LENGTH: 27
<212> TYPE: PRT
<213> ORGANISM: Artificial Sequence
<220> FEATURE:
<223> OTHER INFORMATION: Artificial peptide sequence derived from antigen

<400> SEQUENCE: 197

Arg Arg Ser Arg Asn Leu Gly Lys Val Ile Asp Thr Leu Thr Cys Arg
1 5 10 15

Arg Leu Met Gly Tyr Ile Pro Leu Val Gly Ala
20 25

<210> SEQ ID NO 198
<211> LENGTH: 22
<212> TYPE: PRT
<213> ORGANISM: Artificial Sequence
<220> FEATURE:
<223> OTHER INFORMATION: Artificial peptide sequence derived from antigen

<400> SEQUENCE: 198

Ile Arg Asn Leu Gly Arg Val Ile Glu Thr Leu Thr Leu Glx Gly Tyr
1 5 10 15

Ile Pro Leu Ile Gly Ala
20

<210> SEQ ID NO 199
<211> LENGTH: 49
<212> TYPE: PRT
<213> ORGANISM: Artificial Sequence
<220> FEATURE:
<223> OTHER INFORMATION: Artificial peptide sequence derived from antigen

<400> SEQUENCE: 199

Arg Arg Ile Arg Asn Leu Gly Arg Val Ile Glu Thr Leu Thr Leu Glx
1 5 10 15

-continued

```
Gly Tyr Ile Pro Leu Ile Gly Ala Arg Arg Ile Arg Asn Leu Gly Arg
        20                  25                  30

Val Ile Glu Thr Leu Thr Leu Glx Gly Tyr Ile Pro Leu Ile Gly Ala
    35                  40                  45

Arg
```

PEPTIDE SCAFFOLD DESIGN

FIELD OF THE INVENTION

The present invention relates to novel peptides and methods for treatment, diagnosis and prognosis of virus infections including infections with HCV, HIV, CMV and Influenza. The invention further relates to methods for identifying and providing peptides useful for the treatment and diagnosis.

BACKGROUND OF THE INVENTION

Conventional approaches to vaccine development have implemented either whole replication competent virus which has been attenuated (e.g. Sabin polio vaccine, measles, mumps, rubella (MMR)) or inactivated virions that are not replication competent. On occasions, the inactivated virus vaccines may include split vaccines where the virus particles have been disrupted. Molecular techniques have also been used to develop the subunit vaccine (e.g. hepatitis B vaccine) that consists only of the surface glycoproteins of hepatitis B virus. The inactivated virus vaccines tend to induce primarily antibody responses to the viruses in question, whereas the live attenuated vaccines induce both cell-mediated immunity as well as an antibody response since the vaccine induces a transient infection.

The only disease which has been eliminated by virtue of a successful vaccination campaign is smallpox. A campaign is currently in progress to eradicate polio. Features of virus infections that can be eliminated by vaccination are infections caused by viruses with stable virus antigens (i.e. very low mutation frequency, few subtypes), that lack a reservoir in other animal species, viruses that do not persist in the body once the infection is over and where vaccination leads to long lasting immunity. Viruses such as polio and measles fulfill these criteria whereas viruses such as influenza virus (Flu), HCV, and HIV that vary their protein sequences do not. It is for this reason that new and alternate approaches are required to develop vaccines for these diseases.

Vaccination aims to stimulate the immune response to a specific pathogen in advance of infection. When an individual is exposed to that pathogen, a memory response is triggered which prevents the establishment of infection. Vaccines therefore stimulate the adaptive immune response which unlike innate immunity, is long lived and has memory. There are two major arms to the adaptive immune system. Humoral immunity which involves the development of antibodies that can bind virus particles and certain antibodies that can neutralize infection. Cell mediated immunity that leads to the development of cytotoxic T-cells that kill infected cells exposing viral epitopes in the context of human leukocyte antigen (HLA) class I, in this way eliminating infected cells.

The challenge of providing vaccines suitable for stimulation of the adaptive immune system is that peptide epitopes need to be taken up by the antigen presenting cells.

Several peptides have been demonstrated to translocate across the plasma membrane of eukaryotic cells by a seemingly energy-independent pathway. These peptides are defined as cell-penetrating peptides (CPPs). Cellular delivery using these cell-penetrating peptides offers several advantages over conventional techniques. It is non-invasive, energy-independent, is efficient for a broad range of cell types and can be applied to cells en masse.

Hepatitis means inflammation of the liver which can be caused by a variety of factors including toxins, certain drugs, some diseases, heavy alcohol use, and bacterial and viral infections. Hepatitis is also the name of a family of viral infections that affect the liver; the most common types in the developed world are hepatitis A, hepatitis B, and hepatitis C.

Hepatitis C is a liver disease that results from infection with the hepatitis C virus (HCV). It can range in severity from a mild illness lasting a few weeks to a serious, lifelong illness.

Hepatitis C is spread via blood; the most common form of transmission is through sharing needles or other equipment used to inject drugs. The infection can be either "acute" or "chronic". Acute HCV infection is an asymptomatic, short-term illness that occurs within the first 6 months after someone is exposed to the hepatitis C virus. For most people, acute infection leads to chronic infection, which can result in long-term complications and even death.

HCV is an enveloped positive stranded ribonucleic acid (RNA) virus with a diameter of about 50 nm, belonging to the genus *Hepacivirus* in the family Flaviviridae that replicate in the cytoplasm of infected cells. The only known reservoir for HCV is humans, although the virus has experimentally been transmitted to chimpanzees. The natural targets of HCV are hepatocytes and possibly B-lymphocytes. As of 2008, six different genotypes and more than 100 subtypes of the virus are known. Replication occurs through an RNA-dependent RNA polymerase that lacks a proofreading function, which results in a very high rate of mutations. Rapid mutations in a hypervariable region of the HCV genome coding for the envelope proteins enable the virus to escape immune surveillance by the host. As a consequence, most HCV-infected people proceed to chronic infection.

It is estimated that 170 million people are infected with HCV worldwide, equating to approximately 3% of the global population. There are also approximately 3-4 million people who are infected every year; with an estimated 80% of these newly infected patients progressing to chronic infection.

The 6 genotypes of HCV have different geographical spread. The disease in the early stages is generally asymptomatic; the majority of patients with chronic infection eventually progress to complications such as liver fibrosis and cirrhosis, and, in 1-5% of cases, hepatocellular carcinoma.

HCV is the major cause of non-A, non-B hepatitis worldwide. Acute infection with HCV frequently leads to chronic hepatitis and end-stage cirrhosis. It is estimated that up to 20% of HCV chronic carriers may develop cirrhosis over a time period of about 20 years and that of those with cirrhosis between 1 to 4% is at risk to develop liver carcinoma.

The about 9.6 kb single-stranded RNA genome of the HCV virus comprises a 5'- and 3'-noncoding region (NCRs) and, in between these NCRs a single long open reading frame of about 9 kb encoding an HCV polyprotein of about 3000 amino acids.

HCV polypeptides are produced by translation from the open reading frame and cotranslational proteolytic processing. Structural proteins are derived from the amino-terminal one-fourth of the coding region and include the capsid or Core protein (about 21 kDa), the E1 envelope glycoprotein (about 35 kDa) and the E2 envelope glycoprotein (about 70 kDa, previously called NS1), and p7 (about 7 kDa). The E2 protein can occur with or without a C-terminal fusion of the p7 protein (Shimotohno et al. 1995). An alternative open reading frame in the Core-region has been found which is encoding and expressing a protein of about 17 kDa called F (Frameshift) protein (Xu et al. 2001; Ou & Xu in US Patent Application Publication No. US2002/0076415). In the same region, ORFs for other 14-17 kDa ARFPs (Alternative Reading Frame Proteins), A1 to A4, were discovered and antibodies to at least A1, A2 and A3 were detected in sera of chronically infected patients (Walewski et al. 2001). From the remainder of the HCV coding region, the non-structural HCV proteins are derived which include NS2 (about 23 kDa), NS3 (about 70 kDa), NS4A (about 8 kDa), NS4B (about 27 kDa), NS5A (about 58 kDa) and NS5B (about 68 kDa) (Grakoui et al. 1993).

Influenza remains a significant cause of mortality and morbidity worldwide. The World Health Organisation (WHO) estimates that seasonal epidemics affect 3-5 million people with severe illness annually and result in 250,000-500,000 mortalities. Influenza is caused by viruses in the family Orthomyxoviridae which are negative stranded RNA viruses. The influenza virus exists as three types, A, B and C of which only A is associated with pandemics. Types A viruses are found in both humans and animals, particularly birds but also other mammals such as pigs. Type A viruses are further typed into subtypes according to different kinds and combinations of virus surface proteins. Among many subtypes in 2009 influenza A (H1N1) and A (H3N2) subtypes were circulating among humans. Influenza A and B are included in the seasonal vaccine, whereas influenza C occurs only rarely, and so it is not included in the seasonal vaccine. Type B viruses are human specific and Type C viruses cause a very mild disease. The genomes of Orthomyxoviruses are segmented. Influenza viruses Types A and B have 8 segments whereas type C has seven. Pandemics may arise as a result of re-assortment of gene segments when two different type A viruses infect the same cell. There is no immunity in the population to this novel re-assorted virus. Three pandemics occurred in the twentieth century: "Spanish influenza" in 1918, "Asian influenza" in 1957, and "Hong Kong influenza" in 1968. The 1918 pandemic killed an estimated 40-50 million people worldwide. Subsequent pandemics were much milder, with an estimated 2 million deaths in 1957 and 1 million deaths in 1968. In June 2009 the WHO declared a pandemic from influenza virus H1N1 (swine Influenza) which was declared over in August 2010.

Human papillomaviruses are made up of a group of DNA viruses in the family Papillomaviridae which infect the skin and mucous membranes. Two groups which are derived from more than 100 different identified subtypes are the main cause for clinical concern: those causing warts (both benign and genital warts), and a group of 12 "high risk" subtypes that can result in cervical cancer. This latter group has been attributed as a contributory factor in the development of nearly all types of cervical cancer. Worldwide, cervical cancer remains the second most common malignancy in women, and is a leading cause of cancer-related death for females in developing countries. HPV 16 and 18 have been mainly associated with cervical cancer, however, the virus is also a cause of throat cancer in both men and women. HPV is transmitted through contact and enters the skin through abraisions. An abortive infection, where only the early proteins are expressed is associated with cancer development.

OBJECT OF THE INVENTION

It is an object of embodiments of the invention to provide peptides that may be used as immunogens to stimulate an adaptive immune response in a subject.

In particular, it is an object of embodiments of the invention to provide peptides that may be taken up by antigen presenting cells (macrophages and dendritic cells) such that epitopes within the peptides are correctly processed and presented to T-lymphocytes in order to stimulate an effective immune response.

Further, it is an object of embodiments of the invention to provide peptides that may be used as antigens, to provide immunogenic compositions and methods for inducing an immune response in a subject against an antigen.

SUMMARY OF THE INVENTION

The present invention pertains to a peptide design promoting uptake of peptide epitopes by antigen presenting cells (macrophages and dendritic cells) such that the epitopes can be correctly processed and presented in the context of HLA class I and II to stimulate both CD4+ and CD8+ T-lymphocytes. CD8+ T-lymphocytes with cytotoxic capacity will kill infected cells bearing the epitope of interest. CD4+ T-lymphocyte provide 'help' to sustain effective CD8+ T-lymphocyte responses.

It has been found by the present inventor(s) that peptide constructs—amino acid sequences with a particular pattern or scaffold design—have the ability to effectively penetrate the cell membrane. Accordingly, the peptide constructs according to the present invention may be used to load cells with an immunogenically effective amount of a peptide or fragments of this peptide that can be presented by macrophages and dendritic cells. Accordingly these peptide constructs may elicit a Cytotoxic T-lymphocyte immune (CTL) response and/or a Humoral Immune Response.

So, in a first aspect the present invention relates to an isolated cell-penetrating peptide of not more than 60 amino acids with the following structure $$X^1\text{-}X^2\text{-}X^3\text{-}X^4\text{-}X^5 \quad \text{(formula I)},$$

wherein $X^1$ and $X^3$ independently defines a linear sequence of any 1, 2, 3 or 4 amino acid(s) independently selected from any basic amino acid, citrulline, tryptophan, or a derivative thereof; $X^2$ defines a linear sequence of 8-30 amino acids derived from an antigen; $X^4$ defines a linear sequence of 8-30 amino acids derived from said antigen, said sequence $X^4$ being different from $X^2$; and wherein $X^5$ is any one optional amino acid selected from a basic amino acid, citrulline, tryptophan, or a derivative thereof.

It is to be understood that the amino acid sequence of formula I refers to a peptide sequence in a standard N- to C-terminal direction, wherein the first amino acid mentioned is the N-terminal amino acid that may have an amino (—$NH_2$) group or alternatively an —$NH_3^+$ group. The last amino acid mentioned is the C-terminal that may have a free carboxyl group (—COOH) or a carboxylate group. In some embodiments the N- and/or C-terminal amino acid is modified, such as by N-terminal acetylation or C-terminal amidation. The symbol "-" used in formula I refers to a standard peptide bond, such as a standard peptide bond between $X^1$ and $X^2$ in "$X^1$-$X^2$".

It is further to be understood that the peptides according to the invention primarily are intended for synthetic peptide synthesis. However, the peptides may be longer than 60 amino acids, if the peptides are produced by recombinant means. Accordingly, an alternative first aspect or the present invention relates to an isolated cell-penetrating peptide comprising a peptide sequence with the following structure $$X^1\text{-}X^2\text{-}X^3\text{-}X^4\text{-}X^5 \quad \text{(formula I)},$$

wherein $X^1$ and $X^3$ independently defines a linear sequence of any 1, 2, 3 or 4 amino acid independently selected from any basic amino acid, citrulline, tryptophan, or a derivative thereof; $X^2$ defines a linear sequence of 8-30 amino acids derived from an antigen; $X^4$ defines a linear sequence of 8-30 amino acids derived from said antigen, said sequence $X^4$ being different from $X^2$; and wherein $X^5$ is any one optional amino acid selected from a basic amino acid, citrulline, tryptophan, or a derivative thereof.

In a second aspect the present invention relates to an isolated peptide of not more than 60 amino acids comprising a sequence of $X^2$ and/or $X^4$ as independently defined in any one of table 1 or table 2.

In a third aspect the present invention relates to the use of a peptide comprising a sequence of $X^2$ or $X^4$ as independently defined in any one of table 1 or table 2 for inducing an immune response in a subject.

In a further aspect the present invention relates to an isolated peptide consisting of $X^1$-$X^5$ as defined in any one of table 1 or table 2.

In a further aspect the present invention relates to a dimer peptide comprising two peptide monomers, wherein each peptide monomer is according to the invention.

In a further aspect the present invention relates to a peptide combination comprising two or more peptides according to the invention.

In a further aspect the present invention relates to an isolated nucleic acid or polynucleotide encoding a peptide according to the invention.

In a further aspect the present invention relates to a vector comprising the nucleic acid or polynucleotide encoding a peptide according to the invention.

In a further aspect the present invention relates to a host cell comprising the vector comprising the nucleic acid or polynucleotide encoding a peptide according to the invention.

In a further aspect the present invention relates to an immunogenic composition comprising at least one peptide according to the invention, a dimer peptide comprising two peptides monomers, wherein each peptide monomer is according to the invention, a peptide combination comprising two or more peptide according to the invention, the nucleic acid or polynucleotide encoding a peptide according to the invention, or the vector comprising the nucleic acid or polynucleotide encoding a peptide according to the invention; in combination with a pharmaceutically acceptable diluent or vehicle and optionally an immunological adjuvant.

In a further aspect the present invention relates to a method for inducing an immune response in a subject against an antigen which comprises administration of at least one peptide according to the invention; a dimer peptide comprising two peptides monomers, wherein each peptide monomer is according to the invention; a peptide combination comprising two or more peptide according to the invention; the nucleic acid or polynucleotide encoding a peptide according to the invention; the vector comprising the nucleic acid or polynucleotide encoding a peptide according to the invention; or the composition according to the invention.

In a further aspect the present invention relates to a method for reducing and/or delaying the pathological effects of a virus in a subject infected with said virus, the method comprising administering an effective amount of at least one peptide according to the invention; a dimer peptide comprising two peptides monomers, wherein each peptide monomer is according to the invention; a peptide combination comprising two or more peptide according to the invention; the nucleic acid or polynucleotide encoding a peptide according to the invention; the vector comprising the nucleic acid or polynucleotide encoding a peptide according to the invention; or the composition according to the invention.

In a further aspect the present invention relates to a peptide according to the invention for use as a medicament.

In a further aspect the present invention relates to a peptide according to the invention for treating the pathological effects of a virus in a subject infected with said virus.

DETAILED DISCLOSURE OF THE INVENTION

Definitions

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

"HIV" generally denotes human immunodeficiency virus I.

"HIV disease" is composed of several stages including the acute HIV infection which often manifests itself as an influenza-like infection and the early and medium stage symptomatic disease, which has several non-characteristic symptoms such as skin rashes, fatigue, night sweats, slight weight loss, mouth ulcers, and fungal skin and nail infections. Most HIV infected will experience mild symptoms such as these before developing more serious illnesses. It is generally believed that it takes five to seven years for the first mild symptoms to appear. As HIV disease progresses, some individuals may become quite ill even if they have not yet been diagnosed with AIDS (see below), the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition which progressively reduces the effectiveness of the immune system and leaves individuals susceptible to opportunistic infections and tumors.

The term "cell-penetrating peptide" as used herein refers to any peptide with the capability to translocate across the plasma membrane into either cytoplasmic and/or nuclear compartments of eukaryotic and/or prokaryotic cells, such as into cytoplasm, nucleus, lysosome, endoplasmatic reticulum, golgi apparatus, mitocondria and/or chloroplast, seemingly energy-independently. This capability to translocate across the plasma membrane of a "cell-penetrating peptide" according to the invention may be non-invasive, energy-independent, non-saturable, and/or receptor independent. In one embodiment the term "cell-penetrating peptide" refers to a peptide, which is demonstrated to translocate across a plasma membrane as determined by the assay in example 1. It is to be understood that a cell-penetrating peptide according to the present invention may be translocated across the membrane with the sequence complete and intact, or alternatively partly degraded, but in a form where the antigens contained within this peptide is able to be presented within the cell to stimulate an immune response. Accordingly, a cell-penetrating peptide according to the present invention is a peptide that may be demonstrated to translocate across a plasma membrane as determined by the assay in example 1 and be demonstrated to stimulate an effective immune response.

The term "derived from an antigen" when in reference to a peptide derived from a source (such as a virus etc.) as used herein is intended to refer to a peptide which has been obtained (e.g., isolated, purified, etc.) from the source. Preferably, the peptide may be genetically engineered and/or chemically synthesized to be essentially identical to the native peptide of the source. The term includes the use of variants of known native peptide sequences, such as peptide sequences, where 1, 2, 3, 4, 5, 6, 7, 8, 9, or 10 amino acids of the native peptide sequence have been substituted with any other amino acid, such as conservative substitutions. Alternatively, 1, 2, 3, 4, 5, 6, 7, 8, 9, or 10 amino acids have been removed or added to the native peptide sequence. Accordingly, in some embodiments, the peptides according to the present invention comprises the sequences $X^2$ and/or $X^4$, that is defined as a sequence of 8-30 amino acids, such as 8-20 amino acids derived from an antigen, wherein the peptide sequence of the antigen comprises 1, 2, 3, 4, 5, 6, 7, 8, 9, or 10 substitutions, additions or deletions relative to the antigen, such as the addition of an arginine in the N- or C-terminal of the amino acid sequence of $X^2$ and/or $X^4$. The amino acids used in the amino acid sequences according to the invention may be in both L- and/or D-form. It is to be understood that both L- and D-forms may be used for different amino acids within the same peptide sequence. In some embodiments the amino acids within the peptide sequence are in L-form, such as natural amino acids. It is to be understood that any known antigen may be used in the constructs according to the present invention.

In some specific embodiments, the first 1, 2, or 3 amino acids in the N-terminal of the amino acid sequences according to the invention are in the D-form. It is assumed that the N-terminal trimming and thereby degradation of the peptides are somewhat delayed by having amino acids of the D-form in the N-terminal of these cell-penetrating peptides. Alternatively and in some embodiments, the first 1, 2, or 3 amino acids in the N-terminal of the amino acid sequences according to the invention are amino acids in beta or gamma forms. Beta amino acids have their amino group bonded to the beta carbon rather than the alpha carbon as in the 20 standard natural amino acids.

Alternatively the first 1, 2, or 3 amino acids in the N-terminal of the amino acid sequences according to the invention may be modified by incorporation of fluorine, or alternatively cyclic amino acids or other suitable non-natural amino acids are used.

A "variant" or "analogue" of a peptide refers to a peptide having an amino acid sequence that is substantially identical to a reference peptide, typically a native or "parent" polypeptide. The peptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having an the side chain $-(CH_2)_nNH_3$, where n is different from 4, and arginine may be substituted with an amino acid having the side chain $-(CH_2)_nNHC(=NH_2)NH_2$, where n is different from 3, etc. Similarly, the acidic amino acids aspartic acid and glutamic acid may be substituted with amino acid residues having the side chains $-(CH_2)_nCOOH$, where n>2.

The term "substantially identical" in the context of two amino acid sequences means that the sequences, when optimally aligned, such as by the programs GAP or BESTFIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms, or when deducing the is the computer program BLAST, especially blastp, using default parameters. See, e.g., Altschul et al., J. Mol. Biol. 1990; 215:403-410; Altschul et al., Nucleic Acids Res. 3.997; 25:3389-402 (1997); each herein incorporated by reference. "Corresponding" amino acid positions in two substantially identical amino acid sequences are those aligned by any of the protein analysis software mentioned herein, typically using default parameters.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a peptide molecule will exhibit 98%-99% homogeneity for peptide molecules in the context of all present peptide species in the composition or at least with respect to substantially active peptide species in the context of proposed use.

The term "linear sequence" as used herein refers to the specific sequence of amino acids connected by standard peptide bonds in standard N- to C-terminal direction. The peptide may contain only peptide bonds. However the term does not exclude that an amino acid within a sequence, such as within $X^3$, may be connected, such as through the side chains, with another amino acid at a distant location within the peptide sequence, such as a distant location within $X^3$.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "antigen" denotes a substance of matter which is recognized by the immune system's specifically recognizing components (antibodies, T-cells).

The term "immunogen" is in the present context intended to denote a substance of matter, which is capable of inducing an adaptive immune response in an individual, where said adaptive immune response targets the immunogen. In relation to the present invention, an immunogen will induce a humoral and/or cell-mediated immune response. In other words, an immunogen is an antigen, which is capable of inducing immunity.

The terms "epitope", "antigenic determinant" and "antigenic site" are used interchangeably herein and denotes the region in an antigen or immunogen which is recognized by antibodies (in the case of antibody binding epitopes, also known as "B-cell epitopes") or by T-cell receptors when the epitope is complexed to a Major histocompatibility complex (MHC) molecule (in the case of T-cell receptor binding epitopes, i.e. "T-cell epitopes").

The term "immunogenically effective amount" has its usual meaning in the art, i.e. an amount of an immunogen, which is capable of inducing an immune response, which significantly engages pathogenic agents, which share immunological features with the immunogen.

The term "vaccine" is used for a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "T helper lymphocyte epitope" (a $T_H$ epitope) is peptide, which binds an MHC Class II molecule and can be presented on the surface of an antigen presenting cell (APC) bound to the MHC Class II molecule. An "immunological carrier" is generally a substance of matter which includes one or many $T_H$ epitopes, and which increase the immune response against an antigen to which it is coupled by ensuring that T-helper lymphocytes are activated and proliferate. Examples of known immunological carriers are the tetanus and diphtheria toxoids and keyhole limpet hemocyanin (KLH).

In the scaffold design according to the present invention, $X^2$ and $X^4$ defines a sequence of 8-30 amino acids, such as 8-20 amino acids derived from the antigen. This sequence of amino acids derived from an antigen may herein be referred to as an epitope.

Preferably the epitopes used in the scaffold according to the present invention are CTL epitopes. A "CTL inducing peptide" is a HLA Class I binding peptide that is capable of inducing a CTL response. In other embodiments the epitopes used in the scaffold design according to the present invention are HTL inducing peptides. A "HTL inducing peptide" is a HLA Class II binding peptide that is capable of inducing a HTL response.

The term "basic amino acid" as used herein refers to any amino acid including both natural and non-natural amino acids that has an isoelectric point above 6.3 (such as above 7.4) as measured according to Kice & Marvell "Modern Principles of organic Chemistry" (Macmillan, 1974) or Matthews and van Holde "Biochemistry" Cummings Publishing Company, 1996. Included within this definition are Arginine, Lysine, Homoarginine (Har), and Histidine as well as derivatives thereof. Suitable non-natural basic amino acids are e.g. as described in U.S. Pat. No. 6,858,396. Suitable positively charged amino acids includes non-natural alpha amino acids available from Bachem AG and includes alpha-amino-glycine, alpha,gamma-diaminobutyric acid, ornithine, alpha, beta-diaminoproprionic acid, alpha-difluoromethyl-ornithine, 4-amino-piperidine-4-carboxylic acid, 2,6-diamino-4-hexynoic acid, beta-(1-piperazinyl)-alanine, 4,5-dehydro-lysine, delta-hydroxy-lysine, omega-hydroxy-norarginine, homoarginine, omega-amino-arginine, omega-methyl-arginine, alpha-methyl-histidine, 2,5-diiodo-histidine, 1-methyl-histidine, 3-methyl-histidine, beta-(2-pyridyl)-alanine, beta-(3-pyridyl)-alanine, beta-(2-quinolyl)-alanine, 3-amino-tyrosine, 4-amino-phenylalanine, and spinacine. Furthermore, any mono or dicarboxylic amino acid is a suitable positively charged amino acid.

The term "neutral amino acid" as used herein refers to an amino acid that has an isoelectric point above between 4.8 and 6.3 as measured according to Kice & Marvell "Modern Principles of organic Chemsitry" (Macmillan, 1974). The term "acidic amino acid" as used herein refers to an amino acid that has an isoelectric point below 4.8 as measured according to Kice & Marvell "*Modern Principles of organic Chemsitry*" (Macmillan, 1974).

Unless otherwise indicated amino acids are abbreviated and mentioned by their standard nomenclature known to the person skilled in the art, such as with reference to "nomenclature and symbolism for amino acids and peptides" by the international union of pure and applied chemistry (IUPAC) (www.iupac.org).

Citrulline (In this document referred to with the one-letter symbol "B") and/or homocitrulline are well known non-natural amino acids that in some embodiments may be used in the sequence defined by $X^1$, $X^3$, or $X^5$.

In other alternative embodiments, tryptophan or tryptophan derivatives are used in the sequence defined by $X^1$, $X^3$, or $X^5$. Any suitable tryptophan derivatives may be used. As used herein "tryptophan derivatives" means an unnatural modified tryptophan amino acid residue including those disclosed in U.S. Pat. No. 7,232,803, such as tri tert.-butyltryptophan, di-tert-butyl tryptophan, 7-benzyloxytryptophan, homotryptophan, 5'-aminoethyltryptophan (available as side chain Boc and N-alpha FMOC derivative from RSP Amino Acids Analogues Inc, Boston, Mass., USA), N-Acetylhomotryptophan (Toronto Research), 7-Benzyloxytryptophan (Toronto Research), Homotryptophan (Toronto Research), and tryptophan residues which have been substituted at the 1-, 2-, 5- and/or 7-position of the indole ring, positions 1- or 2 —being preferred e.g. 5' hydroxy tryptophan.

The term "antibody response" refers to the production of antibodies (e.g., IgM, IgA, IgG) which bind to an antigen of interest, this response is measured for instance by assaying sera by antigen ELISA.

The term "adjuvant" as used herein refers to any compound which, when delivered together or simultaneously with an antigen, non-specifically enhances the immune response to that antigen. Exemplary adjuvants include but are not limited to oil in water and water in oil adjuvants, aluminum-based adjuvants (e.g., AIOH, AIPO4, etc), and Montanide ISA 720.

The terms "patient" and "subject" refer to a mammal that may be treated using the methods of the present invention.

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

The term "net charge" as used herein with reference to a peptide sequence refers to the total electric charge of the peptide sequence represented by the sum of charges of each individual amino acid in the peptide sequence, wherein each basic amino acid are given a charge of +1, each acidic amino acid a charge of −1, and each neutral amino acid a charge of 0. Accordingly, the net charge will depend on the number and identities of charged amino acids.

TABLE 1

Specific peptides according to the invention

| | Refer-ence ID **P-biotin** | | x2 | x3 | x4 | | | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126. | |
|---|---|---|---|---|---|---|---|---|---|
| Antigen | **N-Biotin** | x1 R | QIKIWFQN PVVHLTL | **RR R** | MKWKK QAGDDFSR | x5 | Modified (m) | X2-seq | x4-seq |
| HCV | **SP_2** | **RR** | GYIPLVGAPLG | **BGR** | VARALAHGVRV | | | 135-145 | 147-157 |
| HCV | **SP_3** | **R** | GYIPLVGAPLG | **RR** | VARALAHGVRV | | | 135-145 | 147-157 |
| HCV | **SP_4** | **R** | GYIPLVGAPLG | **RRR** | VARALAHGVRV | **R** | | 135-145 | 147-157 |
| HCV | **SP_5** | **RR** | GYIPLVGAPLG | **RR** | VARALAHGVRV | | | 135-145 | 147-157 |
| HCV | **SP_6** | **RR** | GYIPLVGAPLG | **RRR** | VARALAHGVRV | | | 135-145 | 147-157 |
| HCV | **SP_7** | **BR** | GYIPLVGAPLG | **RR** | VARALAHGVRV | | | 135-145 | 147-157 |
| HCV | **SP_8** | **RRR** | GYIPLVGAPLG | **BR** | VARALAHGVRV | | | 135-145 | 147-157 |
| HCV | **SP_9** | **R** | GYIPLVGAPLG | **KKK** | VARALAHGVRV | | | 135-145 | 147-157 |
| HCV | **SP_10** | **R** | GYIPLVGAPLG | **RRR** | VARALAHGVRV | | | 135-145 | 147-157 |
| HCV | **SP_11** | **KK** | GYIPLVGAPLG | **KK** | VARALAHGVRV | | | 135-145 | 147-157 |
| HCV | **SP_12** | W | GYIPLVGAPLG | **RR** | VARALAHGVRV | | | 135-145 | 147-157 |
| HCV | **SP_13** | WW | GYIPLVGAPLG | **RR** | VARALAHGVRV | | | 135-145 | 147-157 |
| HCV | **SP_14** | **EE** | GYIPLVGAPLG | **EE** | VARALAHGVRV | | | 135-145 | 147-157 |

TABLE 1-continued

Specific peptides according to the invention

| Antigen | Refer-ence ID P-biotin N-Biotin | x1 R | x2 QIKIWFQN PVVHLTL | x3 RR R | x4 MKWKK QAGDDFSR | x5 | Modified (m) | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126. X2-seq | x4-seq |
|---|---|---|---|---|---|---|---|---|---|
| HCV | **SP_15** | GG | GYIPLVGAPLG | GG | VARALAHGVRV | | | 135-145 | 147-157 |
| HCV | **SP_16** | **EE** | GYIPLVGAPLG | **RR** | VARALAHGVRV | | | 135-145 | 147-157 |
| HCV | **SP_17** | **RR** | GYIPLVGAPLG | **LRR** | VARALAHGVRV | | | 135-145 | 147-157 |
| HCV | **SP21**: | WW | GYIPLVGAPLG | **RR** | VARALAHGVRV | | | 135-145 | 147-157 |
| HCV | **SP22**: | WW | GYIPLVGAPLG | **RRR** | VARALAHGVRV | | | 135-145 | 147-157 |
| HCV | **SP23**: | WW | GYIPLVGAPLG | **R** | VARALAHGVRV | | | 135-145 | 147-157 |
| HCV | **SP24**: | **R** | GYIPLVGAPLG | **RR** | VARALAHGVRV | | | 135-145 | 147-157 |
| HCV | **51_BIotin** | RR | GYLPAVGAPIG | BR | VIRVIAHGLRL | | m | 135-144 | 147-157 |
| HCV | **51b_BIotin** | RR | GYIPLVGAPLG | BR | VARALAHGVRV | | | 135-145 | 147-157 |
| HCV | **51_n** | | GYIPLVGAPLG | *G* | VARALAHGVRV | | | 135-145 | 147-157 |
| HCV | **SP51_1**: | WW | GYLPAVGAPI | **RR** | VIRVIAHGLRL | | m | 135-144 | 147-157 |
| HCV | **SP1_C** * | | GYIPLVGAPLG | *G* | VARALAHGVRV | | | 135-145 | 147-157 |
| HCV | **SP2_c** | **RR** | GYIPLVGAPLG | **BGR** | VARALAHGVRV | | | 135-145 | 147-157 |
| HCV | **SP3_c** | **R** | GYIPLVGAPLG | **RR** | VARALAHGVRV | | | 135-145 | 147-157 |
| HCV | **SP4_c** | **R** | GYIPLVGAPLG | **RRR** | VARALAHGVRV | | | 135-145 | 147-157 |
| HCV | **SP5_c** | **RR** | GYIPLVGAPLG | **RR** | VARALAHGVRV | | | 135-145 | 147-157 |
| HCV | **SP6_c** | **RR** | GYIPLVGAPLG | **RRR** | VARALAHGVRV | | | 135-145 | 147-157 |
| HCV | **SP7_c** | **BR** | GYIPLVGAPLG | **RR** | VARALAHGVRV | | | 135-145 | 147-157 |
| HCV | **SP8_c** | **RRR** | GYIPLVGAPLG | **BR** | VARALAHGVRV | | | 135-145 | 147-157 |
| HCV | **SP9_c** | **R** | GYIPLVGAPLG | **KKK** | VARALAHGVRV | | | 135-145 | 147-157 |
| HCV | **SP10_c** | **R** | GYIPLVGAPLG | **RRR** | VARALAHGVRV | | | 135-145 | 147-157 |

TABLE 1-continued

Specific peptides according to the invention

| Antigen | Reference ID P-biotin N-Biotin | x1 R | x2 QIKIWFQN PVVHLTL | x3 RR R | x4 MKWKK QAGDDFSR | x5 | Modified (m) | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126. X2-seq | x4-seq |
|---|---|---|---|---|---|---|---|---|---|
| HCV | **SP11_c** | KK | GYIPLVGAPLG | KK | VARALAHGVRV | | | 135-145 | 147-157 |
| HCV | **SP12_c** | W | GYIPLVGAPLG | RR | VARALAHGVRV | | | 135-145 | 147-157 |
| HCV | **SP13_c** | WW | GYIPLVGAPLG | RR | VARALAHGVRV | | | 135-145 | 147-157 |
| HCV | **SP17_c** | RR | GYIPLVGAPLG | LRR | VARALAHGVRV | | | 135-145 | 147-157 |
| HCV | **SP61_2_** | RR | NYVTGNIPG | BR | GITFSIFLIVS | | | 163-171 | 171-181 |
| HCV | **SP61b_2_** | WW | NYATGNLPG | RR | CSFSIFLLAL | | m | 163-171 | 171-181 |
| HCV | **SP61_3_** | WW | NYVTGNIPG | BR | GITFSIFLIVS | | | 163-171 | 171-181 |
| HCV | **SP61_4_** | WW | NYVTGNIPG | RR | GITFSIFLIVS | | | 163-171 | 171-181 |
| HCV | **61b_BIotin** | RR | NYATGNLPG | RR | GCSFSIFLLAL | | | 163-171 | 171-181 |
| HCV | **SP25** | RR | VTGNIPGSTYS | GBR | GITFSIYLIVS | | m | 165-175 | 171-181 |
| HCV | **42_BIotin** | RR | IRNLGRVIETLTG | BR | LZGYIPLIGA | | m | 116-128 | 133-142 |
| HCV | **42b_BIotin** | RR | SRNLGKVIDTLTC | BR | LMGYIPLVGA | | | 116-128 | 133-142 |
| HCV | **42n-BIOTIN** | | SRNLGKVIDTLTC | GFAD | LMGYIPLVGA | | | 116-129 | 133-142 |
| HCV | **SP42_1_** | WW | IRNLGRVIETLT | RR | LZGYIPLIGA | | m | 116-128 | 133-142 |
| HCV | **SP42b_1_** | WW | SRNLGKVIDTLTC | RR | LMGYIPLVGA | | | 116-129 | 133-142 |
| HCV | **BI310-11_Biotin** | RR | GGGQIIGGNYLIP | RB | PBIGVRATB | | | 26-38 | 42-50 |
| HCV | **BI310-11n_Biotin** | | GGGQIVGGVYLLP | RR | GPRLGVRATR | | | 26-38 | 42-50 |
| HCV | **BI310-11n_sc_Biotin** | RR | GGGQIVGGVYLLP | RR | GPRLGVRATR | | | 26-38 | 42-50 |
| HCV | SP11b-1- | WW | GGGQIVGGVYLLP | RR | GPRLGVRAT | | | 26-38 | 42-50 |

TABLE 1-continued

Specific peptides according to the invention

| Antigen | Reference ID P-biotin<br>**N-Biotin** | x1<br>**R** | x2<br>QI**K**IWFQN PVVHLTL | x3<br>**RR R** | x4<br>MKW**KK** QAGDDFS**R** | x5 | Modified (m) | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126.<br>X2-seq | x4-seq |
|---|---|---|---|---|---|---|---|---|---|
| FLU | **BI100-12** | BR | LIFLARSALIV | | RGSVAHKS | | | 256-266 | 267-274 |
| FLU | **BI100-22b** | ED | LIFLARSALIL | | RGSVAHKS | | | 255-266 | 267-274 |
| FLU | **120b_BIotin** | BR | LIFLARSALIL | BGR | SALILRGSVAHK | | | 255-266 | 267-274 |
| FLU | **BI100-18b** | | SAYERMCNIL | KGK | FQTAAQRAMM | | | 217-226 | 230-239 |
| FLU | **BI100-19** | | SAYERZVNIL | KGK | FQTAAQRAVZ | | | 217-226 | 230-239 |
| FLU | **190_BIotin** | BR | TAYERZCNIL | BRGR | FQTVVQBA | | | 217-226 | 230-237 |
| FLU | **190b_BIotin** | BR | IAYERMCNIL | LBRGK | FQTAAQRA | | | 217-226 | 230-237 |
| FLU | 190n-BIOTIN | | IAYERMCNIL | KGK | FQTAAQRA | | | 217-226 | 230-237 |
| FLU | BI100-24b | | LFFKCIYRLFKHGL | KR | GPSTEGVPESM | | | 46-59 | 62-72 |
| FLU | BI100-26 | BRR | LFFKTITRLFBHGL | RR | LLSTEGVPNSZ | | | 46-59 | 62-72 |
| FLU | **260_Biotin** | BR | GLEPLVIAGILA | RR | GSLVGLLHIVL | | | 23-33 | 30-40 |
| FLU | **260b_Biotin** | BR | GSDPLVVAASIV | RR | ASIVGILHLIL | | | 23-33 | 30-40 |
| CMV | **BI 050-sc1** | **R** | NLVPMVATV | **RR** | NLVPMVATV | **B** | | 485-493 | 485-493 |
| CMV | **BI 050-sc2** | **R** | NLVPMVATV | **BRR** | NLVPMVATV | **B** | | 485-493 | 485-493 |
| CMV | **BI 050-sc5** | **R** | NIVPZVVTA | **RR** | NIVPZVVTA | **B** | m | 485-493 | 485-493 |
| HIV | N10 | | P**E**VIPMFSALS | **E**GA | TPQ**D**LNTMLN | | | | |
| HIV | V10 | **R** | FIIPXFTALSG | G**RR** | ALLYGATPYAIG | | | | |
| HIV | N13 | **K** | ALGPAATL | **EE** | MMTACQGVG | | | | |
| Neg c mod | **SP_18** | **RR** | GPVVHLTL | **RRR** | GQAG**DD**FS | | | | |
| Neg c mod | **SP_19** | **RR** | GPVVHLTL | **RRR** | GQAG**DD**FS | | | | |
| Neg c mod | **SP_20** | **RR** | GPVVHLTL | **RGRR** | GQAG**DD**FS | | | | |

TABLE 1-continued

Specific peptides according to the invention

| Antigen | Reference ID P-biotin<br>N-Biotin | x1<br>R | x2<br>QIKIWFQN PVVHLTL | x3<br>RR R | x4<br>MKWKK QAGDDFSR | x5 | Modified (m) | Placement with reference to positions in SEQ ID NO: 3; SEQ ID NO: 6; SEQ ID NO: 7, SEQ ID NO: 11, SEQ ID NO: 12, SEQ ID NO: 46, and SEQ ID NO: 126.<br>X2-seq | <br>x4-seq |
|---|---|---|---|---|---|---|---|---|---|
| HPV | | RR | LECVYCKQQLL | RR | EVYDFAFRDLC | | | 35-45 | 48-58 |
| HPV | | RR | **G**VYDFAFRDLC | **RR** | **G**FAFRDLCIVY | **R** | | 49-58 | 52-61 |
| HPV | | RR | **G**VFDYAFRDIN | **RR** | **G**FAYRDINLAY | **R** | | 49-58 | 52-61 |
| CMV | | **RR** | **G**ATPVDLLGA | **RR** | GALNLCLPM | **R** | | 498-506 | 505-514 |
| CMV | | **RR** | **G**VTPAGLIGV | **RR** | GALQIBLPL | **R** | | 498-506 | 505-514 |
| HPV | | **RR** | VDIRTLEDLL | **RR** | GTLGIVCPIG | **R** | | 74-83 | 84-93 |

As used herein the one-letter-code 'Z' refers to the non-natural amino acid norleucine.

TABLE 2

Specific peptides according to the invention

| Antigen | $X^1$ | $X^2$ | $X^3$ | $X^4$ | $X^5$ |
|---|---|---|---|---|---|
| HCV | R | GYIPLVGAPLG | RRR | VARALAHGVRV | R |
| HCV | R | GYLPAVGAPIG | RRR | VIRVIAHGLRL | R |
| HCV | RR | GYIPLVGAPLG | RR | VARALAHGVRV | |
| HCV | RR | GYIPLVGAPLG | RRR | VARALAHGVRV | |
| HCV | RR | SRNLGKVIDTLTC | RR | LMGYIPLVGA | |
| HCV | RR | GGGQIVGGVYLLP | RR | GPRLGVRATR | |
| HCV | W | GYIPLVGAPLG | RR | VARALAHGVRV | |
| HCV | RR | IRNLGRVIETLTLZGYIPLIGA | RR | IRNLGRVIETLTLZGYIPLIGA | R |
| Flu | BR | TAYERZCNIL | BRGR | FQTVVQBA | |
| cmv | R | NLVPMVATV | BRR | NLVPMVATV | B |

As used herein the one-letter-code 'Z' refers to the non-natural amino acid norleucine.

Antigens

Examples of viral antigens for use with the present invention include, but are not limited to, e.g., HIV, HCV, CMV, HPV, Influenza, adenoviruses, retroviruses, picornaviruses, etc. Non-limiting example of retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NSI, NSI, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

The epitopes to be incorporated into the scaffold design according to the present invention may be derived from an adenovirus, retrovirus, picornavirus, herpesvirus, rotavirus, hantavirus, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongiform virus. In certain specific, non-limiting examples, the viral antigen are peptides obtained from at least one of HIV, CMV, hepatitis A, B, and C, influenza, measles, polio, smallpox, rubella; respiratory syncytial, herpes simplex, varicella zoster, Epstein-Barr, Japanese encephalitis, rabies, Influenza, and/or cold viruses.

HCV:

Peptides according to the present invention may comprise a known antigen. For antigens derived from HCV these antigens may be derived from the Core, E1, E2, P7, NS2, NS3, NS4 (NS4A and NS4B) and NS5 (NS5A and NS5B) protein of the Hepatitis C Virus (HCV). The epitopes are those which elicit a HLA class I and/or class II restricted T lymphocyte response in an immunized host. More specific, the HLA class I restricted peptides of the present invention may bind to at least one HLA molecule of the following HLA class I groups: HLA-A*01, HLA-A*02, HLA-A*03, HLA-A*11, HLA-A*24, HLA-B*07, HLA-B*08, HLA-B*35, HLA-B*40, HLA-B*44, HLA-Cw3, HLA-Cw4, HLA-Cw6 or HLA-Cw7. The HLA class II restricted peptides of the present invention may bind to at least one HLA molecule of the following HLA class II groups: HLA-DRB1, -DRB2, -DRB3, -DRB4, -DRB5, -DRB6, -DRB7, -DRB8 or -DRB9.

MHC binding HCV peptides that may be used according to the present invention as epitopes are disclosed in e.g. WO02/34770 (Imperial College Innovations Ltd), WO01/21189 and WO02/20035 (Epimmune), WO04/024182 (Intercell), WO95/25122 (The Scripps Research Institute), WO95/27733 (Government of the USA, Department of Health and Human Services), EP 0935662 (Chiron), WO02/26785 (Immusystems GmbH), WO95/12677 (Innogenetics N.V), WO97/34621 (Cytel Corp), and EP 1652858 (Innogenetics N.V.).

In other embodiments, the scaffold design according to the present invention comprises a PADRE peptide, such as the universal T cell epitope called PADRE as disclosed in WO95/07707 (Epimmune) the content of which are enclosed herein by reference. A 'PanDR binding peptide or PADRE peptide" is a member of a family of molecules that binds more that one HLA class II DR molecule. PADRE binds to most HLA-DR molecules and stimulates in vitro and in vivo human helper T lymphocyte (HTL) responses. Alternatively T-help epitopes can be used from universally used vaccines such as tetanos toxoid.

In a further embodiment, the peptides in the composition or polyepitopic peptide are characterized in that they are derived from a HCV protein, or more specifically from at least one of the following HCV regions selected from the group consisting of Core, E1, E2/NS1, NS2, NS3, NS4A, NS4B, NS5A and NS5B. Even more preferred is that peptides are characterized in that they are present in the HCV consensus sequence of genotype 1a, 1b and/or 3 a.

Other HLA class I and II binding peptides that may be used according to the invention may be identified by the method as described in WO03/105058—Algonomics, by the method as described by Epimmune in WO01/21189 and/or by three public database prediction servers, respectively Syfpeithi, BIMAS and nHLAPred. It is also an aspect of this present invention that each peptide may be used within the scaffold design of the invention in combination with the same peptide as multiple repeats, or with any other peptide(s) or epitope(s).

CMV:

The epitopes to be incorporated into the scaffold design according to the present invention may be derived from cytomegalovirus (CMV) including CMV glycoproteins gB and gH.

Influenza:

The epitopes to be incorporated into the scaffold design according to the present invention may be derived from fragments or portions of Influenza hemagglutinin (HA) or Influenza neuraminidase (NA), nucleoprotein (NP), M1, M2, NS1, NEP, PA, PB1, PB1-F2, PB2 for each of the subgroups, such as H1N1, H2N2 og H3N2.

Suitable epitopes may be derived from an HA protein of one, or more than one subtype, including H1, H2, H3, H4, H5, H6, H7, H8, H9, H10, H11, H12, H13, H14, H15 or H16 or fragment or portion thereof. Examples of subtypes comprising such HA proteins include A/New Caledonia/20/99 (H1N1) A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68 (H8N4), A/shoveler/Iran/G54/03, A/chicken/Germany/N/1949 (H10N7), A/duck/England/56 (H11N6), A/duck/Alberta/60/76 (H12N5), A/Gull/Maryland/704/77 (H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

In some embodiments of the invention, the HA protein may be an H1, H2, H3, H5, H6, H7 or H9 subtype. In other embodiments, the H1 protein may be from the A/New Caledonia/20/99 (H1N1), A/PuertoRico/8/34 (H1N1), A/Brisbane/59/2007 (H1N1), or A/Solomon Islands 3/2006 (H1N1) strain. The H3 protein may also be from the A/Brisbane 10/2007 (H3N2) or A/Wisconsin/67/2005 (H3N2) strain. In other embodiments, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In other embodiments, the H6 protein may be from the A/Teal/HongKong/W312/97 (H6N1) strain. The H7 protein may be from the A/Equine/Prague/56 (H7N7) strain. In other embodiments, the H9 protein is from the A/HongKong/

1073/99 (H9N2) strain. In other embodiments, the HA protein may be from an influenza virus may be a type B virus, including B/Malaysia/2506/2004 or B/Florida/4/2006. The influenza virus HA protein may be H5 Indonesia.

Human Immunodeficiency Virus (HIV):

For HIV, the epitopes to be incorporated into the scaffold design according to the present invention may be derived from the group consisting of gp120, gp160, gp41, p24gag or p55gag derived from HIV, including members of the various genetic subtypes.

Human Papillomavirus (HPV):

For HPV, the epitopes to be incorporated into the scaffold design according to the present invention may be derived from the group consisting E1, E2, E3, E4, E6 and E7, L1 and L2 proteins. The epitopes may be derived from any type including types 8, 11, 16, 18, 31, 33, 35, 39, 45, 51, 52, 56, 58, and 59.

Carriers, Adjuvants and Vehicles—Delivery

The isolated cell-penetrating peptides according to the invention may be delivered by various means and within various compositions, herein referred to as "compositions", "vaccine compositions" or "pharmaceutical compositions". The peptides of the present invention and pharmaceutical and vaccine compositions of the invention are useful for administration to mammals, particularly humans, to treat and/or prevent virus infection. Vaccine compositions containing the peptides of the invention are administered to a patient infected with the virus in question or to an individual susceptible to, or otherwise at risk for, virus infection to elicit an immune response against the specific antigens and thus enhance the patient's own immune response capabilities.

Various art-recognized delivery systems may be used to deliver the peptides, into appropriate cells. The peptides can be delivered in a pharmaceutically acceptable carrier or as colloidal suspensions, or as powders, with or without diluents. They can be "naked" or associated with delivery vehicles and delivered using delivery systems known in the art.

A "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvant typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles; aluminium hydroxide, aluminium phosphate (see International Patent Application Publication No. WO93/24148), alum (KAI(SO4)2.12H2O), or one of these in combination with 3-0-deacylated monophosphoryl lipid A (see International Patent Application Publication No. WO93/19780); N-acetyl-muramyl-L-threonyl-D-isoglutamine (see U.S. Pat. No. 4,606,918), N-acetyl-normuramyl-L-alanyl-D-isoglutamine, N-acetylmuramyl-L-alanyl-D-isoglutamyl-L-alanine2-(1',2'-dipalmitoyl-sn-glycero-3-hydroxyphosphoryloxy) ethylamine; RIBI (ImmunoChem Research Inc., Hamilton, Mont., USA) which contains monophosphoryl lipid A (i.e., a detoxified endotoxin), trehalose-6,6-dimycolate, and cell wall skeleton (MPL+TDM+CWS) in a 2% squalene/Tween 80 emulsion. Any of the three components MPL, TDM or CWS may also be used alone or combined 2 by 2; adjuvants such as Stimulon (Cambridge Bioscience, Worcester, Mass., USA), SAF-1 (Syntex); adjuvants such as combinations between QS21 and 3-de-O-acetylated monophosphoryl lipid A (see International Application No. WO94/00153) which may be further supplemented with an oil-in-water emulsion (see, e.g., International Application Nos. WO95/17210, WO97/01640 and WO9856414) in which the oil-in-water emulsion comprises a metabolisable oil and a saponin, or a metabolisable oil, a saponin, and a sterol, or which may be further supplemented with a cytokine (see International Application No. WO98/57659); adjuvants such as MF-59 (Chiron), or poly[di(carboxylatophenoxy) phosphazene] based adjuvants (Virus Research Institute); blockcopolymer based adjuvants such as Optivax (Vaxcel, Cytrx) or inulin-based adjuvants, such as Algammulin and Gammalnulin (Anutech); Complete or Incomplete Freund's Adjuvant (CFA or IFA, respectively) or Gerbu preparations (Gerbu Biotechnik); a saponin such as QuilA, a purified saponin such as QS21, QS7 or QS17, -escin or digitonin; immunostimulatory oligonucleotides comprising unmethylated CpG dinucleotides such as [purine-purine-CG-pyrimidine-pyrimidine] oligonucleotides. These immunostimulatory oligonucleotides include CpG class A, B, and C molecules (Coley Pharmaceuticals), ISS (Dynavax), Immunomers (Hybridon). Immunostimulatory oligonucleotides may also be combined with cationic peptides as described, e.g., by Riedl et al. (2002); Immune Stimulating Complexes comprising saponins, for example Quil A (ISCOMS); excipients and diluents, which are inherently non-toxic and non-therapeutic, such as water, saline, glycerol, ethanol, isopropyl alcohol, DMSO, wetting or emulsifying agents, pH buffering substances, preservatives, and the like; a biodegradable and/or biocompatible oil such as squalane, squalene, eicosane, tetratetracontane, glycerol, peanut oil, vegetable oil, in a concentration of, e.g., 1 to 10% or 2.5 to 5%; vitamins such as vitamin C (ascorbic acid or its salts or esters), vitamin E (tocopherol), or vitamin A; carotenoids, or natural or synthetic flavanoids; trace elements, such as selenium; any Toll-like receptor ligand as reviewed in Barton and Medzhitov (2002).

Any of the afore-mentioned adjuvants comprising 3-de-O-acetylated monophosphoryl lipid A, said 3-de-O-acetylated monophosphoryl lipid A may be forming a small particle (see International Application No. WO94/21292).

In any of the aforementioned adjuvants MPL or 3-de-O-acetylated monophosphoryl lipid A can be replaced by a synthetic analogue referred to as RC-529 or by any other amino-alkyl glucosaminide 4-phosphate (Johnson et al. 1999, Persing et al. 2002). Alternatively it can be replaced by other lipid A analogues such as OM-197 (Byl et al. 2003).

A "pharmaceutically acceptable vehicle" includes vehicles such as water, saline, physiological salt solutions, glycerol, ethanol, etc. Auxiliary substances such as wetting or emulsifying agents, pH buffering substances, preservatives may be included in such vehicles. Delivery systems known in the art are e.g. lipopeptides, peptide compositions encapsulated in poly-DL-lactide-co-glycolide ("PLG"), microspheres, peptide compositions contained in immune stimulating complexes (ISCOMS), multiple antigen peptide systems (MAPs), viral delivery vectors, particles of viral or synthetic origin, adjuvants, liposomes, lipids, microparticles or microcapsules, gold particles, nanoparticles, polymers, condensing agents, polysaccharides, polyamino acids, dendrimers, saponins, QS21, adsorption enhancing materials, fatty acids or, naked or particle absorbed cDNA.

Typically, a vaccine or vaccine composition is prepared as an injectable, either as a liquid solution or suspension. Injection may be subcutaneous, intramuscular, intravenous, intraperitoneal, intrathecal, intradermal, or intraepidermal. Other types of administration comprise electroporation, implantation, suppositories, oral ingestion, enteric application, inhalation, aerosolization or nasal spray or drops. Solid forms, suitable for dissolving in, or suspension in, liquid vehicles prior to injection may also be prepared. The preparation may also be emulsified or encapsulated in liposomes for enhancing adjuvant effect.

A liquid formulation may include oils, polymers, vitamins, carbohydrates, amino acids, salts, buffers, albumin, surfactants, or bulking agents. Preferably carbohydrates include sugar or sugar alcohols such as mono-, di-, tri-, oligo- or polysaccharides, or water-soluble glucans.

The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to the amount used as long as the sugar or sugar alcohol is soluble in the aqueous preparation. Preferably, the sugar or sugar alcohol concentration is between 1.0% (w/v) and 7.0% (w/v), more preferable between 2.0 and 6.0% (w/v). Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, polypeptides can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the general formula:

R(O—CH2-CH2)nO—R where R can be hydrogen, or a protective group such as an alkyl or alkanol group. Preferably, the protective group has between 1 and 8 carbons, more preferably it is methyl. The symbol n is a positive integer, preferably between 1 and 1.000, more preferably between 2 and 500. The PEG has a preferred average molecular weight between 1000 and 40.000, more preferably between 2000 and 20.000, most preferably between 3.000 and 12.000. Preferably, PEG has at least one hydroxy group, more preferably it is a terminal hydroxy group. It is this hydroxy group which is preferably activated. However, it will be understood that the type and amount of the reactive groups may be varied to achieve a covalently conjugated PEG/polypeptide of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, and a discussion of POG/IL-2 conjugates is found in U.S. Pat. No. 4,766,106.

Another drug delivery system for increasing circulatory half-life is the liposome. The peptides and nucleic acids of the invention may also be administered via liposomes, which serve to target a particular tissue, such as lymphoid tissue, or to target selectively infected cells, as well as to increase the half-life of the peptide and nucleic acids composition. Liposomes include emulsions, foams, micelles, insoluble monolayers, liquid crystals, phospholipid dispersions, lamellar layers and the like. In these preparations, the peptide or nucleic acids to be delivered is incorporated as part of a liposome or embedded, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide or nucleic acids of the invention can be directed to the site of lymphoid cells, where the liposomes then deliver the peptide and nucleic acids compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al, 1980, and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated. For example, liposomes carrying either immunogenic polypeptides are known to elicit CTL responses in vivo (Reddy et al., 1992; Collins et al., 1992; Fries et al., 1992; Nabel et al., 1992).

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Use of the Peptides for Evaluating Immune Responses.

The peptides according to the present invention may be used as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing a chronic virus infection.

Accordingly, the present invention relates to a method of determining the outcome for a subject exposed to a virus, comprising the steps of determining whether the subject has an immune response to one or more peptides according to the present invention.

In a preferred embodiment of the invention, the peptides as described herein can be used as reagents to evaluate an immune response. The immune response to be evaluated can be induced by using as an immunogen any agent that may result in the production of antigen-specific CTLs or HTLs that recognize and bind to the peptide(s) to be employed as the reagent. The peptide reagent need not be used as the immunogen. Assay systems that can be used for such an analysis include relatively recent technical developments such as tetramers, staining for intracellular lymphokines and interferon release assays, or ELISPOT assays.

For example, a peptide of the invention may be used in a tetramer staining assay to assess peripheral blood mononuclear cells for the presence of antigen-specific CTLs following exposure to an antigen or an immunogen. The HLA-tetrameric complex is used to directly visualize antigen-specific CTLS (see, e.g., Ogg et al., 1998; and Altman et al., 1996) and determine the frequency of the antigen-specific CTL population in a sample of peripheral blood mononuclear cells. A tetramer reagent using a peptide of the invention may be generated as follows: a peptide that binds to an HLA molecule is refolded in the presence of the corresponding HLA heavy chain and beta2-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes. Cells identified by the procedure can also be used for therapeutic purposes. As an alternative to tetramers also pentamers or dimers can be used (Current Protocols in Immunology (2000) unit 17.2 supplement 35)

Peptides of the invention may also be used as reagents to evaluate immune recall responses. (see, e.g., Bertoni et al., 1997 and Perma et al., 1991.). For example, patient PBMC samples from individuals with HCV infection may be analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for cytotoxic activity (CTL) or for HTL activity.

The peptides may also be used as reagents to evaluate the efficacy of a vaccine.

PBMCs obtained from a patient vaccinated with an immunogen may be analyzed using, for example, either of the methods described above. The patient is HLA typed, and peptide epitope reagents that recognize the allele-specific molecules present in that patient are selected for the analysis. The immunogenicity of the vaccine is indicated by the presence of epitope-specific CTLs and/or HTLs in the PBMC sample.

The peptides of the invention may also be used to make antibodies, using techniques well known in the art (see, e.g. CURRENT PROTOCOLS IN IMMUNOLOGY, Wiley/Greene, N.Y.; and Antibodies A Laboratory Manual, Harlow and Lane, Cold Spring Harbor Laboratory Press, 1989). Such antibodies include those that recognize a peptide in the context of an HLA molecule, i.e., antibodies that bind to a peptide-MHC complex.

SPECIFIC EMBODIMENTS OF THE INVENTION

The present invention concerns a peptide an isolated cell-penetrating peptide comprising the following structure $$X^1\text{-}X^2\text{-}X^3\text{-}X^4\text{-}X^5 \quad \text{(formula I)},$$

wherein $X^1$ and $X^3$ independently defines a linear sequence of any 1, 2, 3 or 4 amino acid independently selected from any basic amino acid, citrulline, tryptophan, or a derivative thereof; $X^2$ defines a linear sequence of 8-30 amino acids derived from an antigen; $X^4$ defines a linear sequence of 8-30 amino acids derived from said antigen, said sequence $X^4$ being different from $X^2$; and wherein $X^5$ is any one optional amino acid selected from a basic amino acid, citrulline, tryptophan, or a derivative thereof.

In some specific embodiments the sequence of $X^4$ is identical to the sequence of $X^2$.

In some embodiments the isolated cell-penetrating peptide has a total of not more than 60 amino acids.

In some embodiments $X^1$ defines a linear sequence of any 1, 2, 3, or 4 amino acids independently selected from any basic amino acid, tryptophan, or a derivative thereof.

In some embodiments $X^1$ defines a linear sequence in any order of one citrulline and any 1, 2, or 3 amino acids independently selected from any basic amino acid, tryptophan, or a derivative thereof.

In some embodiments $X^3$ defines a linear sequence of any 1, 2, 3, or 4 amino acids independently selected from any basic amino acid.

In some embodiments $X^1$ defines a linear sequence of any 1, 2, 3, or 4 amino acids independently selected from any basic amino acid.

In some embodiments $X^3$ defines a linear sequence in any order of one citrulline and of any 1, 2, or 3 amino acids independently selected from any basic amino acid.

In some embodiments the sequence of amino acids defined by $X^2\text{-}X^3\text{-}X^4$ of formula I as defined in claim 1 is not found in the native sequence of said antigen.

In some embodiments the sequence of amino acids defined by $X^1\text{-}X^2\text{-}X^3\text{-}X^4$ of formula I as defined in claim 1 is not found in the native sequence of said antigen.

In some embodiments the sequence of amino acids defined by $X^1\text{-}X^2\text{-}X^3\text{-}X^4\text{-}X^5$ of formula I as defined in claim 1 is not found in the native sequence of said antigen.

In some embodiments the peptide is demonstrated to translocate across a plasma membrane in the assay based on biotinylation of peptides as described in example 1.

In some embodiments the 1, 2, 3 or 4 amino acid independently selected from any basic amino acid, citrulline, tryptophan, or a derivative thereof, is a basic amino acid.

In some embodiments the 1, 2, 3 or 4 amino acid independently selected from any basic amino acid, citrulline, tryptophan, or a derivative thereof, is tryptophan, or a derivative thereof.

In some embodiments the 1, 2, 3 or 4 amino acid independently selected from any basic amino acid, citrulline, tryptophan, or a derivative thereof, is citrulline, or a derivative thereof.

In some embodiments the one optional amino acid selected from a basic amino acid, citrulline, tryptophan, or a derivative thereof is selected from Arg, Lys, and His.B).

In some embodiments the one optional amino acid selected from a basic amino acid, citrulline, tryptophan or a derivative thereof is tryptophan, or a derivative thereof.

In some embodiments the one optional amino acid selected from a basic amino acid, citrulline, tryptophan or a derivative thereof is citrulline, or a derivative thereof.

In some embodiments $X^2$ and/or $X^4$ defines a sequence identical to the native sequence of said antigen.

In some embodiments the peptide is capable of inducing a T-lymphocyte response.

In some embodiments the peptide is capable of inducing a CD4+ and/or a CD8+ T-lymphocyte response.

In some embodiments the antigen is a viral protein, such as a capsid protein.

In some embodiments the viral protein is selected from a protein of the Hepatitis C virus, such as a core protein; protein of influenza virus, such as an M2 protein.

In some embodiments the viral protein of Hepatitis C virus is selected from HCV consensus sequence of genotype 1, such as subtypes 1a and 1b, genotype 2 such as 2a and 2b and genotype 3, such as 3a.

In some embodiments the cell-penetrating peptide is of 19-60 amino acids, such as of 20-60 amino acids, such as of 21-60 amino acids, such as of 22-60 amino acids, such as of 23-60 amino acids, such as of 24-60 amino acids, such as of 25-60 amino acids, such as of 26-60 amino acids, such as of 27-60 amino acids, such as of 28-60 amino acids, such as of 29-60 amino acids, such as of 30-60 amino acids, such as of 31-60 amino acids, such as of 32-60 amino acids, such as of 33-60 amino acids, such as of 34-60 amino acids, such as of 35-60 amino acids.

In some embodiments the cell-penetrating peptide is of 18-60 amino acids, such as 18-59 amino acids, such as 18-58 amino acids, such as 18-57 amino acids, such as 18-56 amino acids, such as 18-55 amino acids, such as 18-54 amino acids, such as 18-53 amino acids, such as 18-52 amino acids, such as 18-51 amino acids, such as 18-50 amino acids, such as 18-49 amino acids, such as 18-48 amino acids, such as 18-47 amino acids, such as 18-46 amino acids, such as 18-45 amino acids, such as 18-44 amino acids, such as 18-43 amino acids, such as 18-42 amino acids, such as 18-41 amino acids, such as 18-40 amino acids, such as 18-39 amino acids, such as 18-38 amino acids, such as 18-37 amino acids, such as 18-35 amino acids, such as of 18-34 amino acids, such as of 18-33 amino acids, such as of 18-32 amino acids, such as of 18-31 amino acids, such as of 18-30 amino acids, such as of 18-29 amino acids, such as of 18-28 amino acids, such as of 18-27 amino acids, such as of 18-26 amino acids, such as of 18-25 amino acids, such as of 18-24 amino acids, such as of 18-23 amino acids, such as of 18-22 amino acids, such as of 18-21 amino acids, such as of 18-20 amino acids, such as of 18-19 amino acids.

In some embodiments the net charge of $X^2$ is below or equal to 0.

In some embodiments the net charge of $X^2$ is below or equal to 0; and $X^1$ and $X^3$ defines a sequence of 2, 3 or 4 amino acid independently selected from any basic amino acid, citrulline, tryptophan, or a derivative thereof.

In some embodiments the net charge of $X^2$ is below or equal to 0; and the net charge of $X^4$ is above or equal to 1.

In some embodiments the net charge of $X^2$ is below or equal to 0; the net charge of $X^4$ is above or equal to 1; and $X^1$ and $X^3$ defines a sequence of 2, 3 or 4 amino acid independently selected from any basic amino acid, citrulline, tryptophan, or a derivative thereof.

In some embodiments the net charge of $X^2$ and $X^4$ are below or equal to 0.

In some embodiments the net charge of $X^2$ and $X^4$ are below or equal to 0; and $X^1$ and $X^3$ defines a sequence of 2, 3 or 4 amino acid independently selected from any basic amino acid, citrulline, tryptophan, or a derivative thereof.

In some embodiments the net charge of $X^2$ and $X^4$ are above or equal to 1.

In some embodiments the net charge of $X^2$ and $X^4$ are above or equal to 1 and $X^1$ and $X^3$ defines a sequence of 1 or 2 amino acid independently selected from any basic amino acid, citrulline, tryptophan, or a derivative thereof.

In some embodiments the net charge of $X^2$ is above or equal to 1; and the net charge of $X^4$ is below or equal to 0.

In some embodiments the net charge of $X^2$ is above or equal to 1; the net charge of $X^4$ is below or equal to 0; $X^1$ defines a sequence of 1 or 2 amino acids with a positive charge; and $X^3$ defines a sequence of 2, 3 or 4 amino acid independently selected from any basic amino acid, citrulline, tryptophan, or a derivative thereof.

In some embodiments the basic amino acid is independently selected from Arg, Lys, and His.

In some embodiments $X^2$ and/or $X^4$ comprises the sequence of amino acids defined by position 135-157 of SEQ ID NO:3, or a fragment or variant thereof.

In some embodiments $X^2$ and/or $X^4$ consist of a sequence selected from GYIPLVGAPLG, GYLPAVGAPIG, GYLPAVGAPI, NYVTGNIPG, NYATGNLPG, NYATGNLPG, VTGNIPGSTYS, IRNLGRVIETLTG, SRNLGKVIDTLTC, IRNLGRVIETLT, GGGQIIGGNYLIP, GGGQIVGGVYLLP, LIFLARSALIV, LIFLARSALIL, LIFLARSALIL, SAYERMCNIL, SAYERZVNIL, TAYERZCNIL, IAYERMCNIL, IAYERMCNIL, LFFKCIYRLFKHGL, LFFKTITRLFBHGL, GLEPLVIAGILA, GSDPLVVAASIV, NLVPMVATV, NLVPMVATV, NIVPZVVTA, PEVIPMFSALS, FIIPXFTALSG, ALGPAATL, GPVVHLTL, LECVYCKQQLL, GVYDFAFRDLC, GVFDYAFRDIN, GATPVDLLGA, GVTPAGLIGV, VARALAHGVRV, VIRVIAHGLRL, GITFSIFLIVS, CSFSIFLLAL, GCSFSIFLLAL, GITFSIYLIVS, LZGYIPLIGA, LMGYIPLVGA, LZGYIPLIGA, PBIGVRATB, GPRLGVRATR, GPRLGVRAT, RGSVAHKS, SALILRGSVAHK, FQTAAQRAMM, FQTAAQRAVZ, FQTVVQBA, FQTAAQRA, GPSTEGVPESM, LLSTEGVPNSZ, GSLVGLLHIVL, ASIVGILHLIL, NLVPMVATV, NIVPZVVTA, TPQDLNTMLN, ALLYGATPYAIG, MMTACQGVG, GQAGDDFS, EVYDFAFRDLC, GFAFRDLCIVY, GFAYRDINLAY, GALNLCLPM, and GALQIBLPL, IRNLGRVIETLTLZGYIPLIGA, or a fragment or variant thereof.

In some embodiments $X^2$ and/or $X^4$ consist of a sequence derived from an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, 1.0 SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:126, and SEQ ID NO:198, or a fragment or variant thereof.

In some embodiments the peptide according to the invention is selected from RRGYIPLVGAPLGBGRVARALAHGVRV, RGYIPLVGAPLGRRVARALAHGVRV, RGYIPLVGAPLGRRRVARALAHGVRVR, RRGYIPLVGAPLGRRVARALAHGVRV, RRGYIPLVGAPLGRRRVARALAHGVRV, BRGYIPLVGAPLGRRVARALAHGVRV, RRRGYIPLVGAPLGBRVARALAHGVRV, RGYIPLVGAPLGKKKVARALAHGVRV, RGYIPLVGAPLGRRRVARALAHGVRV, KKGYIPLVGAPLGKKVARALAHGVRV, WGYIPLVGAPLGRRVARALAHGVRV, WWGYIPLVGAPLGRRVARALAHGVRV, EEGYIPLVGAPLGEEVARALAHGVRV, GGGYIPLVGAPLGGGVARALAHGVRV, EEGYIPLVGAPLGRRVARALAHGVRV, RRGYIPLVGAPLGLRRVARALAHGVRV, WWGYIPLVGAPLGRRVARALAHGVRV, WWGYIPLVGAPLGRRRVARALAHGVRV, WWGYIPLVGAPLGRVARALAHGVRV, RGYIPLVGAPLGRRVARALAHGVRV, RRGYLPAVGAPIGBRVIRVIAHGLRL, RRGYIPLVGAPLGBRVARALAHGVRV, GYIPLVGAPLGGVARALAHGVRV, WWGYLPAVGAPIRRVIRVIAHGLRL, GYIPLVGAPLGGVARALAHGVRV, RRGYIPLVGAPLGBGRVARALAHGVRV, RGYIPLVGAPLGRRVARALAHGVRV, RGYIPLVGAPLGRRRVARALAHGVRV, RRGYIPLVGAPLGRRVARALAHGVRV, RRGYIPLVGAPLGRRRVARALAHGVRV, BRGYIPLVGAPLGRRVARALAHGVRV, RRRGYIPLVGAPLGBRVARALAHGVRV, RGYIPLVGAPLGKKKVARALAHGVRV, RGYIPLVGAPLGRRRVARALAHGVRV, KKGYIPLVGAPLGKKVARALAHGVRV, WGYIPLVGAPLGRRVARALAHGVRV, WWGYIPLVGAPLGRRVARALAHGVRV, RRGYIPLVGAPLGLRRVARALAHGVRV, RRNYVTGNIPGBRGITFSIFLIVS, WWNYATGNLPGRRCSFSIFLLAL, WWNYVTGNIPGBRGITFSIFLIVS, WWNYVTGNIPGRRGITFSIFLIVS, RRNYATGNLPGRRGCSFSIFLLAL, RRVTGNIPGSTYSGBRGITFSIYLIVS, RRIRNLGRVIETLTGBRLZGYIPLIGA, RRSRNLGKVIDTLTCBRLMGYIPLVGA, SRNLGKVIDTLTCGFADLMGYIPLVGA, WWIRNLGRVIETLTRRLZGYIPLIGA, WWSRNLGKVIDTLTCRRLMGYIPLVGA, RRGGGQIIGGNYLIPRBPBIGVRATB, GGGQIVGGVYLLPRRGPRLGVRATR, RRGGGQIVGGVYLLPRRGPRLGVRATR, WWGGGQIVGGVYLLPRRGPRLGVRAT, BRLIFLARSALIVRGSVAHKS, EDLIFLARSALILRGSVAHKS, BRLIFLARSALILBGRSALILRGSVAHK, SAYERMCNILKGKFQTAAQRAMM, SAYERZVNILKGKFQTAAQRAVZ, BRTAYERZCNILBRGRFQTWQBA, BRIAYERMCNILLBRGKFQTAAQRA, IAYERMCNILKGKFQTAAQRA, LFFKCIYRLFKHGLKRGPSTEGVPESM, BRRLFFKTITRLFBHGLRRLLSTEGVPNSZ, BRGLEPLVIAGILARRGSLVGLLHIVL, BRGSDPLVVAASIVRRASIVGILHLIL, RNLVPMVATVRRNLVPMVATVB, RNLVPMVATVBRRNLVPMVATVB, RNIVPZVVTARRNIVPZVVTAB, PEVIPMFSALSEGATPQDLNTMLN, RFIIPXFTALSGGRRALLYGATPYAIG, KALGPAATLEEMMTACQGVG, RRGPVVHLTLRRRGQAGDDFS, RRGPWHLTLRRRGQAGDDFS, RRGPVVHLTLRGRRGQAGDDFS, RRLECVYCKQQLLRREVYDFAFRDLC, RRGVYDFAFRDLCRRGFAFRDLCIVYR, RRGVFDYAFRDINRRGFAYRDINLAYR, RRGATPVDLLGARRGALNLCLPMR, RRGVTPAGLIGVRRGALQIBLPLR, RGYLPAVGAPIGRRRVIRVIAHGLRLR, RRSRNLGKVIDTLTCRRLMGYIPLVGA, RRIRNLGRVIETLTLZGYIPLIGARRIRNLGRVIETLTLZGYIPLIGAR, or a fragment or variant thereof.

In some embodiments the peptide consist of a sequence selected from $X^1$-NYVTGNIPG-$X^3$-GITFSIYLIVS; $X^1$-IRNLGRVIETLT-$X^3$-LZGYIPLIGA; $X^1$-GYLPAVGAPI-$X^3$-VIRVIAHGLRL; $X^1$-GGGQIIGGNYLIP-$X^3$-PBIGVRATB; $X^1$-NYATGNLPG-$X^3$-GCSFSIFLLAL; $X^1$-SRNLGKVIDTLTC-$X^3$-LMGYIPLVGA; $X^1$-GYIPLVGAPL-$X^3$-VARALAHGVRV; $X^1$-GGGQIVGGVYLLP-$X^3$-PRLGVRATR; $X^1$-LTFLVRSVLLI-$X^3$-GSVLIVRGSLVH; $X^1$-TAYERZCNIL-$X^3$-GRFQTVVQBA; $X^1$-SDPLVVAASIV-$X^3$-ASIVGILHLIL; $X^1$-LIFLARSALIL-$X^3$-SALILRGSVAH; $X^1$-IAYERMCNIL-$X^3$-GKFQTAAQRA; and $X^1$-LEPLVIAGILA-$X^3$-GSLVGLLHIVL; $X^1$-NLVPMVATV-$X^3$-NLVPMATV; $X^1$-GYLPAVGAPIG-$X^3$-VIRVIAHGLRL; $X^1$-IRNLGRVIETLTG-$X^3$-LZGYIPLIGA; $X^1$-GVYDFAFRDLC-$X^3$-GFAFRDLCIVYR, $X^1$-GVFDYAFRDIN-$X^3$-GFAYRDINLAYR, $X^1$-GATPVDLLGA-$X^3$-GALNLCLPMR, $X^1$-GVTPAGLIGV-$X^3$-GALQIBLPLR, and $X^1$-IRNLGRVIETLTLZGYIPLIGA-$X^3$-IRNLGRVIETLTLZGYIPLIGA; optionally with an $X^5$ in the C-terminal of the peptide wherein $X^1$, $X^3$ and $X^5$ refers to $X^1$, $X^3$, and $X^5$ of formula I.

In some embodiments the peptide comprises one or more cysteine.

In some embodiments the peptide contain intramolecular bonds, such as intramolecular disulfide (S—S) bonds between two cys residues.

In other embodiments the peptide contains intramolecular bonds, such as in the form of a acylal moiety (COO—CH2-OOC, COO—CHR—OOC or COO—CR2-OOC).

In some embodiments the N- and/or C-terminal amino acid in $X^2$ is a hydrophilic or polar amino acid.

In some embodiments the N-terminal amino acid in $X^4$ is a hydrophilic or polar amino acid.

In some embodiments the peptide according to the invention is not more than 58 amino acids, such as not more than 56, 54, 52, 50, 48, 46, 44, 42, 40, 38, 36, 34, 32, 30, 28, 26, 24, 22, 20, 18 amino acid residues.

In some embodiments $X^1$ consist of 2 or 3 amino acids.

In some embodiments $X^1$ consist of WW, BR, or RR.

In some embodiments $X^1$ consist of R, or W.

In some embodiments $X^3$ consist of 2 or 3 amino acids.

In some embodiments $X^3$ consist of WW, BR, or RR.

In some embodiments $X^3$ consist of RRR, BRR, or BRGR.

In some embodiments an isolated peptide according to the invention consists of a sequence of $X^2$ or $X^4$ as defined in table 1 or in table 2.

In some embodiments an isolated peptide according to the invention comprises a sequence of $X^2$ and/or $X^4$ as defined in table 1 or in table 2, or a fragment thereof.

In some embodiments $X^2$ defines a sequence of 8-25 amino acids, such as 8-20 amino acids, such as 8-15 amino acids, such as 8-11 amino acids.

In some embodiments $X^2$ defines a sequence of less than 25, such as less than 24, 23, 22, 21, 20, 19, 18, 17, 16, 15, 14, 13, 12, 11, 10, 9, 8, 7 or 6 amino acids.

In some embodiments $X^2$ defines a sequence of more than 8, such as more than 9, 10, 11, 12, 13, 14, 15, 16, 17, 18, 19, 20, 21, 22, 23, 24, 25, 26, 27, 28, 29 amino acids.

In some embodiments $X^4$ defines a sequence of 8-25 amino acids, such as 8-20 amino acids, such as 8-15 amino acids, such as 8-11 amino acids.

In some embodiments $X^4$ defines a sequence of less than 25, such as less than 24, 23, 22, 21, 20, 19, 18, 17, 16, 15, 14, 13, 12, 11, 10, 9, 8, 7 or 6 amino acids.

In some embodiments $X^4$ defines a sequence of more than 8, such as more than 9, 10, 11, 12, 13, 14, 15, 16, 17, 18, 19, 20, 21, 22, 23, 24, 25, 26, 27, 28, 29 amino acids.

In some embodiments the dimer peptide according to the invention consist of two identical peptide monomers.

In some embodiments the immunogenic composition according to the invention is in the form of a vaccine composition.

In some embodiments, the cell-penetrating peptide of the invention comprises at most 60, at most 59, at most 58, at most 57, at most 56, at most 55, at most 54, at most 53, at most 52, at most 51, at most 50, at most 49, at most 48, at most 47, at most 46, at most 45, at most 44, at most 43, at most 42, at most 41, at most 40, at most 39, at most 38, at most 37, at most 36, at most 35, at most 34, at most 33, at most 32, at most 31, at most 30, at most 29, at most 28, at most 27, at most 26, at most 25, at most 24, at most 23, at most 22, at most 21, at most 20, at most 19, at most 18 amino acids.

In some embodiments, the cell-penetrating peptide of the invention comprises at least 18, at least 19, at least 20, at least 21, at least 22, at least 23, at least 24, at least 25, at least 26, at least 27, at least 28, at least 29, at least 30, at least 31, at least 32, at least 33, at least 34, at least 35 at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60 amino acid residues.

In some embodiments, the cell-penetrating peptide of the invention consists of 18 amino acid residues or 19 amino acid residues or 20 amino acid residues or 21 amino acid residues or 22 amino acid residues or 23 amino acid residues or 24 amino acid residues or 25 amino acid residues or 26 amino acid residues or 27 amino acid residues or 28 amino acid residues or 29 amino acid residues or 30 amino acid residues or 31 amino acid residues or 32 amino acid residues or 33 amino acid residues or 34 amino acid residues or 35 amino acid residues or 36 amino acid residues or 37 amino acid residues or 38 amino acid residues or 39 amino acid residues or 40 amino acid residues or 41 amino acid residues or 42 amino acid residues or 43 amino acid residues or 44 amino acid residues or 45 amino acid residues or 46 amino acid residues or 47 amino acid residues or 48 amino acid residues or 49 amino acid residues or 50 amino acid residues or 51 amino acid residues or 52 amino acid residues or 53 amino acid residues or 54 amino acid residues or 55 amino acid residues or 56 amino acid residues or 57 amino acid residues or 58 amino acid residues or 59 amino acid residues or 60 amino acid residues.

In some embodiments the cell-penetrating peptide of the invention does not consist of the following sequence RFIIP[Nle]FTALSGGRRALLYGATPYAIG, where Nle denotes a nor-leucine.

In some embodiments $X^2$ and/or $X^4$ is not derived from HIV.

In some embodiments $X^4$ is a linear sequence of less than 12 amino acids.

In some embodiments $X^2$ is a linear sequence of less than 12 amino acids.

In some embodiments $X^2$ and/or $X^4$ do not contain nor-leucine.

In some embodiments $X^2$ do not contain nor-leucine.

In some embodiments $X^2$ and/or $X^4$ only contains natural amino acids.

In some embodiments $X^2$ only contains natural amino acids.

In some embodiments $X^2$ only contains natural amino acids if derived from HIV.

In some embodiments $X^2$ and/or $X^4$ is derived from HCV, CMV, HPV, Influenza, adenoviruses, or picornaviruses.

Numbered embodiments according to the invention:

1. An isolated cell-penetrating peptide comprising the following structure $$X^1\text{-}X^2\text{-}X^3\text{-}X^4\text{-}X^5 \quad \text{(formula I)},$$

wherein $X^1$ and $X^3$ independently defines a linear sequence of any 1, 2, 3 or 4 amino acid independently selected from any basic amino acid, citrulline, tryptophan, or a derivative thereof; $X^2$ defines a linear sequence of 8-30 amino acids derived from an antigen; $X^4$ defines a linear sequence of 8-30 amino acids derived from said antigen, said sequence $X^4$ being different from $X^2$; and wherein $X^5$ is any one optional amino acid selected from a basic amino acid, citrulline, tryptophan, or a derivative thereof.

2. The isolated peptide according to embodiment 1, wherein $X^1$ defines a linear sequence of any 1, 2, 3, or 4 amino acids independently selected from any basic amino acid, tryptophan, or a derivative thereof.

3. The isolated peptide according to embodiment 1, wherein $X^1$ defines a linear sequence in any order of one citrulline and any 1, 2, or 3 amino acids independently selected from any basic amino acid, tryptophan, or a derivative thereof.

4. The isolated peptide according to any one of embodiment 1-3, wherein $X^3$ defines a linear sequence of any 1, 2, 3, or 4 amino acids independently selected from any basic amino acid.

5. The isolated peptide according to any one of embodiment 1-3, wherein $X^3$ defines a linear sequence in any order of one citrulline and of any 1, 2, or 3 amino acids independently selected from any basic amino acid.

6. The isolated peptide according to any one of embodiment 1-5, wherein the sequence of amino acids defined by $X^2$-$X^3$-$X^4$ of formula I as defined in embodiment 1 is not found in the native sequence of said antigen.

7. The isolated peptide according to any one of embodiment 1-6, wherein said peptide is demonstrated to translocate across a plasma membrane in the assay based on biotinylation of peptides as described in example 1.

8. The isolated peptide according to any one of embodiments 1-7, wherein said one optional amino acid selected from a basic amino acid, citrulline, tryptophan, or a derivative thereof is selected from Arg, Lys, and His.

9. The isolated peptide according to any one of embodiments 1-8, wherein $X^2$ and/or $X^4$ defines a sequence identical to the native sequence of said antigen.

10. The isolated peptide according to any one of embodiments 1-9, wherein said peptide is capable of inducing a T lymphocyte response.

11. The isolated peptide according to any one of embodiments 1-10, wherein said antigen is a viral protein, such as a capsid protein.

12. The isolated peptide according to embodiment 11, wherein said viral protein is selected from a protein of the Hepatitis C virus, such as a core protein; protein of influenza virus, such as an M2 protein.

13. The isolated peptide according to embodiment 11, wherein said viral protein of Hepatitis C virus is selected from HCV consensus sequence of genotype 1, such as subtypes 1a and 1b, genotype 2 such as 2a and 2b and genotype 3, such as 3a.

14. The isolated peptide according to any one of embodiments 1-13, which cell-penetrating peptide is of 19-60 amino acids, such as of 20-60 amino acids, such as of 21-60 amino acids, such as of 22-60 amino acids, such as of 23-60 amino acids, such as of 24-60 amino acids, such as of 25-60 amino acids, such as of 26-60 amino acids, such as of 27-60 amino acids, such as of 28-60 amino acids, such as of 29-60 amino acids, such as of 30-60 amino acids, such as of 31-60 amino acids, such as of 32-60 amino acids, such as of 33-60 amino acids, such as of 34-60 amino acids, such as of 35-60 amino acids.

15. The isolated peptide according to any one of embodiments 1-14, which cell-penetrating peptide is of 18-60, such as 18-59, such as 18-58, such as 18-57, such as 18-56, such as 18-55, such as 18-54, such as 18-53, such as 18-52, such as 18-51, such as 18-50, such as 18-49, such as 18-48, such as 18-47, such as 18-46, such as 18-45, such as 18-44, such as 18-43, such as 18-42, such as 18-41, such as 18-40, such as 18-39, such as 18-38, such as 18-37, such as 18-35 amino acids, such as of 18-34 amino acids, such as of 18-33 amino acids, such as of 18-32 amino acids, such as of 18-31 amino acids, such as of 18-30 amino acids, such as of 18-29 amino acids, such as of 18-28 amino acids, such as of 18-27 amino acids, such as of 18-26 amino acids, such as of 18-25 amino acids, such as of 18-24 amino acids, such as of 18-23 amino acids, such as of 18-22 amino acids, such as of 18-21 amino acids, such as of 18-20 amino acids, such as of 18-19 amino acids.

16. The isolated peptide according to any one of embodiments 1-15, wherein the net charge of $X^2$ is below or equal to 0; and wherein $X^1$ and $X^3$ defines a sequence of 2, 3 or 4 amino acid independently selected from any basic amino acid, citrulline, tryptophan, or a derivative thereof.

17. The isolated peptide according to any one of embodiments 1-16, wherein the net charge of $X^2$ is below or equal to 0; wherein the net charge of $X^4$ is above or equal to 1; and wherein $X^1$ and $X^3$ defines a sequence of 2, 3 or 4 amino acid independently selected from any basic amino acid, citrulline, tryptophan, or a derivative thereof.

18. The isolated peptide according to any one of embodiments 1-17, wherein the net charge of $X^2$ and $X^4$ are below or equal to 0 and wherein $X^1$ and $X^3$ defines a sequence of 2, 3 or 4 amino acid independently selected from any basic amino acid, citrulline, tryptophan, or a derivative thereof.

19. The isolated peptide according to any one of embodiments 1-18, wherein the net charge of $X^2$ and $X^4$ are above or equal to 1 and wherein $X^1$ and $X^3$ defines a sequence of 1 or 2 amino acid independently selected from any basic amino acid, citrulline, tryptophan, or a derivative thereof.

20. The isolated peptide according to any one of embodiments 1-19, wherein the net charge of $X^2$ is above or equal to 1; wherein the net charge of $X^4$ is below or equal to 0; wherein $X^1$ defines a sequence of 1 or 2 amino acids with a positive charge; and wherein $X^3$ defines a sequence of 2, 3 or 4 amino acid independently selected from any basic amino acid, citrulline, tryptophan, or a derivative thereof.

21. The isolated peptide according to any one of embodiments 1-20, wherein said basic amino acid is independently selected from Arg, Lys, and His.

22. The isolated peptide according to any one of embodiments 1-21, wherein $X^2$ and/or $X^4$ comprises the sequence of amino acids defined by position 135-157 of SEQ ID NO:3, or a fragment or variant thereof.

23. The isolated peptide according to any one of embodiments 1-22, wherein $X^2$ and/or $X^4$ consist of a sequence selected from GYIPLVGAPLG, GYLPAVGAPIG, GYLPAVGAPI, NYVTGNIPG, NYATGNLPG, NYATGNLPG, VTGNIPGSTYS, IRNLGRVIETLTG, SRNLGKVIDTLTC, IRNLGRVIETLT, GGGQIIGGNYLIP, GGGQIVGGVYLLP, LIFLARSALIV, LIFLARSALIL, LIFLARSALIL, SAYERMCNIL, SAYERZVNIL, TAYERZCNIL, IAYERMCNIL, IAYERMCNIL, LFFKCIYRLFKHGL, LFFKTITRLFBHGL, GLEPLVIAGILA, GSDPLVVAASIV, NLVPMVATV, NLVPMVATV, NIVPZVVTA, PEVIPMFSALS, FIIPXFTALSG, ALGPAATL, GPWHLTL, LECVYCKQQLL, GVYDFAFRDLC, GVFDYAFRDIN, GATPVDLLGA, GVTPAGLIGV, VARALAHGVRV, VIRVIAHGLRL, GITFSIFLIVS, CSFSIFLLAL, GCSFSIFLLAL, GITFSIYLIVS, LZGYIPLIGA, LMGYIPLVGA, LZGYIPLIGA, PBIGVRATB, GPRLGVRATR, GPRLGVRAT, RGSVAHKS, SALILRGSVAHK, FQTAAQRAMM, FQTAAQRAVZ, FQTVVQBA, FQTAAQRA, GPSTEGVPESM, LLSTEGVPNSZ, GSLVGLLHIVL, ASIVGILHLIL, NLVPMVATV, NIVPZVVTA, TPQDLNTMLN, ALLYGATPYAIG, MMTACQGVG, GQAGDDFS, EVYDFAFRDLC, GFAFRDLCIVY, GFAYRDINLAY, GALNLCLPM, GALQIBLPL, and IRNLGRVIETLTLZGYIPLIGA, or a fragment or variant thereof.

24. The isolated peptide according to any one of embodiments 1-23, wherein $X^2$ and/or $X^4$ consist of a sequence derived from an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:126, and SEQ ID NO:198, or a fragment or variant thereof.

25. The isolated peptide according to any one of embodiments 1-24, wherein said peptide is selected from RRGYIPLVGAPLGBGRVARALAHGVRV (SEQ ID NO:47), RGYIPLVGAPLGRRVARALAHGVRV (SEQ ID NO:48), RGYIPLVGAPLGRRRVARALAHGVRVR (SEQ ID NO:49), RRGYIPLVGAPLGRRVARALAHGVRV (SEQ ID NO:50), RRGYIPLVGAPLGRRRVARALAHGVRV (SEQ ID NO:51), BRGYIPLVGAPLGRRVARALAHGVRV (SEQ ID NO:52), RRRGYIPLVGAPLGBRVARALAHGVRV (SEQ ID NO:53), RGYIPLVGAPLGKKKVARALAHGVRV (SEQ ID NO:54), RGYIPLVGAPLGRRRVARALAHGVRV (SEQ ID NO:55), KKGYIPLVGAPLGKKVARALAHGVRV (SEQ ID NO:56), WGYIPLVGAPLGRRVARALAHGVRV (SEQ ID NO:57), WWGYIPLVGAPLGRRVARALAHGVRV (SEQ ID NO:58), EEGYIPLVGAPLGEEVARALAHGVRV (SEQ ID NO:59), GGGYIPLVGAPLGGGVARALAHGVRV (SEQ ID NO:60), EEGYIPLVGAPLGRRVARALAHGVRV (SEQ ID NO:61), RRGYIPLVGAPLGLRRVARALAHGVRV (SEQ ID NO:62), WWGYIPLVGAPLGRRVARALAHGVRV (SEQ ID NO:63), WWGYIPLVGAPLGRRRVARALAHGVRV (SEQ ID NO:64), WWGYIPLVGAPLGRVARALAHGVRV (SEQ ID NO:65), RGYIPLVGAPLGRRVARAL- AHGVRV (SEQ ID NO:66), RRGYLPAVGAPIGBRVIRVIAHGLRL (SEQ ID NO:67), RRGYIPLVGAPLGBRVARALAHGVRV (SEQ ID NO:68), GYIPLVGAPLGGVARALAHGVRV (SEQ ID NO:69), WWGYLPAVGAPIRRVIRVIAHGLRL (SEQ ID NO:70), GYIPLVGAPLGGVARALAHGVRV (SEQ ID NO:71), RRGYIPLVGAPLGBGRVARALAHGVRV (SEQ ID NO:72), RGYIPLVGAPLGRRVARALAHGVRV (SEQ ID NO:73), RGYIPLVGAPLGRRRVARALAHGVRV (SEQ ID NO:74), RRGYIPLVGAPLGRRVARALAHGVRV (SEQ ID NO:75), RRGYIPLVGAPLGRRRVARALAHGVRV (SEQ ID NO:76), BRGYIPLVGAPLGRRVARALAHGVRV (SEQ ID NO:77), RRRGYIPLVGAPLGBRVARALAHGVRV (SEQ ID NO:78), RGYIPLVGAPLGKKKVARALAHGVRV (SEQ ID NO:79), RGYIPLVGAPLGRRRVARALAHGVRV (SEQ ID NO:80), KKGYIPLVGAPLGKKVARALAHGVRV (SEQ ID NO:81), WGYIPLVGAPLGRRVARALAHGVRV (SEQ ID NO:82), WWGYIPLVGAPLGRRVARALAHGVRV (SEQ ID NO:83), RRGYIPLVGAPLGLRRVARALAHGVRV (SEQ ID NO:84), RRNYVTGNIPGBRGITFSIFLIVS (SEQ ID NO:85), WWNYATGNLPGRRCSFSIFLLAL (SEQ ID NO:86), WWNYVTGNIPGBRGITFSIFLIVS (SEQ ID NO:87), WWNYVTGNIPGRRGITFSIFLIVS (SEQ ID NO:88), RRNYATGNLPGRRGCSFSIFLLAL (SEQ ID NO:89), RRVTGNIPGSTYSGBRGITFSIYLIVS (SEQ ID NO:90), RRIRNLGRVIETLTGBRLZGYIPLIGA (SEQ ID NO:91), RRSRNLGKVIDTLTCBRLMGYIPLVGA (SEQ ID NO:92), SRNLGKVIDTLTCGFADLMGYIPLVGA (SEQ ID NO:93), WWIRNLGRVIETLTRRLZGYIPLIGA (SEQ ID NO:94), WWSRNLGKVIDTLTCRRLMGYIPLVGA (SEQ ID NO:95), RRGGGQIIGGNYLIPRBPBIGVRATB (SEQ ID NO:96), GGGQIVGGVYLLPRRGPRLGVRATR (SEQ ID NO:97), RRGGGQIVGGVYLLPRRGPRLGVRATR (SEQ ID NO:98), WWGGGQIVGGVYLLPRRGPRLGVRAT (SEQ ID NO:99), BRLIFLARSALIVRGSVAHKS (SEQ ID NO:100), EDLIFLARSALILRGSVAHKS (SEQ ID NO:101), BRLIFLARSALILBGRSALILRGSVAHK (SEQ ID NO:102), SAYERMCNILKGKFQTAAQRAMM (SEQ ID NO:103), SAYERZVNILKGKFQTAAQRAVZ (SEQ ID NO:104), BRTAYERZCNILBRGRFQTWQBA (SEQ ID NO:105), BRIAYERMCNILLBRGKFQTAAQRA (SEQ ID NO:106), IAYERMCNILKGKFQTAAQRA (SEQ ID NO:107), LFFKCIYRLFKHGLKRGPSTEGVPESM (SEQ ID NO:108), BRRLFFKTITRLFBHGLRRLLSTEGVPNSZ (SEQ ID NO:109), BRGLEPLVIAGILARRGSLVGLLHIVL (SEQ ID NO:110), BRGSDPLWAASIVRRASIVGILHLIL (SEQ ID NO:111), RNLVPMVATVRRNLVPMVATVB (SEQ ID NO:112), RNLVPMVATVBRRNLVPMVATVB (SEQ ID NO:113), RNIVPZVVTARRNIVPZVVTAB (SEQ ID NO:114), PEVIPMFSALSEGATPQDLNTMLN (SEQ ID NO:115), RFIIPXFTALSGGRRALLYGATPYAIG (SEQ ID NO:116), KALGPAATLEEMMTACQGVG (SEQ ID NO:117), RRGPVVHLTLRRRGQAGDDFS (SEQ ID NO:118), RRGPVVHLTLRRRGQAGDDFS (SEQ ID NO:119), RRGPVVHLTLRGRRGQAGDDFS (SEQ ID NO:120), RRLECVYCKQQLLRREVYDFAFRDLC (SEQ ID NO:121), RRGVYDFAFRDLCRRGFAFRDLCIVYR (SEQ ID NO:122), RRGVFDYAFRDINRRGFAYRDINLAYR (SEQ ID NO:123), RRGATPVDLLGARRGALNLCLPMR (SEQ ID NO:124), RRGVTPAGLIGVRRGALQIBLPLR (SEQ ID NO:125), RGYLPAVGAPIGRRRVIRVIAHGLRLR (SEQ ID NO:196), RRSRNLGKVIDTLTCRRLMGYIPLVGA (SEQ ID NO:197), and RRIRNLGRVIETLTLZGYIPLIGARRIRNLGRVIETLTLZGYIPLIGAR (SEQ ID NO:199), or a fragment or variant thereof.

26. The isolated peptide according to any one of embodiments 1-25, wherein the peptide consist of a sequence selected from $X^1$-NYVTGNIPG-$X^3$-GITFSIYLIVS; $X^1$-IRNLGRVIETLT-$X^3$-LZGYIPLIGA; $X^1$-GYLPAVGAPI-$X^3$-VIRVIAHGLRL; $X^1$-GGGQIIGGNYLIP-$X^3$-PBIGVRATB; $X^1$-NYATGNLPG-$X^3$-GCSFSIFLLAL; $X^1$-SRNLGKVIDTLTC-$X^3$-LMGYIPLVGA; $X^1$-GYIPLVGAPL-$X^3$-VARALAHGVRV; $X^1$-GGGQIVGGVYLLP-$X^3$-PRLGVRATR; $X^1$-LTFLVRSVLLI-$X^3$-GSVLIVRGSLVH; $X^1$-TAYERZCNIL-$X^3$-GRFQTVVQBA; $X^1$-SDPLVVAASIV-$X^3$-ASIVGILHLIL; $X^1$-LIFLARSALIL-$X^3$-SALILRGSVAH; $X^1$-IAYERMCNIL-$X^3$-GKFQTAAQRA; and $X^1$-LEPLVIAGILA-$X^3$-GSLVGLLHIVL; $X^1$-NLVPMVATV-$X^3$-NLVPMATV; $X^1$-GYLPAVGAPIG-$X^3$-VIRVIAHGLRL; $X^1$-IRNLGRVIETLTG-$X^3$-LZGYIPLIGA; $X^1$-GVYDFAFRDLC-$X^3$-GFAFRDLCIVYR, $X^1$-GVFDYAFRDIN-$X^3$-GFAYRDINLAYR, $X^1$-GATPVDLLGA-$X^3$-GALNLCLPMR, $X^1$-GVTPAGLIGV-$X^3$-GALQIBLPLR, and $X^1$-IRNLGRVIETLTLZGYIPLIGA-$X^3$-IRNLGRVIETLTLZGYIPLIGA; optionally with an $X^5$ in the C-terminal of the peptide, wherein $X^1$ and $X^3$ and $X^5$ refers to $X^1$, $X^3$, and $X^5$ of formula I.

27. The isolated peptide according to any one of embodiments 1-26, wherein the peptide comprises one or more cysteine.

28. The isolated peptide according to any one of embodiments 1-27, wherein the peptide contain intramolecular bonds, such as intramolecular disulfide (S—S) bonds between two cys residues or acylals.

29. The isolated peptide according to any one of embodiments 1-28, wherein the N- and/or C-terminal amino acid in $X^2$ is a hydrophilic or polar amino acid.

30. The isolated peptide according to any one of embodiments 1-29, wherein the N-terminal amino acid in $X^4$ is a hydrophilic or polar amino acid.

31. The isolated peptide according to any one of embodiments 1-30, which is not more than 58 amino acids, such as not more than 56, 54, 52, 50, 48, 46, 44, 42, 40, 38, 36, 34, 32, 30, 28, 26, 24, 22, 20, 18 amino acid residues.

32. The isolated peptide according to any one of embodiments 1-31, wherein $X^1$ consist of 2 or 3 amino acids.

33. The isolated peptide according to embodiment 32, wherein $X^1$ consist of WW, BR, or RR.

34. The isolated peptide according to any one of embodiments 1-33, wherein $X^3$ consist of 2 or 3 amino acids.

35. The isolated peptide according to embodiment 34, wherein $X^3$ consist of WW, BR, or RR.

36. Isolated peptide of not more than 60 amino acids comprising a sequence of $X^2$ and/or $X^4$ as independently defined in any one of table 1 or table 2.

37. Isolated peptide according to embodiment 36, which peptide consists of a sequence of $X^2$ or $X^4$ as independently defined in any one of table 1 or table 2.

38. The isolated peptide according to any one of embodiments 1-37, wherein $X^2$ defines a sequence of 8-25 amino acids, such as 8-20 amino acids, such as 8-15 amino acids.

39. The isolated peptide according to any one of embodiments 1-38, wherein $X^4$ defines a sequence of 8-25 amino acids, such as 8-20 amino acids, such as 8-15 amino acids.

40. The isolated peptide according to any one of embodiments 1-39, wherein $X^2$ defines a sequence of less than 25, such as less than 24, 23, 22, 21, 20, 19, 18, 17, 16, 15, 14, 13, 12, 11, 10, 9, 8, 7 or 6 amino acids.

41. The isolated peptide according to any one of embodiments 1-40, wherein $X^2$ defines a sequence of more than 8, such as more than 9, 10, 11, 12, 13, 14, 15, 16, 17, 18, 19, 20, 21, 22, 23, 24, 25, 26, 27, 28, 29 amino acids.

42. The isolated peptide according to any one of embodiments 1-41, wherein $X^4$ defines a sequence of less than 25, such as less than 24, 23, 22, 21, 20, 19, 18, 17, 16, 15, 14, 13, 12, 11, 10, 9, 8, 7 or 6 amino acids.

43. The isolated peptide according to any one of embodiments 1-42, wherein $X^4$ defines a sequence of more than 8, such as more than 9, 10, 11, 12, 13, 14, 15, 16, 17, 18, 19, 20, 21, 22, 23, 24, 25, 26, 27, 28, 29 amino acids.

44. The isolated peptide according to any one of embodiments 1-43, wherein the cell-penetrating peptide of the invention does not consist of the following sequence RFIIP [Nle]FTALSGGRRALLYGATPYAIG, where Nle denotes a nor-leucine.

45. The isolated peptide according to any one of embodiments 1-44, wherein $X^2$ and/or $X^4$ is not derived from HIV.

46. The isolated peptide according to any one of embodiments 1-45, wherein $X^4$ is a linear sequence of less than 12 amino acids.

47. The isolated peptide according to any one of embodiments 1-46, wherein $X^2$ is a linear sequence of less than 12 amino acids.

48. The isolated peptide according to any one of embodiments 1-47, wherein $X^2$ and/or $X^4$ do not contain nor-leucine.

49. The isolated peptide according to any one of embodiments 1-48, wherein $X^2$ do not contain nor-leucine.

50. The isolated peptide according to any one of embodiments 1-49, wherein $X^2$ and/or $X^4$ only contains natural amino acids.

51. The isolated peptide according to any one of embodiments 1-50, wherein $X^2$ only contains natural amino acids.

52. The isolated peptide according to any one of embodiments 1-51, wherein $X^2$ only contains natural amino acids if derived from HIV.

53. The isolated peptide according to any one of embodiments 1-52, wherein $X^2$ and/or $X^4$ is derived from HCV, CMV, HPV, Influenza, adenoviruses, or picornaviruses.

54. Use of a peptide comprising a sequence of $X^2$ or $X^4$ as independently defined in any one of table 1 or table 2 for inducing an immune response in a subject.

55. A dimer peptide comprising two peptides monomers, wherein each peptide monomer is as defined in any one of embodiments 1-53.

56. A dimer peptide according to embodiment 55, wherein the two peptide monomers are identical.

57. Peptide combination comprising two or more peptide according to any one of embodiments 1-53.

58. An isolated nucleic acid or polynucleotide encoding a peptide according to any one of embodiments 1-53.

59. A vector comprising the nucleic acid or polynucleotide according to embodiment 58.

60. A host cell comprising the vector according to embodiment 59.

61. An immunogenic composition comprising at least one peptide according to any one of embodiments 1-53, a dimer peptide according to any one of embodiments 55-56, a peptide combination according to embodiment 57, the nucleic acid or polynucleotide according to embodiment 58, or the vector according to embodiment 59; in combination with a pharmaceutically acceptable diluent or vehicle and optionally an immunological adjuvant.

62. The immunogenic composition according to embodiment 61 in the form of a vaccine composition.

63. A method for inducing an immune response in a subject against an antigen which comprises administration of at least one peptide according to any one of embodiments 1-53, a dimer peptide according to any one of embodiments 55-56, a peptide combination according to embodiment 57, the nucleic acid or polynucleotide according to embodiment 58, or the vector according to embodiment 59; or the composition according to any one of embodiments 61-62.

64. A method for reducing and/or delaying the pathological effects of a virus in a subject infected with said virus, the method comprising administering an effective amount of at least one peptide according to any one of embodiments 1-53, a dimer peptide according to any one of embodiments 55-56, a peptide combination according to embodiment 57, the nucleic acid or polynucleotide according to embodiment 58, or the vector according to embodiment 59; or the composition according to any one of embodiments 61-62.

65. A peptide according to any one of embodiments 1-53 for use as a medicament.

66. A peptide according to any one of embodiments 1-53 for treating the pathological effects of a virus in a subject infected with said virus.

Sequence list (amino acids in bold represents suitable antigenic sequences that may be used as any of $X^2$ and/or $X^4$ as defined in formula I of the present invention)

SEQ ID NO: 1:
Accession no AF009606; Hepatitis C virus subtype 1a polyprotein gene, complete cds.

MSTNPKPQRKTKRNTNRRPQDVKFPGGGQIVGGVYLLPRRGPRL

GVRATRKTSERSQPRGRRQPIPKARRPEGRTWAQPGYPWPLYGNEGCGWAGWLLSPRG

SRPSWGPTDPRRRSRNLGKVIDTLTCGFADLMGYIPLVGAPLGGAARALAHGVRVLED

GVNYATGNLPGCSFSIFLLALLSCLTVPASAYQVRNSSGLYHVTNDCPNSSIVYEAAD

AILHTPGCVPCVREGNASRCWVAVTPTVATRDGKLPTTQLRRHIDLLVGSATLCSALY

VGDLCGSVFLVGQLFTFSPRRHWTTQDCNCSIYPGHITGHRMAWDMMMNWSPTAALVV

AQLLRIPQAIMDMIAGAHWGVLAGIAYFSMVGNWAKVLVVLLLFAGVDAETHVTGGSA

GRTTAGLVGLLTPGAKQNIQLINTNGSWHINSTALNCNESLNTGWLAGLFYQHKFNSS

GCPERLASCRRLTDFAQGWGPISYANGSGLDERPYCWHYPPRPCGIVPAKSVCGPVYC

-continued

FTPSPVVVGTTDRSGAPTYSWGANDTDVFVLNNTRPPLGNWFGCTWMNSTGFTKVCGA

PPCVIGGVGNNTLLCPTDCFRKHPEATYSRCGSGPWITPRCMVDYPYRLWHYPCTINY

TIFKVRMYVGGVEHRLEAACNWTRGERCDLEDRDRSELSPLLLSTTQWQVLPCSFTTL

PALSTGLIHLHQNIVDVQYLYGVGSSIASWAIKWEYVVLLFLLLADARVCSCLWMMLL

ISQAEAALENLVILNAASLAGTHGLVSFLVFFCFAWYLKGRWVPGAVYAFYGMWPLLL

LLLALPQRAYALDTEVAASCGGVVLVGLMALTLSPYYKRYISWCMWWLQYFLTRVEAQ

LHVWVPPLNVRGGRDAVILLMCVVHPTLVFDITKLLLAIFGPLWILQASLLKVPYFVR

VQGLLRICALARKIAGGHYVQMAIIKLGALTGTYVYNHLTPLRDWAENGLRDLAVAVE

PVVFSRMETKLITWGADTAACGDIINGLPVSARRGQEILLGPADGMVSKGWRLLAPIT

AYAQQTRGLLGCIITSLTGRDKNQVEGEVQIVSTATQTFLATCINGVCWTVYHGAGTR

TIASPKGPVIQMYTNVDQDLVGWPAPQGSRSLTPCTCGSSDLYLVTRHADVIPVRRRG

DSRGSLLSPRPISYLKGSSGGPLLCPAGHAVGLFRAAVCTRGVAKAVDFIPVENLETT

MRSPVFTDNSSPPAVPQSFQVAHLHAPTGSGKSTKVPAAYAAQGYKVLVLNPSVAATL

GFGAYMSKAHGVDPNIRTGVRTITTGSPITYSTYGKFLADGGCSGGAYDIIICDECHS

TDATSILGIGTVLDQAETAGARLVVLATATPPGSVTVSHPNIEEVALSTTGEIPFYGK

AIPLEVIKGGRHLIFCHSKKKCDELAAKLVALGINAVAYYRGLDVSVIPTSGDVVVVS

TDALMTGFTGDFDSVIDCNTCVTQTVDFSLDPTFTIETTTLPQDAVSRTQRRGRTGRG

KPGIYRFVAPGERPSGMFDSSVLCECYDAGCAWYELTPAETTVRLRAYMNTPGLPVCQ

DHLEFWEGVFTGLTHIDAHFLSQTKQSGENFPYLVAYQATVCARAQAPPPSWDQMWKC

LIRLKPTLHGPTPLLYRLGAVQNEVTLTHPITKYIMTCMSADLEVVTSTWVLVGGVLA

ALAAYCLSTGCVVIVGRIVLSGKPAIIPDREVLYQEFDEMEECSQHLPYIEQGMMLAE

QFKQKALGLLQTASRQAEVITPAVQTNWQKLEVFWAKHMWNFISGIQYLAGLSTLPGN

PAIASLMAFTAAVTSPLTTGQTLLFNILGGWVAAQLAAPGAATAFVGAGLAGAAIGSV

GLGKVLVDILAGYGAGVAGALVAFKIMSGEVPSTEDLVNLLPAILSPGALVVGVVCAA

ILRRHVGPGEGAVQWMNRLIAFASRGNHVSPTHYVPESDAAARVTAILSSLTVTQLLR

RLHQWISSECTTPCSGSWLRDIWDWICEVLSDFKTWLKAKLMPQLPGIPFVSCQRGYR

GVWRGDGIMHTRCHCGAEITGHVKNGTMRIVGPRTCRNMWSGTFPINAYTTGPCTPLP

APNYKFALWRVSAEEYVEIRRVGDFHYVSGMTTDNLKCPCQIPSPEFFTELDGVRLHR

FAPPCKPLLREEVSFRVGLHEYPVGSQLPCEPEPDVAVLTSMLTDPSHITAEAAGRRL

ARGSPPSMASSSASQLSAPSLKATCTANHDSPDAELIEANLLWRQEMGGNITRVESEN

KVVILDSFDPLVAEEDEREVSVPAEILRKSRRFARALPVWARPDYNPPLVETWKKPDY

EPPVVHGCPLPPPRSPPVPPPRKKRTVVLTESTLSTALAELATKSFGSSSTSGITGDN

TTTSSEPAPSGCPPDSDVESYSSMPPLEGEPGDPDLSDGSWSTVSSGADTEDVVCCSM

SYSWTGALVTPCAAEEQKLPINALSNSLLRHHNLVYSTTSRSACQRQKKVTFDRLQVL

DSHYQDVLKEVKAAASKVKANLLSVEEACSLTPPHSAKSKFGYGAKDVRCHARKAVAH

INSVWKDLLEDSVTPIDTTIMAKNEVFCVQPEKGGRKPARLIVFPDLGVRVCEKMALY

DVVSKLPLAVMGSSYGFQYSPGQRVEFLVQAWKSKKTPMGFSYDTRCFDSTVTESDIR

TEEAIYQCCDLDPQARVAIKSLTERLYVGGPLTNSRGENCGYRRCRASGVLTTSCGNT

LTCYIKARAACRAAGLQDCTMLVCGDDLVVICESAGVQEDAASLRAFTEAMTRYSAPP

GDPPQPEYDLELITSCSSNVSVAEDGAGKRVYYLTRDPTTPLARAAWETARHTPVNSW

LGNIIMFAPTLWARMILMTHFFSVLIARDQLEQALNCEIYGACYSIEPLDLPPIIQRL

-continued

HGLSAFSLHSYSPGEINRVAACLRKLGVPPLRAWRHRARSVRARLLSRGGRAAICGKY

LFNWAVRTKLKLTPIAAAGRLDLSGWFTAGYSGGDIYHSVSHARPRWFWFCLLLLAAG

VGIYLLPNR

SEQ ID NO: 2:
HCV core protein, H77, Accession AF009606
Genbank number: 2316097
>gi|2316098|gb|AAB66324.1| polyprotein [Hepatitis C virus subtype 1a]
MSTNPKPQRKTKRNTNRRPQDVKFPGGGQIVGGVYLLPRRGPRLGVRATRKTSERSQPRGRRQPIPKARR

PEGRTWAQPGYPWPLYGNEGCGWAGWLLSPRGSRPSWGPTDPRRRSRNLGKVIDTLTCGFADLMGYIPLVGAPLGGAAR

ALAHGVRVLEDGVNYATGNLPGCSFSIFLLALLSCLTVPASA

SEQ ID NO: 3:
Hepatitis C virus mRNA, complete cds; ACCESSION M96362
M72423; Hepatitis C virus subtype 1b
MSTNPKPQRKTKRNTNRRPQDIKFPGGGQIVGGVYLLPRRGPRL

GVRATRKTSERSQPRGRRQPIPKARRPEGRAWAQPGYPWPLYGNEGLGWAGWLLSPRG

SRPSWGPTDPRRKSRNLGKVIDTLTCGFADLMGYIPLVGAPLGGVARALAHGVRVLED

GVNYATGNLPGCSFSIFLLALLSCLTTPVSAYEVRNASGMYHVTNDCSNSSIVYEAAD

MIMHTPGCVPCVREDNSSRCWVALTPTLAARNASVPTTTLRRHVDLLVGVAAFCSAMY

VGDLCGSVFLVSQLFTFSPRRHETVQDCNCSIYPGRVSGHRMAWDMMMNWSPTTALVV

SQLLRIPQAVVDMVTGSHWGILAGLAYYSMVGNWAKVLIAMLLFAGVDGTTHVTGGAQ

GRAASSLTSLFSPGPVQHLQLINTNGSWHINRTALSCNDSLNTGFVAALFYKYRFNAS

GCPERLATCRPIDTFAQGWGPITYTEPHDLDQRPYCWHYAPQPCGIVPTLQVCGPVYC

FTPSPVAVGTTDRFGAPTYRWGANETDVLLLNNAGPPQGNWFGCTWMNGTGFTKTCGG

PPCNIGGVGNNTLTCPTDCFRKHPGATYTKCGSGPWLTPRCLVDYPYRLWHYPCTVNF

TIFKVRMYVGGAEHRLDAACNWTRGERCDLEDRDRSELSPLLLSTTEWQVLPCSFTTL

PALSTGLIHLHQNIVDIQYLYGIGSAVVSFAIKWEYIVLLFLLLADARVCACLWMMLL

VAQAEAALENLVVLNAASVAGAHGILSFIVFFCAAWYIKGRLVPGAAYALYGVWPLLL

LLLALPPRAYAMDREMAASCGGAVFVGLVLLTLSPHYKVFLARFIWWLQYLITRTEAH

LQVWVPPLNVRGGRDAIILLTCVVHPELIFDITKYLLAIFGPLMVLQAGITRVPYFVR

AQGLIRACMLARKVVGGHYVQMVFMKLAALAGTYVYDHLTPLRDWAHTGLRDLAVAVE

PVVFSDMETKVITWGADTAACGDIILALPASARRGKEILLGPADSLEGQGWRLLAPIT

AYSQQTRGLLGCIITSLTGRDKNQVEGEVQVVSTATQSFLATCINGVCWTVFHGAGSK

TLAGPKGPITQMYTNVDQDLVGWPAPPGARSLTPCTCGSSDLYLVTRHADVIPVRRRG

DGRGSLLPPRPVSYLKGSSGGPLLCPSGHAVGILPAAVCTRGVAMAVEFIPVESMETT

MRSPVFTDNPSPPAVPQTFQVAHLHAPTGSGKSTRVPAAYAAQGYKVLVLNPSVAATL

GFGAYMSKAHGIDPNLRTGVRTITTGAPITYSTYGKFLADGGGSGGAYDIIMCDECHS

TDSTTIYGIGTVLDQAETAGARLVVLSTATPPGSVTVPHLNIEEVALSNTGEIPFYGK

AIPIEAIKGGRHLIFCHSKKKCDELAAKLSGLGLNAVAYYRGLDVSVIPTSGDVVVVA

TDALMTGFTGDFDSVIDCNTCVTQTVDFSLDPTFTIETTTVPQDAVSRSQRRGRTGRG

RAGIYRFVTPGERPSGMFDSSVLCECYDAGCAWYELTPAETSVRLRAYLNTPGLPVCQ

DHLEFSEGVFTGLTHIDAHFLSQTKQAGENFPYLVAYQATVCARAQAPPPSWDEMWRC

LIRLKPTLHGPTPLLYRLGAVQNEVTLTHPITKFIMTCMSADLEVVTSTWVLVGGVLA

ALAAYCLTTGSVVIVGRIILSGKPAIIPDREVLYQEFDEMEECASHLPYFEQGMQLAE

QFKQKALGLLQTATKQAEAAAPVVESKWRALETFWAKHMWNFISGIQYLAGLSTLPGN

-continued

PAIRSPMAFTASITSPLTTQHTLLFNILGGWVAAQLAPPSAASAFVGAGIAGAAVGTI

GLGKVLVDILAGYGAGVAGALVAFKIMSGEMPSAEDMVNLLPAILSPGALVVGIVCAA

ILRRHVGPGEGAVQWMNRLIAFASRGNHVSPRHYVPESEPAARVTQILSSLTITQLLK

RLHQWINEDCSTPCSSSWLREIWDWICTVLTDFKTWLQSKLLPRLPGVPFFSCQRGYK

GVWRGDGIMHTTCPCGAQITGHVKNGSMRIVGPKTCSNTWYGTFPINAYTTGPCTPSP

APNYSKALWRVAAEEYVEVTRVGDFHYVTGMTTDNVKCPCQVPAPEFFTEVDGVRLHR

YAPACRPLLREEVVFQVGLHQYLVGSQLPCEPEPDVAVLTSMLTDPSHITAETAKRRL

ARGSPPSLASSSASQLSAPSLKATCTTHHDSPDADLIEANLLWRQEMGGNITRVESEN

KVVILDSFDPLRAEDDEGEISVPAEILRKSRKFPPALPIWAPPDYNPPLLESWKDPDY

VPPVVHGCPLPPTKAPPIPPPRRKRTVVLTESTVSSALAELATKTFGSSGSSAIDSGT

ATAPPDQASGDGDRESDVESFSSMPPLEGEPGDPDLSDGSWSTVSEEASEDVVCCSMS

YTWTGALITPCAAEESKLPINPLSNSLLRHHNMVYATTSRSAGLRQKKVTFDRLQVLD

DHYRDVLKEMKAKASTVKAKLLSVEEACKLTPPHSAKSKFGYGAKDVRSLSSRAVTHI

RSVWKDLLEDTETPISTTIMAKNEVFCVQPEKGGRKPARLIVFPDLGVRVCEKMALYD

VVSTLPQAVMGSSYGFQYSPKQRVEFLVNTWKSKKCPMGFSYDTRCFDSTVTENDIRV

EESIYQCCDLAPEAKLAIKSLTERLYIGGPLTNSKGQNCGYRRCRASGVLTTSCGNTL

TCYLKATAACRAAKLRDCTMLVNGDDLVVICESAGTQEDAASLRVFTEAMTRYSAPPG

DPPQPEYDLELITSCSSNVSVAHDASGKRVYYLTRDPTTPLARAAWETARHTPVNSWL

GNIIMYAPTLWARMILMTHFFSILLAQEQLEKTLDCQIYGACYSIEPLDLPQIIERLH

GLSAFSLHSYSPGEINRVASCLRKLGVPPLRAWRHRARSVRAKLLSQGGRAATCGKYL

FNWAVRTKLKLTPIPAASRLDLSGWFVAGYSGGDIYHSLSRARPRWFMLCLLLLSVGV

GIYLLPNR

SEQ ID NO: 4, nucleocapsid protein of influenza A virus

1 MASQGTKRSY EQMETSGERQ NATEIRASVG RMVGGIGRFY IQMCTELKLS DHEGRLIQNS

61 ITIERMVLSA FDERRNKYLE EHPSAGKDPK KTGGPIYRRR DGKWMRELIL YDKEEIRRIW

121 RQANNGEDAT AGLTHMMIWH SNLNDATYQR TRALVRTGMD PRMCSLMQGS TLPRRSGAAG

181 AAVKGVGTMV MELIRMIKRG INDRNFWRGE NGRRTRIAYE RMCNILKGKF QTAAQRAMMD

241 QVRESRNPGN AEIEDLIFLA RSALILRGSV AHKSCLPACV YGLAVASGYD FEREGYSLVG

301 IDPFRLLQNS QVFSLIRPNE NPAHKSQLVW MACHSAAFED LRVSSFIRGT RVVPRGQLST

361 RGVQIASNEN METMDSSTLE LRSRYWAIRT RSGGNTNQQR ASAGQISVQP TFSVQRNLPF

421 ERATIMAAFT GNTEGRTSDM RTEIIRMMEN ARPEDVSFQG RGVFELSDEK ATNPIVPSFD

481 MSNEGS

SEQ ID NO: 5

>gi|73919153|ref|YP_308840.1| matrix protein 2 [Influenza A virus (A/New York/392/2004(H3N2))]

MSLLTEVETPIRNEWGCRCNDSSDPLVVAASIIGILHLILWILDRLFFKCVYRLEKHGLKRGPSTEGVPE 70

SMREEYRKEQQNAVDADDSHFVSIELE

SEQ ID NO: 6

>gi|73919147|ref|YP_308843.1| nucleocapsid protein [Influenza A virus (A/New York/392/2004(H3N2))]

MASQGTKRSYEQMETDGDRQNATEIRASVGKMIDGIGRFYIQMCTELKLSDHEGRLIQNSLTIEKMVLSA 70

FDERRNKYLEEHPSAGKDPKKTGGPIYRRVDGKWMRELVLYDKEEIRRIWRQANNGEDATAGLTHIMIWH 140

SNLNDATYQRTRALVRTGMDPRMCSLMQGSTLPRRSGAAGAAVKGIGTMVMELIRMVKRGINDRNFWRGE 210

-continued

NGRKTRSAYERMCNILKGKFQTAAQRAMVDQVRESRNPGNAEIEDLIFLARSALILRGSVAHKSCLPACA 280

YGPAVSSGYDFEKEGYSLVGIDPFKLLQNSQIYSLIRPNENPAHKSQLVWMACHSAAFEDLRLLSFIRGT 350

KVSPRGKLSTRGVQIASNENMDNMGSSTLELRSGYWAIRTRSGGNTNQQRASAGQTSVQPTFSVQRNLPF 420

EKSTIMAAFTGNTEGRTSDMRAEIIRMMEGAKPEEVSFRGRGVFELSDEKATNPIVPSFDMSNEGSYFFG 490

DNAEEYDN

--

SEQ ID NO: 7

>gi|56583270|ref|NP_040979.2| matrix protein 2 [Influenza A virus (A/Puerto Rico/8/34(H1N1))]

MSLLTEVETPIRNEWGCRCNGSSDPLAIAANIIGILHLILWILDRLFFKCIYRRFKYGLKGGPSTEGVPK

SMREEYRKEQQSAVDADDGHFVSIELE

SEQ ID NO: 8

>gi|8486130|ref|NP_040982.1| nucleocapsid protein [Influenza A virus (A/Puerto Rico/8/34(H1N1))]

MASQGTKRSYEQMETDGERQNATEIRASVGKMIGGIGRFYIQMCTELKLSDYEGRLIQNSLTIERMVLSA

FDERRNKYLEEHPSAGKDPKKTGGPIYRRVNGKWMRELILYDKEEIRRIWRQANNGDDATAGLTHMMIWH

SNLNDATYQRTRALVRTGMDPRMCSLMQGSTLPRRSGAAGAAVKGVGTMVMELVRMIKRGINDRNFWRGE

NGRKTRIAYERMCNILKGKFQTAAQKAMMDQVRESRDPGNAEFEDLTFLARSALILRGSVAHKSCLPACV

YGPAVASGYDFEREGYSLVGIDPFRLLQNSQVYSLIRPNENPAHKSQLVWMACHSAAFEDLRVLSFIKGT

KVVPRGKLSTRGVQIASNENMETMESSTLELRSRYWAIRTRSGGNTNQQRASAGQISIQPTFSVQRNLPF

DRTTVMAAFTGNTEGRTSDMRTEIIRMMESARPEDVSFQGRGVFELSDEKAASPIVPSFDMSNEGSYFFG

DNAEEYDN

--

SEQ ID NO: 9

>gi|73912687|ref|YP_308853.1| membrane protein M2 [Influenza A virus (A/Korea/426/68(H2N2))]

MSLLTEVETPIRNEWGCRCNDSSDPLVVAASIIGILHFILWILDRLFFKCIYRFFKHGLKRGPSTEGVPE

SMREEYRKEQQSAVDADDSHFVSIELE

SEQ ID NO: 10

>gi|73921307|ref|YP_308871.1| nucleoprotein [Influenza A virus (A/Korea/426/68(H2N2))]

MASQGTKRSYEQMETDGERQNATEIRASVGKMIDGIGRFYIQMCTELKLSDYEGRLIQNSLTIERMVLSA

FDERRNKYLEEHPSAGKDPKKTGGPIYKRVDGKWMRELVLYDKEEIRRIWRQANNGDDATAGLTHMMIWH

SNLNDTTYQRTRALVRTGMDPRMCSLMQGSTLPRRSGAAGAAVKGVGTMVMELIRMIKRGINDRNFWRGE

NGRKTRSAYERMCNILKGKFQTAAQRAMMDQVRESRNPGNAEIEDLIFLARSALILRGSVAHKSCLPACV

YGPAIASGYNFEKEGYSLVGIDPFKLLQNSQVYSLIRPNENPAHKSQLVWMACNSAAFEDLRVLSFIRGT

KVSPRGKLSTRGVQIASNENMDTMESSTLELRSRYWAIRTRSGGNTNQQRASAGQISVQPAFSVQRNLPF

DKPTIMAAFTGNTEGRTSDMRAEIIRMMEGAKPEEMSFQGRGVFELSDEKATNPIVPSFDMSNEGSYFFG

DNAEEYDN

SEQ ID NO: 11

>gi|330647|gb|AAA45994.1| pp65 [Human herpesvirus 5]

MASVLGPISGHVLKAVFSRGDTPVLPHETRLLQTGIHVRVSQPSLILVSQYTPDSTPCHRGDNQLQVQHT 70

YFTGSEVENVSVNVHNPTGRSICPSQEPMSIYVYALPLKMLNIPSINVHHYPSAAERKHRHLPVADAVIH 140

ASGKQMWQARLTVSGLAWTRQQNQWKEPDVYYTSAFVFPTKDVALRHVVCAHELVCSMENTRATKMQVIG 210

DQYVKVYLESFCEDVPSGKLFMHVTLGSDVEEDLTMTRNPQPFMRPHERNGFTVLCPKNMIIKPGKISHI 280

MLDVAFTSHEHFGLLCPKSIPGLSISGNLLMNGQQIFLEVQAIRETVELRQYDPVAALFFFDIDLLLQRG 350

PQYSEHPTFTSQYRIQGKLEYRHTWDRHDEGAAQGDDDVWTSGSDSDEELVTTERKTPRVTGGGAMAGAS 420

TSAGRKRKSASSATACTAGVMTRGRLKAESTVAPEEDTDEDSDNEIHNPAVFTWPPWQAGILARNLVPMV 490

ATVQGQNLKYQEFFWDANDIYRIFAELEGVWQPAAQPKRRRHRQDALPGPCIASTPKKHRG 541

-continued

SEQ ID NO: 12

>gi|33330937|gb|AAQ10712.1| putative transforming protein E6 [Human papillomavirus type 16]
MHQKRTAMFQDPQERPGKLPQLCTELQTTIHDIILECVYCKQQLLRREVYDFAFRDLCIVYRDGNPYAVC 70

DKCLKFYSKISEYRHYCYSVYGTTLEQQYNKPLCDLLIRCINCQKPLCPEEKQRHLDKKQRFHNIRGRWT 140

GRCMSCCRSSRTRRETQL

SEQ ID NO: 13

>gi|56583270|ref|NP_040979.2| matrix protein 2 [Influenza A virus (A/Puerto Rico/8/34(H1N1))]
MSLLTEVETPIRNEWGCRCNGSSDPLAIAANIIGILHLILWILDRLFFKCIYRRFKYGLKGGPSTEGVPK

SMREEYRKEQQSAVDADDGHFVSIELE

SEQ ID NO: 14

>gi|8486139|ref|NP_040987.1| PB2 protein [Influenza A virus (A/Puerto Rico/8/34(H1N1))]
MERIKELRNLMSQSRTREILTKTTVDHMAIIKKYTSGRQEKNPALRMKWMMAMKYPITADKRITEMIPER

NEQGQTLWSKMNDAGSDRVMVSPLAVTWWNRNGPMTNTVHYPKIYKTYFERVERLKHGTFGPVHFRNQVK

IRRRVDINPGHADLSAKEAQDVIMEVVFPNEVGARILTSESQLTITKEKKEELQDCKISPLMVAYMLERE

LVRKTRFLPVAGGTSSVYIEVLHLTQGTCWEQMYTPGGEVKNDDVDQSLIIAARNIVRRAAVSADPLASL

LEMCHSTQIGGIRMVDILKQNPTEEQAVGICKAAMGLRISSSFSFGGFTFKRTSGSSVKREEEVLTGNLQ

TLKIRVHEGYEEFTMVGRRATAILRKATRRLIQLIVSGRDEQSIAEAIIVAMVFSQEDCMIKAVRGDLNF

VNRANQRLNPMHQLLRHFQKDAKVLFQNWGVEPIDNVMGMIGILPDMTPSIEMSMRGVRISKMGVDEYSS

TERVVVSIDRFLRVRDQRGNVLLSPEEVSETQGTEKLTITYSSSMMWEINGPESVLVNTYQWIIRNWETV

KIQWSQNPTMLYNKMEFEPFQSLVPKAIRGQYSGFVRTLFQQMRDVLGTFDTAQIIKLLPFAAAPPKQSR

MQFSSFTVNVRGSGMRILVRGNSPVFNYNKATKRLTVLGKDAGTLTEDPDEGTAGVESAVLRGFLILGKE

DRRYGPALSINELSNLAKGEKANVLIGQGDVVLVMKRKRDSSILTDSQTATKRIRMAIN

SEQ ID NO: 15

>gi|8486137|ref|NP_040986.1| polymerase PA [Influenza A virus (A/Puerto Rico/8/34(H1N1))]
MEDFVRQCFNPMIVELAEKTMKEYGEDLKIETNKFAAICTHLEVCFMYSDFHFINEQGESIIVELGDPNA

LLKHRFEIIEGRDRTMAWTVVNSICNTTGAEKPKFLPDLYDYKENRFIEIGVTRREVHIYYLEKANKIKS

EKTHIHIFSFTGEEMATKADYTLDEESRARIKTRLFTIRQEMASRGLWDSFRQSERGEETIEERFEITGT

MRKLADQSLPPNFSSLENFRAYVDGFEPNGYIEGKLSQMSKEVNARIEPFLKTTPRPLRLPNGPPCSQRS

KFLLMDALKLSIEDPSHEGEGIPLYDAIKCMRTFFGWKEPNVVKPHEKGINPNYLLSWKQVLAELQDIEN

EEKIPKTKNMKKTSQLKWALGENMAPEKVDFDDCKDVGDLKQYDSDEPELRSLASWIQNEFNKACELTDS

SWIELDEIGEDVAPIEHIASMRRNYFTSEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQVSRP

MFLYVRTNGTSKIKMKWGMEMRRCLLQSLQQIESMIEAESSVKEKDMTKEFFENKSETWPIGESPKGVEE

SSIGKVCRTLLAKSVFNSLYASPQLEGFSAESRKLLLIVQALRDNLEPGTFDLGGLYEAIEECLINDPWV

LLNASWFNSFLTHALS

SEQ ID NO: 16

>gi|8486133|ref|NP_040984.1| nonstructural protein NS1 [Influenza A virus (A/Puerto Rico/8/34(H1N1))]
MDPNTVSSFQVDCFLWHVRKRVADQELGDAPFLDRLRRDQKSLRGRGSTLGLDIETATRAGKQIVERILK

EESDEALKMTMASVPASRYLTDMTLEEMSREWSMLIPKQKVAGPLCIRMDQAIMDKNIILKANFSVIFDR

LETLILLRAFTEEGAIVGEISPLPSLPGHTAEDVKNAVGVLIGGLEWNDNTVRVSETLQRFAWRSSNENG

RPPLTPKQKREMAGTIRSEV

-continued

SEQ ID NO: 17
>gi|8486132|ref|NP_040983.1| nonstructural protein NS2
[Influenza A virus (A/Puerto Rico/8/34(H1N1))]
MDPNTVSSFQDILLRMSKMQLESSSEDLNGMITQFESLKLYRDSLGEAVMRMGDLHSLQNRNEKWREQLG

QKFEEIRWLIEEVRHKLKVTENSFEQITFMQALHLLLEVEQEIRTFSFQLI

SEQ ID NO: 18
>gi|8486128|ref|NP_040981.1| neuraminidase [Influenza A
virus (A/Puerto Rico/8/34(H1N1))]
MNPNQKIITIGSICLVVGLISLILQIGNIISIWISHSIQTGSQNHTGICNQNIITYKNSTWVKDTTSVIL

TGNSSLCPIRGWAIYSKDNSIRIGSKGDVFVIREPFISCSHLECRTFFLTQGALLNDRHSNGTVKDRSPY

RALMSCPVGEAPSPYNSRFESVAWSASACHDGMGWLTIGISGPDNGAVAVLKYNGIITETIKSWRKKILR

TQESECACVNGSCFTIMTDGPSDGLASYKIFKIEKGKVTKSIELNAPNSHYEECSCYPDTGKVMCVCRDN

WHGSNRPWVSFDQNLDYQIGYICSGVFGDNPRPKDGTGSCGPVYVDGANGVKGFSYRYGNGVWIGRTKSH

SSRHGFEMIWDPNGWTETDSKFSVRQDVVAMTDWSGYSGSFVQHPELTGLDCIRPCFWVELIRGRPKEKT

IWTSASSISFCGVNSDTVDWSWPDGAELPFTIDK

SEQ ID NO: 19
>gi|8486126|ref|NP_040980.1| haemagglutinin [Influenza A
virus (A/Puerto Rico/8/34(H1N1))]
MKANLLVLLCALAAADADTICIGYHANNSTDTVDTVLEKNVTVTHSVNLLEDSHNGKLCRLKGIAPLQLG

KCNIAGWLLGNPECDPLLPVRSWSYIVETPNSENGICYPGDFIDYEELREQLSSVSSFERFEIFPKESSW

PNHNTTKGVTAACSHAGKSSFYRNLLWLTEKEGSYPKLKNSYVNKKGKEVLVLWGIHHPSNSKDQQNIYQ

NENAYVSVVTSNYNRRFTPEIAERPKVRDQAGRMNYYWTLLKPGDTIIFEANGNLIAPRYAFALSRGFGS

GIITSNASMHECNTKCQTPLGAINSSLPFQNIHPVTIGECPKYVRSAKLRMVTGLRNIPSIQSRGLFGAI

AGFIEGGWTGMIDGWYGYHHQNEQGSGYAADQKSTQNAINGITNKVNSVIEKMNIQFTAVGKEFNKLEKR

MENLNKKVDDGFLDIWTYNAELLVLLENERTLDFHDSNVKNLYEKVKSQLKNNAKEIGNGCFEFYHKCDN

ECMESVRNGTYDYPKYSEESKLNREKVDGVKLESMGIYQILAIYSTVASSLVLLVSLGAISFWMCSNGSL

QCRICI

SEQ ID NO: 20
>gi|8486123|ref|NP_040978.1| matrix protein 1 [Influenza
A virus (A/Puerto Rico/8/34(H1N1))]
MSLLTEVETYVLSIIPSGPLKAEIAQRLEDVFAGKNTDLEVLMEWLKTRPILSPLTKGILGFVFTLTVPS

ERGLQRRRFVQNALNGNGDPNNMDKAVKLYRKLKREITFHGAKEISLSYSAGALASCMGLIYNRMGAVTT

EVAFGLVCATCEQIADSQHRSHRQMVTTTNPLIRHENRMVLASTTAKAMEQMAGSSEQAAEAMEVASQAR

QMVQAMRTIGTHPSSSAGLKNDLLENLQAYQKRMGVQMQRFK

SEQ ID NO: 21
>gi|83031685|ref|YP_418248.1| PB1-F2 protein [Influenza
A virus (A/Puerto Rico/8/34(H1N1))]
MGQEQDTPWILSTGHISTQKRQDGQQTPKLEHRNSTRLMGHCQKTMNQVVMPKQIVYWKQWLSLRNPILV

FLKTRVLKRWRLFSKHE

SEQ ID NO: 22
>gi|8486135|ref|NP_040985.1| polymerase 1 PB1 [Influenza
A virus (A/Puerto Rico/8/34(H1N1))]
MDVNPTLLFLKVPAQNAISTTFPYTGDPPYSHGTGTGYTMDTVNRTHQYSEKARWTTNTETGAPQLNPID

GPLPEDNEPSGYAQTDCVLEAMAFLEESHPGIFENSCIETMEVVQQTRVDKLTQGRQTYDWTLNRNQPAA

TALANTIEVFRSNGLTANESGRLIDFLKDVMESMKKEEMGITTHFQRKRRVRDNMTKKMITQRTIGKRKQ

RLNKRSYLIRALTLNTMTKDAERGKLKRRAIATPGMQIRGFVYFVETLARSICEKLEQSGLPVGGNEKKA

KLANVVRKMMTNSQDTELSLTITGDNTKWNENQNPRMFLAMITYMTRNQPEWFRNVLSIAPIMFSNKMAR

LGKGYMFESKSMKLRTQIPAEMLASIDLKYFNDSTRKKIEKIRPLLIEGTASLSPGMMMGMFNMLSTVLG

VSILNLGQKRYTKTTYWWDGLQSSDDFALIVNAPNHEGIQAGVDRFYRTCKLHGINMSKKKSYINRTGTF

EFTSFFYRYGFVANFSMELPSFGVSGSNESADMSIGVTVIKNNMINNDLGPATAQMALQLFIKDYRYTYR

-continued

CHRGDTQIQTRRSFEIKKLWEQTRSKAGLLVSDGGPNLYNIRNLHIPEVCLKWELMDEDYQGRLCNPLNP

FVSHKEIESMNNAVMMPAHGPAKNMEYDAVATTHSWIPKRNRSILNTSQRGVLEDEQMYQRCCNLFEKFF

PSSSYRRPVGISSMVEAMVSRARIDARIDFESGRIKKEEFTEIMKICSTIEELRRQK

SEQ ID NO: 23

>gi|8486130|ref|NP_040982.1| nucleocapsid protein
[Influenza A virus (A/Puerto Rico/8/34(H1N1))]
MASQGTKRSYEQMETDGERQNATEIRASVGKMIGGIGRFYIQMCTELKLSDYEGRLIQNSLTIERMVLSA

FDERRNKYLEEHPSAGKDPKKTGGPIYRRVNGKWMRELILYDKEEIRRIWRQANNGDDATAGLTHMMIWH

SNLNDATYQRTRALVRTGMDPRMCSLMQGSTLPRRSGAAGAAVKGVGTMVMELVRMIKRGINDRNFWRGE

NGRKTRIAYERMCNILKGKFQTAAQKAMMDQVRESRDPGNAEFEDLTFLARSALILRGSVAHKSCLPACV

YGPAVASGYDFEREGYSLVGIDPFRLLQNSQVYSLIRPNENPAHKSQLVWMACHSAAFEDLRVLSFIKGT

KVVPRGKLSTRGVQIASNENMETMESSTLELRSRYWAIRTRSGGNTNQQRASAGQISIQPTFSVQRNLPF

DRTTVMAAFTGNTEGRTSDMRTEIIRMMESARPEDVSFQGRGVFELSDEKAASPIVPSFDMSNEGSYFFG

DNAEEYDN

SEQ ID NO: 24

>gi|73918826|ref|YP_308855.1| polymerase 2 [Influenza A virus
(A/Korea/426/1968(H2N2))]
MERIKELRNLMSQSRTREILTKTTVDHMAIIKKYTSGRQEKNPSLRMKWMMAMKYPITADKRITEMVPER

NEQGQTLWSKMSDAGSDRVMVSPLAVTWWNRNGPMTSTVHYPKIYKTYFEKVERLKHGTFGPVHFRNQVK

IRRRVDINPGHADLSAKEAQDVIMEVVFPNEVGARILTSESQLTITKEKKEELQDCKISPLMVAYMLERE

LVRKTRFLPVAGGTSSVYIEVLHLTQGTCWEQMYTPGGEVRNDDVDQSLIIAARNIVRRAAVSADPLASL

LEMCHSTQIGGTRMVDILRQNPTEEQAVDICKAAMGLRISSSFSFGGFTFKRTSGSSIKREEEVLTGNLQ

TLKIRVHEGYEEFTMVGKRATAILRKATRRLVQLIVSGRDEQSIAEAIIVAMVFSQEDCMIKAVRGDLNF

VNRANQRLNPMHQLLRHFQKDAKVLFQNWGIEHIDNVMGMIGVLPDMTPSTEMSMRGIRVSKMGVDEYSS

TERVVVSIDRFLRVRDQRGNVLLSPEEVSETQGTEKLTITYSSSMMWEINGPESVLVNTYQWIIRNWETV

KIQWSQNPTMLYNKMEFEPFQSLVPKAIRGQYSGFVRTLFQQMRDVLGTFDTTQIIKLLPFAAAPPKQSR

MQFSSLTVNVRGSGMRILVRGNSPVFNYNKTTKRLTILGKDAGTLTEDPDEGTSGVESAVLRGFLILGKE

DRRYGPALSINELSTLAKGEKANVLIGQGDVVLVMKRKRDSSILTDSQTATKRIRMAIN

SEQ ID NO: 25

>gi|73919145|ref|YP_308850.1| hemagglutinin [Influenza A virus
(A/Korea/426/68(H2N2))]
MAIIYLILLFTAVRGDQICIGYHANNSTEKVDTILERNVTVTHAKDILEKTHNGKLCKLNGIPPLELGDC

SIAGWLLGNPECDRLLSVPEWSYIMEKENPRYSLCYPGSFNDYEELKHLLSSVKHFEKVKILPKDRWTQH

TTTGGSWACAVSGKPSFFRNMVWLTRKGSNYPVAKGSYNNTSGEQMLIIWGVHHPNDEAEQRALYQNVGT

YVSVATSTLYKRSIPEIAARPKVNGLGRRMEFSWTLLDMWDTINFESTGNLVAPEYGFKISKRGSSGIMK

TEGTLENCETKCQTPLGAINTTLPFHNVHPLTIGECPKYVKSEKLVLATGLRNVPQIESRGLFGAIAGFI

EGGWQGMVDGWYGYHHSNDQGSGYAADKESTQKAFNGITNKVNSVIEKMNTQFEAVGKEFSNLEKRLENL

NKKMEDGFLDVWTYNAELLVLMENERTLDFHDSNVKNLYDKVRMQLRDNVKELGNGCFEFYHKCDNECMD

SVKNGTYDYPKYEEESKLNRNEIKGVKLSSMGVYQILAIYATVAGSLSLAIMMAGISFWMCSNGSLQCRI

CI

SEQ ID NO: 26

>gi|73912688|ref|YP_308854.1| membrane protein M1 [Influenza
A virus (A/Korea/426/68(H2N2))]
MSLLTEVETYVLSIVPSGPLKAEIAQRLEDVFAGKNTDLEALMEWLKTRPILSPLTKGILGFVFTLTVPS

ERGLQRRRFVQNALNGNGDPNNMDRAVKLYRKLKREITFHGAKEVALSYSAGALASCMGLIYNRMGAVTT

-continued

EVAFAVVCATCEQIADSQHRSHRQMVTTTNPLIRHENRMVLASTTAKAMEQMAGSSEQAAEAMEVASQAR

QMVQAMRAIGTPPSSSAGLKDDLLENLQAYQKRMGVQMQRFK

SEQ ID NO: 27

>gi|73912687|ref|YP_308853.1| membrane protein M2
[Influenza A virus (A/Korea/426/68(H2N2))]
MSLLTEVETPIRNEWGCRCNDSSDPLVVAASIIGILHFILWILDRLFFKCIYRFFKHGLKRGPSTEGVPE

SMREEYRKEQQSAVDADDSHFVSIELE

SEQ ID NO: 28

>gi|73912685|ref|YP_308852.1| polymerase PA [Influenza A virus
(A/Korea/426/68(H2N2))]
MEDFVRQCFNPMIVELAEKAMKEYGEDLKIETNKFAAICTHLEVCFMYSDFHFINEQGESIMVELDDPNA

LLKHRFEIIEGRDRTMAWTVVNSICNTTGAEKPKFLPDLYDYKENRFIEIGVTRREVHIYYLEKANKIKS

ENTHIHIFSFTGEEMATKADYTLDEESRARIKTRLFTIRQEMANRGLWDSFRQSERGEETIEERFEITGT

MRRLADQSLPPNFSCLENFRAYVDGFEPNGYIEGKLSQMSKEVNAKIEPFLKTTPRPIRLPDGPPCFQRS

KFLLMDALKLSIEDPSHEGEGIPLYDAIKCMRTFFGWKEPYIVKPHEKGINPNYLLSWKQVLAELQDIEN

EEKIPRTKNMKKTSQLKWALGENMAPEKVDFDNCRDISDLKQYDSDEPELRSLSSWIQNEFNKACELTDS

IWIELDEIGEDVAPIEHIASMRRNYFTAEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQMSRP

MFLYVRTNGTSKIKMKWGMEMRPCLLQSLQQIESMVEAESSVKEKDMTKEFFENKSETWPIGESPKGVEE

GSIGKVCRTLLAKSVFNSLYASPQLEGFSAESRKLLLVVQALRDNLEPGTFDLGGLYEAIEECLINDPWV

LLNASWFNSFLTHALR

SEQ ID NO: 29

>gi|73921833|ref|YP_308877.1| PB1-F2 protein [Influenza A virus
(A/Korea/426/68(H2N2))]
MGQEQDTPWTQSTEHINIQKRGSGQQTRKLERPNLTQLMDHYLRTMNQVDMHKQTASWKQWLSLRNHTQE

SLKIRVLKRWKLFNKQEWTN

SEQ ID NO: 30

>gi|73912683|ref|YP_308851.1| PB1 polymerase subunit
[Influenza A virus (A/Korea/426/68(H2N2))]
MDVNPTLLFLKVPAQNAISTTFPYTGDPPYSHGTGTGYTMDTVNRTHQYSEKGKWTTNTETGAPQLNPID

GPLPEDNEPSGYAQTDCVLEAMAFLEESHPGIFENSCLETMEVIQQTRVDKLTQGRQTYDWTLNRNQPAA

TALANTIEVFRSNGLTANESGRLIDFLKDVIESMDKEEMEITTHFQRKRRVRDNMTKKMVTQRTIGKKKQ

RLNKRSYLIRALTLNTMTKDAERGKLKRRAIATPGMQIRGFVHFVETLARNICEKLEQSGLPVGGNEKKA

KLANVVRKMMTNSQDTELSFTITGDNTKWNENQNPRVFLAMITYITRNQPEWFRNVLSIAPIMFSNKMAR

LGKGYMFESKSMKLRTQIPAEMLASIDLKYFNESTRKKIEKIRPLLIDGTVSLSPGMMMGMFNMLSTVLG

VSILNLGQKKYTKTTYWWDGLQSSDDFALIVNAPNHEGIQAGVNRFYRTCKLVGINMSKKKSYINRTGTF

EFTSFFYRYGFVANFSMELPSFGVSGINESADMSIGVTVIKNNMINNDLGPATAQMALQLFIKDYRYTYR

CHRGDTQIQTRRSFELKKLWEQTRSKAGLLVSDGGSNLYNIRNLHIPEVCLKWELMDEDYQGRLCNPLNP

FVSHKEIESVNNAVVMPAHGPAKSMEYDAVATTHSWTPKRNRSILNTSQRGILEDEQMYQKCCNLFEKFF

PSSSYRRPVGISSMVEAMVSRARIDARIDFESGRIKKEEFAEIMKICSTIEELRRQK

SEQ ID NO: 31

>gi|73921567|ref|YP_308869.1| non-structural protein NS2
[Influenza A virus (A/Korea/426/68(H2N2))]
MDSNTVSSFQDILLRMSKMQLGSSSEDLNGMITQFESLKLYRDSLGEAVMRMGDLHSLQNRNGKWREQLG

QKFEEIRWLIEEVRHRLKITENSFEQITFMQALQLLFEVEQEIRTFSFQLI

SEQ ID NO: 32

>gi|73921566|ref|YP_308870.1| non-structural protein NS1
[Influenza A virus (A/Korea/426/68(H2N2))]
MDSNTVSSFQVDCFLWHVRKQVVDQELGDAPFLDRLRRDQKSLRGRGSTLDLDIEAATRVGKQIVERILK

EESDEALKMTMASAPASRYLTDMTIEELSRDWFMLMPKQKVEGPLCIRIDQAIMDKNIMLKANFSVIFDR

-continued

LETLILLRAFTEEGAIVGEISPLPSLPGHTIEDVKNAIGVLIGGLEWNDNTVRVSKTLQRFAWRSSNENG

RPPLTPKQKRKMARTIRSKVRRDKMAD

SEQ ID NO: 33

>gi|73921307|ref|YP_308871.1| nucleoprotein [Influenza A virus (A/Korea/426/68(H2N2))]
MASQGTKRSYEQMETDGERQNATEIRASVGKMIDGIGRFYIQMCTELKLSDYEGRLIQNSLTIERMVLSA

FDERRNKYLEEHPSAGKDPKKTGGPIYKRVDGKWMRELVLYDKEEIRRIWRQANNGDDATAGLTHMMIWH

SNLNDTTYQRTRALVRTGMDPRMCSLMQGSTLPRRSGAAGAAVKGVGTMVMELIRMIKRGINDRNFWRGE

NGRKTRSAYERMCNILKGKFQTAAQRAMMDQVRESRNPGNAEIEDLIFLARSALILRGSVAHKSCLPACV

YGPAIASGYNFEKEGYSLVGIDPFKLLQNSQVYSLIRPNENPAHKSQLVWMACNSAAFEDLRVLSFIRGT

KVSPRGKLSTRGVQIASNENMDTMESSTLELRSRYWAIRTRSGGNTNQQRASAGQISVQPAFSVQRNLPF

DKPTIMAAFTGNTEGRTSDMRAEIIRMMEGAKPEEMSFQGRGVFELSDEKATNPIVPSFDMSNEGSYFFG

DNAEEYDN

SEQ ID NO: 34

>gi|73921304|ref|YP_308872.1| neuraminidase [Influenza A virus (A/Korea/426/68(H2N2))]
MNPNQKIITIGSVSLTIATVCFLMQIAILVTTVTLHFKQHECDSPASNQVMPCEPIIIERNITEIVYLNN

TTIEKEICPEVVEYRNWSKPQCQITGFAPFSKDNSIRLSAGGDIWVTREPYVSCDPGKCYQFALGQGTTL

DNKHSNDTIHDRIPHRTLLMNELGVPFHLGTRQVCVAWSSSSCHDGKAWLHVCVTGDDKNATASFIYDGR

LMDSIGSWSQNILRTQESECVCINGTCTVVMTDGSASGRADTRILFIEEGKIVHISPLSGSAQHVEECSC

YPRYPDVRCICRDNWKGSNRPVIDINMEDYSIDSSYVCSGLVGDTPRNDDRSSNSNCRNPNNERGNPGVK

GWAFDNGDDVWMGRTISKDLRSGYETFKVIGGWSTPNSKSQINRQVIVDSNNWSGYSGIFSVEGKRCINR

CFYVELIRGRQQETRVWWTSNSIVVFCGTSGTYGTGSWPDGANINFMPI

SEQ ID NO: 35

>gi|73919213|ref|YP_308844.1| nonstructural protein 2 [Influenza A virus (A/New York/392/2004(H3N2))]
MDSNTVSSFQDILLRMSKMQLGSSSEDLNGMITQFESLKIYRDSLGEAVMRMGDLHLLQNRNGKWREQLG

QKFEEIRWLIEEVRHRLKTTENSFEQITFMQALQLLFEVEQEIRTFSFQLI

SEQ ID NO: 36

>gi|73919212|ref|YP_308845.1| nonstructural protein 1 [Influenza A virus (A/New York/392/2004(H3N2))]
MDSNTVSSFQVDCFLWHIRKQVVDQELSDAPFLDRLRRDQRSLRGRGNTLGLDIKAATHVGKQIVEKILK

EESDEALKMTMVSTPASRYITDMTIEELSRNWFMLMPKQKVEGPLCIRMDQAIMEKNIMLKANFSVIFDR

LETIVLLRAFTEEGAIVGEISPLPSFPGHTIEDVKNAIGVLIGGLEWNDNTVRVSKNLQRFAWRSSNENG

GPPLTPKQKRKMARTARSKV

SEQ ID NO: 37

>gi|73919207|ref|YP_308839.1| hemagglutinin [Influenza A virus (A/New York/392/2004(H3N2))]
MKTIIALSYILCLVFAQKLPGNDNSTATLCLGHHAVPNGTIVKTITNDQIEVTNATELVQSSSTGGICDS

PHQILDGENCTLIDALLGDPQCDGFQNKKWDLFVERSKAYSNCYPYDVPDYASLRSLVASSGTLEFNNES

FNWTGVTQNGTSSACKRRSNNSFFSRLNWLTHLKFKYPALNVTMPNNEKFDKLYIWGVHHPGTDNDQISL

YAQASGRITVSTKRSQQTVIPSIGSRPRIRDVPSRISIYWTIVKPGDILLINSTGNLIAPRGYFKIRSGK

SSIMRSDAPIGKCNSECITPNGSIPNDKPFQNVNRITYGACPRYVKQNTLKLATGMRNVPEKQTRGIFGA

IAGFIENGWEGMVDGWYGFRHQNSEGTGQAADLKSTQAAINQINGKLNRLIGKTNEKFHQIEKEFSEVEG

RIQDLEKYVEDTKIDLWSYNAELLVALENQHTIDLTDSEMNKLFERTKKQLRENAEDMGNGCFKIYHKCD

NACIGSIRNGTYDHDVYRDEALNNRFQIKGVELKSGYKDWILWISFAISCFLLCVALLGFIMWACQKGNI

RCNICI

-continued

SEQ ID NO: 38
>gi|73919153|ref|YP_308840.1| matrix protein 2 [Influenza A virus (A/New York/392/2004(H3N2))]
MSLLTEVETPIRNEWGCRCNDSSDPLVVAASIIGILHLILWILDRLFFKCVYRLFKHGLKRGPSTEGVPE

SMREEYRKEQQNAVDADDSHFVSIELE

SEQ ID NO: 39
>gi|73919152|ref|YP_308841.1| matrix protein 1 [Influenza A virus (A/New York/392/2004(H3N2))]
MSLLTEVETYVLSIVPSGPLKAEIAQRLEDVFAGKNTDLEALMEWLKTRPILSPLTKGILGFVFTLTVPS

ERGLQRRRFVQNALNGNGDPNNMDKAVKLYRKLKREITFHGAKEIALSYSAGALASCMGLIYNRMGAVTT

EVAFGLVCATCEQIADSQHRSHRQMVATTNPLIKHENRMVLASTTAKAMEQMAGSSEQAAEAMEIASQAR

QMVQAMRAVGTHPSSSTGLRDDLLENLQTYQKRMGVQMQRFK

SEQ ID NO: 40
>gi|73919150|ref|YP_308848.1| PB1-F2 protein [Influenza A virus (A/New York/392/2004(H3N2))]
MEQEQDTPWTQSTEHTNIQRRGSGRQIQKLGHPNSTQLMDHYLRIMSQVDMHKQTVSWRLWPSLKNPTQV

SLRTHALKQWKSFNKQGWTN

SEQ ID NO: 41
>gi|73919149|ref|YP_308847.1| polymerase PB1 [Influenza A virus (A/New York/392/2004(H3N2))]
MDVNPTLLFLKVPAQNAISTTFPYTGDPPYSHGTGTGYTMDTVNRTHQYSEKGKWTTNTETGAPQLNPID

GPLPEDNEPSGYAQTDCVLEAMAFLEESHPGIFENSCLETMEVVQQTRVDKLTQGRQTYDWTLNRNQPAA

TALANTIEVFRSNGLTANESGRLIDFLKDVMESMDKEEMEITTHFQRKRRVRDNMTKKMVTQRTIGKKKQ

RVNKRGYLIRALTLNTMTKDAERGKLKRRAIATPGMQIRGFVYFVETLARSICEKLEQSGLPVGGNEKKA

KLANVVRKMMTNSQDTELSFTITGDNTKWNENQNPRMFLAMITYITKNQPEWFRNILSIAPIMFSNKMAR

LGKGYMFESKRMKLRTQIPAEMLASIDLKYFNESTRKKIEKIRPLLIDGTASLSPGMMMGMFNMLSTVLG

VSVLNLGQKKYTKTTYWWDGLQSSDDFALIVNAPNHEGIQAGVDRFYRTCKLVGINMSKKKSYINKTGTF

EFTSFFYRYGFVANFSMELPSFGVSGINESADMSIGVTVIKNNMINNDLGPATAQMALQLFIKDYRYTYR

CHRGDTQIQTRRSFELKKLWDQTQSRAGLLVSDGGPNLYNIRNLHIPEVCLKWELMDENYRGRLCNPLNP

FVSHKEIESVNNAVVMPAHGPAKSMEYDAVATTHSWNPKRNRSILNTSQRGILEDEQMYQKCCNLFEKFF

PSSSYRRPIGISSMVEAMVSRARIDARIDFESGRIKKEEFSEIMKICSTIEELRRQK

SEQ ID NO: 42
>gi|73919147|ref|YP_308843.1| nucleocapsid protein [Influenza A virus (A/New York/392/2004(H3N2))]
MASQGTKRSYEQMETDGDRQNATEIRASVGKMIDGIGRFYIQMCTELKLSDHEGRLIQNSLTIEKMVLSA

FDERRNKYLEEHPSAGKDPKKTGGPIYRRVDGKWMRELVLYDKEEIRRIWRQANNGEDATAGLTHIMIWH

SNLNDATYQRTRALVRTGMDPRMCSLMQGSTLPRRSGAAGAAVKGIGTMVMELIRMVKRGINDRNFWRGE

NGRKTRSAYERMCNILKGKFQTAAQRAMVDQVRESRNPGNAEIEDLIFLARSALILRGSVAHKSCLPACA

YGPAVSSGYDFEKEGYSLVGIDPFKLLQNSQIYSLIRPNENPAHKSQLVWMACHSAAFEDLRLLSFIRGT

KVSPRGKLSTRGVQIASNENMDNMGSSTLELRSGYWAIRTRSGGNTNQQRASAGQTSVQPTFSVQRNLPF

EKSTIMAAFTGNTEGRTSDMRAEIIRMMEGAKPEEVSFRGRGVFELSDEKATNPIVPSFDMSNEGSYFFG

DNAEEYDN

SEQ ID NO: 43
>gi|73919136|ref|YP_308842.1| neuraminidase [Influenza A virus (A/New York/392/2004(H3N2))]
MNPNQKIITIGSVSLTISTICFFMQIAILITTVTLHFKQYEFNSPPNNQVMLCEPTIIERNITEIVYLTN

TTIEKEMCPKLAEYRNWSKPQCDITGFAPFSKDNSIRLSAGGDIWVTREPYVSCDPDKCYQFALGQGTTL

NNVHSNDTVHDRTPYRTLLMNELGVPFHLGTKQVCIAWSSSSCHDGKAWLHVCVTGDDKNATASFIYNGR

LVDSIVSWSKKILRTQESECVCINGTCTVVMTDGSASGKADTKILFIEEGKIIHTSTLSGSAQHVEECSC

YPRYPGVRCVCRDNWKGSNRPIVDINIKDYSIVSSYVCSGLVGDTPRKNDSSSSSHCLDPNNEEGGHGVK

-continued

GWAFDDGNDVWMGRTISEKLRSGYETFKVIEGWSKPNSKLQINRQVIVDRGNRSGYSGIFSVEGKSCINR

CFYVELIRGRKEETEVLWTSNSIVVFCGTSGTYGTGSWPDGADINLMPI

SEQ ID NO: 44

>gi|73919134|ref|YP_308846.1| polymerase PA [Influenza A virus (A/New York/392/2004(H3N2))]
MEDFVRQCFNPMIVELAEKAMKEYGEDLKIETNKFAAICTHLEVCFMYSDFHFINEQGESIVVELDDPNA

LLKHRFEIIEGRDRTMAWTVVNSICNTTGAEKPKFLPDLYDYKENRFIEIGVTRREVHIYYLEKANKIKS

ENTHIHIFSFTGEEIATKADYTLDEESRARIKTRLFTIRQEMANRGLWDSFRQSERGEETIEEKFEISGT

MRRLADQSLPPKFSCLENFRAYVDGFEPNGCIEGKLSQMSKEVNAKIEPFLKTTPRPIKLPNGPPCYQRS

KFLLMDALKLSIEDPSHEGEGIPLYDAIKCIKTFFGWKEPYIVKPHEKGINSNYLLSWKQVLSELQDIEN

EEKIPRTKNMKKTSQLKWALGENMAPEKVDFDNCRDISDLKQYDSDEPELRSLSSWIQNEFNKACELTDS

IWIELDEIGEDVAPIEYIASMRRNYFTAEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQISRP

MFLYVRTNGTSKVKMKWGMEMRRCLLQSLQQIESMIEAESSIKEKDMTKEFFENKSEAWPIGESPKGVEE

GSIGKVCRTLLAKSVFNSLYASPQLEGFSAESRKLLLVVQALRDNLEPGTFDLGGLYEAIEECLINDPWV

LLNASWFNSFLTHALK

SEQ ID NO: 45

>gi|73919060|ref|YP_308849.1| polymerase PB2 [Influenza A virus (A/New York/392/2004(H3N2))]
MERIKELRNLMSQSRTREILTKTTVDHMAIIKKYTSGRQEKNPSLRMKWMMAMKYPITADKRITEMVPER

NEQGQTLWSKMSDAGSDRVMVSPLAVTWWNRNGPVASTVHYPKVYKTYFDKVERLKHGTFGPVHFRNQVK

IRRRVDINPGHADLSAKEAQDVIMEVVFPNEVGARILTSESQLTITKEKKEELRDCKISPLMVAYMLERE

LVRKTRFLPVAGGTSSIYIEVLHLTQGTCWEQMYTPGGEVRNDDVDQSLIIAARNIVRRAAVSADPLASL

LEMCHSTQIGGTRMVDILRQNPTEEQAVDICKAAMGLRISSSFSFGGFTFKRTSGSSVKKEEEVLTGNLQ

TLKIRVHEGYEEFTMVGKRATAILRKATRRLVQLIVSGRDEQSIAEAIIVAMVFSQEDCMIKAVRGDLNF

VNRANQRLNPMHQLLRHFQKDAKVLFQNWGIEHIDSVMGMVGVLPDMTPSTEMSMRGIRVSKMGVDEYSS

TERVVVSIDRFLRVRDQRGNVLLSPEEVSETQGTERLTITYSSSMMWEINGPESVLVNTYQWIIRNWEAV

KIQWSQNPAMLYNKMEFEPFQSLVPKAIRSQYSGFVRTLFQQMRDVLGTFDTTQIIKLLPFAAAPPKQSR

MQFSSLTVNVRGSGMRILVRGNSPVFNYNKTTKRLTILGKDAGTLIEDPDESTSGVESAVLRGFLIIGKE

DRRYGPALSINELSNLAKGEKANVLIGQGDVVLVMKRKRDSSILTDSQTATKRIRMAIN

SEQ ID NO: 46: CMV Protein 1E122:
>gi|39841910|gb|AAR31478.1| UL122 [Human herpesvirus 5]
MESSAKRKMDPDNPDEGPSSKVPRPETPVTKATTFLQTMLRKEVNSQLSLGDPLFPELAEESLKTFEQVT

EDCNENPEKDVLAELGDILAQAVNHAGIDSSSTGHTLTTHSCSVSSAPLNKPTPTSVAVTNTPLPGASAT

PELSPRKKPRKTTRPFKVIIKPPVPPAPIMLPLIKQEDIKPEPDFTIQYRNKIIDTAGCIVISDSEEEQG

EEVETRGATASSPSTGSGTPRVTSPTHPLSQMNHPPLPDPLARPDEDSSSSSSSSCSSASDSESESEEMK

CSSGGGASVTSSHHGRGGFGSAASSSLLSCGHQSSGGASTGPRKKKSKRISELDNEKVRNIMKDKNTPFCTPNVQTRRG

RVKIDEVSRMFRNTNRSLEYKNLPFTIPSMHQVLDRAIKACKTMQVNNKGIQIIYTRNHEVKSEVDAVRCRLGTMCNLA

LSTPFLMEHTMPVTHPPEVAQRTADACNEGVKAAWSLKELHTHQLCPRSSDYRNMIIHAATPVDLLGALNLCLPLMQKF

PKQVMVRIFSTNQGGFMLPIYETAAKAYAVGQFEQPTETPPEDLDTLSLAIEAAIQDLRNKSQ

SEQ ID NO: 126:
>gi|4927721|gb|AAD33253.1|AF125673_2 E7 [Human papillomavirus type 16]
MHGDTPTLHEYMLDLQPETTDLYCYEQLNDSSEEEDEIDGPAGQAEPDRAHYNIVTFCCKCDSTLRLCVQ

STHVDIRTLEDLLMGTLGIVCPICSQKP

EXAMPLE 1

The peptides according to the invention used in the following examples were synthesized by Schafer-N as c-terminal amides using the Fmoc-strategy of Sheppard, (1978) J. Chem. Soc., Chem. Commun., 539.

Cell Penetration Assay

A set of peptides were biotinylated on N-terminal, and different combinations of aminoacids, with respect to length and type, were added to the sequence box $X^1$, $X^3$ and $X^4$ in the peptides as illustrated by the diagram below. The peptides were tested on cells grown from one individual blood donor.

Schematic diagram of amino acid sequence of the peptides according to the invention (Each X defines a sequence of amino acids):

| $X^1$ | $X^2$ | $X^3$ | $X^4$ | $X^5$ |
|---|---|---|---|---|

SP 2 to SP 17 are variants of 51n_Biotin, from a specific native domain on the HCV core protein.

Intracellular Staining for Biotinylated Peptides 96-well U-bottom polystyrene plates (NUNC, cat no: 163320) were used for staining of human PBMCs. Briefly, 8 ul of N- or C-terminally biotinylated peptides according to table 1 or table 2 (i.e. 5 mM, 2.5 mM & 1.25 mM tested for each peptide) were incubated at 37° C. for 2 h with 40 ul of PBMC (12.5×106 cells/ml) from blood donors. Cells were then washed 3× with 150 ul of Cellwash (BD, cat no: 349524), followed by resuspension of each cell pellet with 100 ul of Trypsin-EDTA (Sigma, cat no: T4424), then incubated at 37° C. for 5 min. Trypsinated cells were then washed 3× with 150 ul of Cellwash (BD, cat no: 349524), followed by resuspension with BD Cytofix/Cytoperm™ plus (BD, cat no: 554715), then incubated at 4° C. for 20 min according to manufacturer. Cells were then washed 2× with 150 ul PermWash (BD, cat no: 554715). Cells were then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3× with 150 ul PermWash, followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

Extracellular Staining for Biotinylated Peptides 96-well U-bottom polystyrene plates (NUNC, cat no: 163320) were used for staining of human PBMCs. Briefly, 8 ul of N- or C-terminally biotinylated peptides according to table 1 or table 2 (i.e. 5 mM, 2.5 mM & 1.25 mM tested for each peptide; all peptides manufactured by Schafer) were incubated at 37° C. for 2 h with 40 ul of PBMC (12.5×106 cells/ml) from blood donors. Cells were then washed 3× with 150 ul of Cellwash (BD, cat no: 349524), then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3× with 150 ul of Cellwash (BD, cat no: 349524), followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

It was clearly seen that the arginine added on the beginning, middle and in the end improves the ability to enter the cell. It was observed that the variations of arginine decides the ability to enter the cell, best result are achieved with two in the beginning and two in the middle—but variations of different amount of arginines all show good result.

The data shown in the tables below are geomean-value of each testet peptide, as calculated by the FACS Duva software. The Geomean values by trypsinating/Cytofix/Cytoperm:

TABLE 3

With Cytofix/Cytoperm and trypsination

| | BC20 Concentration | | | |
|---|---|---|---|---|
| | 833 μM | 417 μM | 208 μM | 104 μM |
| 51n_Biotin | ND | ND | ND | ND |
| SP 2 | 3136 | 5486 | | 1211 |
| SP 3 | 40456 | 25905 | 10788 | 4308 |
| Sp 4 | 41491 | 28008 | 7540 | 2946 |
| Sp 5 | 40534 | 46060 | 19065 | 6152 |
| Sp 6 | 32577 | 22195 | 6514 | 1850 |
| Sp 7 | 47922 | 30503 | 10481 | 2766 |
| SP 8 | 31976 | 28606 | 9617 | 2917 |
| SP 9 | 11344 | 6060 | 2945 | 1268 |
| SP 10 | 43389 | 18607 | 7684 | 3709 |
| SP 11 | 8262 | 3562 | 1277 | 601 |
| SP 12 | 11089 | 10869 | 8679 | 4316 |
| SP 13 | 568 | 394 | 332 | |
| SP 14 | 1059 | 682 | 392 | 62 |
| SP 15 | 1810 | 477 | 848 | 600 |
| SP 16 | 4558 | 2240 | 1260 | 505 |
| SP 17 | 30248 | 29967 | 12244 | 1500 |
| SP 18 | 4869 | 1334 | 1971 | 1038 |
| SP 19 | 17018 | 7201 | 3466 | 1625 |
| SP 20 | 7319 | 2457 | 1268 | 445 |
| −ve | 0 | 0 | 0 | 0 |
| +ve | 18694 | 26046 | 15340 | 7182 |
| No peptide | 224 | 106 | 78 | 168 |

As shown in table 4 the peptides according to the invention had the ability to allocate through the cell membrane.

TABLE 4

Results on DC-cells with low concentration of peptides (208 uM). The results are sorted in descending order (with respect to BC 16).

| Peptide | BC 16 | BC43 |
|---|---|---|
| no pept | 4473 | 2488 |
| NO pept | 4003 | 2359 |
| NO pept | 7799 | |
| P-biotin | 22058 | 33545 |
| P-biotin | 5568 | 26212 |
| P-biotin | 28169 | |
| n-biotin | 3745 | 1967 |
| N-biotin | 3591 | 3631 |
| N-biotin | 2271 | |
| SP61_2 | 128330 | 150491 |
| 42 | 74920 | 65811 |
| SP42_1 | 73973 | |
| SP17 | 67428 | |
| SP51_1* | 66582 | |
| BI10026 | 65196 | 43536 |
| SP11b_1 | 64047 | |

TABLE 4-continued

Results on DC-cells with low concentration of peptides (208 uM). The results are sorted in descending order (with respect to BC 16).

| Peptide | BC 16 | BC43 |
|---|---|---|
| 42b | 61968 | 19181 |
| SP22 | 61597 | 18624 |
| 51 biotin | 59789 | 33935 |
| SP12 | 59274 | 31222 |
| BI100260 | 47846 | |
| SP61__3 | 47182 | 36803 |
| V10 | 45430 | |
| 120b | 44185 | |
| 100-22b | 43537 | 28780 |
| BI100260b | 37702 | |
| SP12__c | 37100 | 43386 |
| 18b | 29740 | 33597 |
| SP13 | 28539 | 9129 |
| BI10024b | 26892 | 13002 |
| SP21 | 26525 | 4294 |
| 61b biotin | 25611 | 24416 |
| SPS1b__2 | 25489 | |
| 310-11-n-sc | 25236 | |
| 100-12 | 24792 | 45622 |
| SP5 | 21358 | 29146 |
| SP4__c | 20673 | 30786 |
| SP7__c | 20041 | 11832 |
| SP20 | 19051 | 3383 |
| 190n | 18616 | 23383 |
| SP3__c | 18505 | 26308 |
| SP24 | 18181 | 63639 |
| SP6__c | 17964 | 38487 |
| SP42b__1 | 17628 | |
| SP23 | 17084 | 12801 |
| SP5__c | 16908 | 24403 |
| SP7 | 16064 | 21414 |
| SP8 | 15379 | 17836 |
| BI-050sc5 | 13648 | 15549 |
| 190 | 12906 | |
| SP61__4 | 12829 | |
| 190b | 12391 | 20444 |
| SP17__c | 11830 | |
| SP25 | 11552 | |
| SP4 | 10751 | 17372 |
| SP6 | 10233 | 14468 |
| SP3 | 9480 | 10573 |
| SP1__C | 9234 | |
| SP8__c | 9159 | 23763 |
| SP10 | 8627 | 9216 |
| 19 | 8417 | 6372 |
| SP9 | 8356 | 10084 |
| N13 | 7982 | 5953 |
| 51b | 7000 | 6082 |
| SP10__c | 6904 | |
| SP2 | 6677 | 6112 |
| 310-11 | 6537 | |
| SP19 | 6522 | 6536 |
| SP11 | 6490 | 13230 |
| SP9__c | 6180 | 7758 |
| BI-050sc1 | 6056 | 6160 |
| BI-050sc2 | 6019 | 11584 |
| SP16 | 5730 | 3656 |
| 51n | 5551 | 7721 |
| SP18 | 5545 | 7751 |
| 310-11n | 5436 | |
| SP11__c | 5371 | 7878 |
| SP15 | 5076 | 2539 |
| N10 | 4597 | |
| SP14 | 3704 | 1629 |
| SP2__c | 323 | 13341 |
| SP13__c | | 60307 |
| 42n | | |

EXAMPLE 2

Positive CTL response may alternatively be assayed by ELISPOT assay.

Human IFN-Gamma Cytotoxic T-Cell (CTL) Response by ELISPOT Assay

Briefly, at day 1, PBMC samples from HCV patients were incubated in flasks (430 000 PBMCs/cm2) for 2 h at 37° C., 5% CO2 in covering amount of culture media (RPMI 1640 Fisher Scientific; Cat No. PAAE15-039 supplemented with L-Glutamine, (MedProbe Cat. No. 13E17-605E, 10% Foetal Bovine serum (FBS), Fisher Scientific Cat. No. A15-101) and Penicillin/Streptomycin, (Fisher Acientific Cat. No. P11-010) in order to allow adherence of monocytes. Non-adherent cells were isolated, washed, and frozen in 10% V/V DMSO in FBS until further usage. Adherent cells were carefully washed with culture media, followed by incubation at 37° C. until day 3 in culture media containing 2 μg/ml final concentration of hrGM-CSF (Xiamen amoytop biotech co, cat no: 3004.9090.90) & 1 μg/ml hrIL-4 (Invitrogen, Cat no: PHC0043), and this procedure was then repeated at day 6. At day 7, cultured dendritic cells (5 000-10 000 per well) were added to ELISPOT (Millipore multiscreen HTS) plates coated with 0.5 μg/well anti-human γ Interferon together with thawed autologous non-adherent cells (200 000 per well), antigen samples (1-8 ug/ml final concentration for peptide antigens; 5 ug/ml final concentration for Concanavalin A (Sigma, Cat no: C7275) or PHA (Sigma, Cat no: L2769)) & anti-Anergy antibodies (0.03-0.05 ug/ml final concentration for both anti-PD-1 (eBioscience, cat no: 16-9989-82) & anti-PD-L1 (eBioscience, cat no: 16-5983-82)). Plates were incubated overnight and spots were developed according to manufacturer. Spots were read on ELISPOT reader (CTL-ImmunoSpot® S5 UV Analyzer).

TABLE 5

ELISPOT of core proteins

| | | Patient A | | Patient B | | Patient C | | Patient D | |
|---|---|---|---|---|---|---|---|---|---|
| | ConA | 5090 | 5035 | 2605 | 2725 | 1355 | 700 | 529 | 512 |
| | No Pep | 20 | 25 | 10 | 25 | 10 | 0 | 4 | 1 |
| | Irr.peptide | 10 | 30 | 40 | 5 | 45 | 0 | 1 | 2 |
| **RR**SRNLGKVIDTLTC**BR**LMGYIPLVGA | 310-42b | 90 | 115 | 60 | 80 | 70 | 25 | 13 | 11 |
| **RR**IRNLGRVIETLT**GBR**LZGYIPLIGA | 310-42 | 75 | 80 | 95 | 30 | 25 | 55 | 13 | 11 |
| **RR**GYIPLVGAPL**GBR**VARALAHGVRV | 310-51b | 45 | 40 | 50 | 85 | 45 | 75 | 9 | 13 |
| **RR**GYLPAVGAPI**GBR**VIRVIAHGLRL | 310-51 | 40 | 75 | 50 | 60 | 100 | 35 | 9 | 9 |

TABLE 5-continued

| ELISPOT of core proteins | | | | | | | | | |
|---|---|---|---|---|---|---|---|---|---|
| | | Patient A | | Patient B | | Patient C | | Patient D | |
| | ConA | 5090 | 5035 | 2605 | 2725 | 1355 | 700 | 529 | 512 |
| | No Pep | 20 | 25 | 10 | 25 | 10 | 0 | 4 | 1 |
| | Irr.peptide | 10 | 30 | 40 | 5 | 45 | 0 | 1 | 2 |
| **RR**NYATGNLPG**RR**GCSFSIFLLAL | 310-61b | 45 | 35 | 25 | 45 | 55 | 40 | 15 | 17 |
| **RR**GGGQIIGGNYLIP**RB**GPBIGVRATB | 310-11 | ND | ND | ND | ND | ND | ND | 11 | 14 |

Table 5 - Results from IFN-g ELISPOT run on scaffold peptides with domains derived from HCV proteins The peptides had in general a higher amount of T-cell spots compared to No Peptide and the irrelevant control peptide. This clearly indicates that the peptides have a positive immunological effect in HCV-patients.

EXAMPLE 3

The REVEAL & ProVE® Rapid Epitope Discovery System in Detail

Binding properties to HLA for the ninemers listed in table 6 were tested for the following HLA-classes:

HLA-A1, HLA-A2, HLA-A3, HLA-A11, HLA-A24, HLA-A29, HLA-B7, HLA-B8, HLA-B14, HLA-B15, HLA-B27, HLA-B35, HLA-B40.

The peptides were synthesized as a Prospector PEPscreen®: Custom Peptide Library. Peptides 8-15 amino acids in length were synthesized in 0.5-2 mg quantities with high average purity. Quality control by MALDI-TOF Mass Spectrometry was carried out on 100% of samples.

The REVEAL™ binding assay determined the ability of each candidate peptide to bind to one or more MHC class I alleles and stabilizing the MHC-peptide complex. By comparing the binding to that of high and intermediate affinity T cell epitopes, the most likely immunogenic peptides in a protein sequence can be identified. Detection is based on the presence or absence of the native conformation of the MHC-peptide complex. Each peptide is given a score relative to the positive control peptide, which is a known T cell epitope. The score of the test peptide is reported quantitatively as a percentage of the signal generated by the positive control peptide, and the peptide is indicated as having a putative pass or fail result. Assay performance is confirmed by including an intermediate control peptide that is known to bind with weaker affinity to the allele under investigation.

TABLE 6

| | HLA-type | A1 | A2 | A3 | A11 | A24 | A29 | B7 | B8 | B14 | B15 | B27 | B35 | B40 |
|---|---|---|---|---|---|---|---|---|---|---|---|---|---|---|
| | Positive Control | 100.00 | 100.00 | 100.00 | 100.00 | 100.00 | 100.00 | 100.00 | 100.00 | 100.00 | 100.00 | 100.00 | 100.00 | 100.00 |
| | Inter-mediate Control | 8.41 | 8.79 | 10 | 14.95 | 10 | 30.52 | 12.00 | 56.60 | 24.21 | 56.88 | 10.49 | 93.56 | 76.48 |
| AA placement in HCV-core protein | Linear Sequence | | | | | | | | | | | | | |
| 163-171 | NYATGNLPG | **11.16** | 3.94 | 8.65 | 4.69 | 1.13 | **34.26** | 0.51 | 9.96 | 0.79 | 6.06 | 2.33 | 6.44 | 75.28 |
| 163-171 (mod) | NYVTGNIPG | N/D | N/D | N/D | N/D | N/D | N/D | N/D | N/D | N/D | N/D | N/D | N/D | N/D |
| 164-172 | YATGNLPGC | 8.10 | **22.46** | 3.67 | 2.16 | 1.20 | 18.82 | 0.76 | 9.51 | 0.41 | 5.09 | 2.44 | 4.52 | 77.49 |
| 164-172 (mod) | YVTGNIPGS | **13.33** | 6.88 | 5.34 | 5.18 | 2.71 | 10.29 | 2.70 | 12.40 | 0.76 | 6.16 | 1.98 | 4.42 | 88.29 |
| 165-173 | ATGNLPGCS | 7.13 | 4.62 | 3.64 | 2.54 | 0.64 | 22.84 | 1.12 | 10.73 | 0.87 | 3.81 | 2.56 | 7.00 | 90.48 |
| 165-173 (mod) | VTGNIPGST | **16.18** | 8.44 | 2.52 | 4.85 | 1.60 | 15.05 | 2.24 | 13.12 | 0.75 | 5.15 | 1.58 | 4.00 | 130.97 |
| 166-174 | TGNLPGCSF | **11.97** | 5.18 | 3.71 | 2.56 | 4.81 | 18.89 | 2.38 | 8.62 | 0.86 | 45.07 | 2.37 | 11.40 | 73.71 |
| 266-174 (mod) | TGNIPGSTY | **10.58** | 3.59 | **13.04** | 6.06 | 0.86 | **35.10** | 1.32 | 10.25 | 1.15 | 52.30 | 1.98 | 48.40 | 38.15 |
| 167-175 | GNLPGCSFS | 6.44 | 6.11 | 3.54 | 2.41 | 1.13 | 13.48 | 1.84 | 8.71 | 0.81 | 3.96 | 13.44 | 4.80 | 80.68 |

TABLE 6-continued

| | HLA-type | A1 | A2 | A3 | A11 | A24 | A29 | B7 | B8 | B14 | B15 | B27 | B35 | B40 |
|---|---|---|---|---|---|---|---|---|---|---|---|---|---|---|
| 167-175 (mod) | GNIPGSTYS | 7.54 | 5.07 | 5.04 | 1.54 | 0.00 | 24.38 | 0.94 | 6.32 | 0.34 | 4.80 | 1.58 | 7.86 | 55.59 |
| 168-176 | NLPGCSFSI | **13.15** | **47.28** | 8.15 | 3.47 | **85.91** | 22.34 | 1.54 | 9.89 | 0.36 | 3.11 | 3.37 | 5.31 | 60.68 |
| 168-176 (mod) | NIPGSTYSL | 8.41 | 5.71 | 3.98 | 3.20 | 8.50 | **31.99** | 4.80 | 7.66 | 0.46 | 4.46 | 2.29 | 4.71 | 37.01 |
| 171-179 | GCSFSIFLL | 3.65 | 5.69 | 1.85 | 4.77 | 2.18 | 8.96 | 2.88 | 11.10 | 0.32 | 4.28 | 2.53 | 3.03 | 52.58 |
| 171-179 (mod) | GITFSIYLI | 9.61 | 7.27 | 1.42 | 4.88 | 3.05 | 10.42 | 2.07 | 8.94 | 0.63 | 8.15 | 3.29 | 9.27 | 68.30 |
| 172-180 | CSFSIFLLA | 9.69 | 23.38 | 5.68 | 9.00 | 1.37 | 6.45 | 2.22 | 9.85 | 0.93 | 11.66 | 2.99 | 4.96 | 33.53 |
| 172-180 (mod) | ITFSIYLIV | 9.89 | 43.08 | 1.66 | 5.31 | 0.77 | 24.10 | 4.32 | 11.38 | 1.53 | 6.68 | 4.79 | 12.30 | 78.84 |
| 173-181 | SFSIELLAL | 5.68 | 2.70 | 1.42 | 2.21 | 3.28 | 30.35 | 1.44 | 7.98 | 0.60 | 8.89 | 3.06 | 5.33 | 21.04 |
| 173-181 (mod) | TFSIYLIVS | 9.93 | 2.02 | 0.91 | 2.89 | 0.60 | 8.58 | 1.28 | 9.52 | 0.37 | 8.63 | 1.49 | 2.48 | 23.23 |
| 174-182 | SRNLGKVID | 15.30 | 4.94 | 3.46 | 4.45 | 0.71 | 9.94 | 1.28 | 16.71 | 0.67 | 11.25 | 1.28 | 4.59 | 33.93 |
| 174-182 (mod) | IRNLGRVIE | 14.22 | 8.77 | 3.89 | 5.31 | 0.61 | 11.06 | 1.43 | 9.10 | 30.77 | 4.06 | 1.84 | 1.98 | 21.40 |
| 175-183 | RNLGKVIDT | 18.90 | 6.42 | 3.15 | 6.22 | 1.04 | 10.18 | 2.42 | 13.80 | 0.61 | 11.79 | 2.73 | 4.40 | 48.14 |
| 175-183 (mod) | RNLGRVIET | 15.93 | 5.96 | 5.52 | 13.68 | 0.51 | 15.13 | 0.71 | 15.51 | 0.26 | 8.84 | 0.91 | 2.34 | 27.57 |
| 176-184 | NLGKVIDTL | 18.14 | 7.70 | 6.41 | 12.81 | 1.16 | 10.67 | 2.64 | 16.86 | 0.57 | 12.59 | 2.64 | 4.39 | 53.82 |
| 176-184 (mod) | NLGRVIETL | 18.24 | 11.97 | 2.86 | 4.53 | 0.86 | 16.44 | 1.47 | 15.58 | 0.07 | 16.29 | 1.66 | 2.82 | 38.91 |
| 177-185 | LGKVIDTLT | 22.08 | 4.05 | 7.39 | 12.95 | 0.70 | 15.99 | 0.94 | 17.96 | 0.43 | 7.14 | 2.90 | 5.11 | 44.92 |
| 177-185 (mod) | LGRVIETLT | 16.33 | 5.90 | 7.40 | 20.27 | 0.97 | 12.31 | 2.66 | 14.74 | 0.28 | 16.38 | 2.54 | 3.43 | 62.07 |
| 178-186 | GKVIDTLTC | 14.77 | 4.89 | 3.69 | 3.96 | 0.41 | 14.26 | 0.25 | 13.63 | 0.16 | 7.31 | 0.84 | 3.11 | 19.45 |
| 178-186 (mod) | GRVIETLTS | 14.42 | 5.26 | 12.46 | 27.62 | 0.88 | 15.59 | 1.25 | 12.91 | 0.20 | 8.31 | 1.05 | 3.56 | 38.91 |
| 179-187 | KVIDTLTCG | 15.77 | 19.13 | 4.27 | 8.91 | 0.57 | 13.16 | 0.57 | 13.17 | 0.18 | 10.13 | 0.63 | 2.74 | 32.89 |
| 179-187 (mod) | RVIETLTSG | 11.61 | 9.82 | 2.23 | 3.25 | 0.96 | 15.52 | 0.50 | 11.83 | 0.11 | 37.99 | 2.32 | 1.90 | 32.30 |
| 180-188 | VIDTLTCGF | 25.85 | 5.14 | 2.93 | 6.00 | 0.95 | 13.90 | 0.45 | 10.00 | 0.11 | 9.49 | 1.11 | 3.26 | 27.24 |
| 180-188 (mod) | VIETLTSGF | **14.61** | 4.84 | 2.55 | 3.66 | 0.82 | 13.07 | 0.71 | 12.96 | 0.35 | 10.37 | 1.38 | 2.39 | 24.04 |
| 131-139 | ADLMGYIPL | **31.05** | 8.06 | 1.93 | 3.35 | 0.61 | 14.51 | 0.73 | 11.40 | 0.13 | 8.30 | 1.01 | 2.08 | 26.33 |
| 131-139 (mod) | AEL[Nle] GYIPL | **16.63** | 7.49 | 3.05 | 3.61 | 0.37 | 20.78 | 1.11 | 14.74 | 0.12 | 10.20 | 0.77 | 1.91 | 72.73 |
| 132-140 | DLMGYIPLV | **16.67** | 103.34 | 4.66 | 5.01 | 1.14 | 25.64 | 4.84 | 22.65 | 0.23 | 7.67 | 1.05 | 2.49 | 39.33 |
| 132-140 (mod) | EL[Nle] GYIPLI | **18.29** | 97.87 | 4.54 | 3.21 | 0.92 | 20.93 | 0.68 | 17.05 | 0.14 | 8.91 | 0.67 | 2.55 | 43.10 |
| 133-141 | LMGYIPLVG | **14.17** | 31.94 | 2.53 | 2.13 | 0.51 | 24.26 | 0.41 | 20.75 | 0.08 | 9.43 | 1.44 | 0.81 | 33.55 |
| 133-141 (mod) | L[Nle] GYIPLIG | **14.33** | 49.48 | 3.98 | 2.48 | 0.71 | 25.94 | 0.89 | 17.29 | 0.15 | 14.60 | 0.73 | 2.85 | 57.46 |
| 134-142 | MGYIPLVGA | **11.34** | 10.71 | 3.40 | 4.79 | 0.35 | 19.54 | 0.80 | 14.88 | 0.73 | 8.85 | 0.83 | 0.85 | 40.78 |
| 134-142 (mod) | [Nle] GYIPLIGA | **17.87** | 10.43 | 3.13 | 7.27 | 1.33 | 27.85 | 1.78 | 21.35 | 0.29 | 11.07 | 1.42 | 5.89 | 60.84 |

TABLE 6-continued

| | HLA-type | A1 | A2 | A3 | A11 | A24 | A29 | B7 | B8 | B14 | B15 | B27 | B35 | B40 |
|---|---|---|---|---|---|---|---|---|---|---|---|---|---|---|
| 135-143 | GYIPLVGAP | **15.62** | 7.28 | 3.46 | 3.84 | 0.80 | 29.74 | 1.37 | 15.94 | 0.47 | 11.02 | 1.76 | 10.35 | 72.32 |
| 135-143 (mod) | GYLPAVGAP | **12.04** | 5.87 | 2.90 | 4.25 | 0.35 | 26.03 | 3.10 | 17.38 | 0.11 | 10.50 | 0.73 | 1.84 | 27.82 |
| 136-144 | YIPLVGAPL | **21.80** | **35.00** | 5.29 | 3.54 | 4.51 | **31.09** | **41.87** | 33.10 | 0.13 | 54.57 | 0.69 | 99.81 | 30.22 |
| 136-144 (mod) | YLPAVGAPI | **15.76** | **75.80** | 2.58 | 3.07 | 4.65 | 28.40 | 7.70 | 17.92 | 0.12 | 49.63 | 0.51 | 2.03 | 64.34 |
| 137-145 | IPLVGAPLG | **13.28** | 4.32 | 2.59 | 2.05 | 0.60 | 26.79 | 2.34 | 17.87 | 0.03 | 10.01 | 0.35 | 30.74 | 41.10 |
| 137-145 (mod) | LPAVGAPIG | **20.57** | 5.60 | 3.02 | 4.95 | 0.61 | 25.32 | 8.12 | 15.87 | 0.12 | 10.10 | 0.49 | 1.06 | 39.31 |
| 147-155 | VARALAHGV | **16.10** | 5.85 | 2.77 | 3.47 | 0.32 | 29.43 | **31.59** | 14.31 | 0.17 | 11.26 | 0.62 | 0.27 | 44.29 |
| 147-155 (mod) | VIRVIAHGL | **18.66** | 8.60 | 4.29 | 4.54 | 0.28 | 27.12 | **29.93** | 32.81 | 0.55 | 9.64 | 1.16 | 2.51 | 52.64 |
| 148-156 | ARALAHGVR | **20.62** | 6.72 | 2.35 | 3.83 | 1.15 | **31.96** | 4.70 | 18.91 | 1.10 | 13.58 | 3.55 | 2.45 | 50.23 |
| 148-156 (mod) | IRVIAHGLR | **15.82** | 4.83 | 3.58 | 2.50 | 0.50 | 23.19 | 3.50 | 13.34 | 0.10 | 8.99 | 9.37 | 0.66 | 26.45 |
| 149-157 | RALAHGVRV | **20.77** | 8.69 | 2.51 | 4.45 | 0.84 | 29.73 | 2.55 | 18.08 | 0.46 | 11.84 | 6.37 | 6.07 | 70.26 |
| 149-157 (mod) | RVIAHGLRL | **11.60** | 18.68 | **13.32** | **17.75** | 0.79 | 23.22 | 102.96 | 12.60 | 0.42 | 106.77 | 15.57 | 1.43 | 24.08 |
| 27-35 | GGQIVGGVY | **13.97** | 6.88 | 3.47 | 2.71 | 1.78 | 20.46 | 3.99 | 14.66 | 0.32 | 110.34 | 0.66 | 0.54 | 30.75 |
| 27-35 (mod) | GGQIIGGNY | **24.04** | 7.06 | 2.23 | 2.40 | 0.39 | 14.38 | 1.09 | 10.52 | 0.25 | 90.62 | 0.24 | 2.22 | 15.03 |
| 28-36 | GQIVGGVYL | **15.07** | **55.85** | 4.80 | 4.46 | 0.50 | 13.73 | 6.56 | 14.53 | 0.37 | 182.45 | 1.01 | 3.24 | 24.20 |
| 28-36 (mod) | GQIIGGNYL | **20.65** | **12.96** | 3.01 | 2.77 | 0.47 | 14.17 | 2.39 | 11.90 | 0.22 | 173.66 | 0.64 | 2.60 | 31.55 |
| 29-37 | QIVGGVYLL | **20.25** | **57.04** | 2.36 | 1.96 | 1.01 | 13.36 | 28.66 | 13.15 | 0.37 | 15.07 | 0.60 | 4.01 | 24.51 |
| 29-37 (mod) | QIIGGNYLI | **21.63** | **73.54** | 6.30 | 4.06 | 12.60 | 13.60 | 52.04 | 10.61 | 0.40 | 29.59 | 0.91 | 8.99 | 83.60 |
| 30-38 | IVGGVYLLP | **22.11** | 6.78 | 1.88 | 3.10 | 0.30 | 12.38 | **24.16** | 11.48 | 1.65 | 15.00 | 0.68 | 2.68 | 19.83 |
| 30-38 (mod) | IIGGNYLIP | **21.14** | 8.27 | 3.88 | 2.81 | 10.95 | 13.88 | **15.47** | 12.18 | 1.17 | 19.93 | 0.97 | 5.35 | 65.43 |
| 31-39 | VGGVYLLPR | **17.88** | 8.73 | 3.41 | 4.16 | 0.34 | 14.20 | 1.15 | 11.57 | 0.44 | 13.22 | 0.79 | 4.02 | 55.61 |
| 31-39 (mod) | IGGNYLIPR | **17.90** | 7.04 | 2.88 | 3.57 | 0.89 | 14.85 | 20.49 | 14.23 | 0.32 | 15.02 | 0.82 | 2.54 | 25.44 |
| 41-49 | GPRLGVRAT | **13.85** | 6.23 | 2.45 | 1.60 | 0.05 | 12.66 | **124.37** | 13.18 | 0.94 | 10.01 | 0.68 | 1.83 | 19.95 |
| 41-49 (mod) | GP[Cit] IGVRAT | **18.60** | 9.16 | 3.48 | 2.72 | 0.16 | 11.88 | 5.38 | 9.99 | 0.13 | 7.29 | 0.59 | 2.25 | 19.61 |
| 42-50 | PRLGVRATR | **17.77** | 6.85 | 3.63 | 2.73 | 0.97 | 13.35 | **42.64** | 11.46 | 0.14 | 10.04 | 0.86 | 1.65 | 14.52 |
| 42-50 (mod) | P[Cit] IGVRAT [Cit] | **18.83** | 7.36 | 2.52 | 1.72 | 0.21 | 14.14 | 1.91 | 9.47 | 0.19 | 12.64 | 0.94 | 2.45 | 49.29 |
| 43-51 | RLGVRATRK | **20.39** | 6.71 | **112.23** | **102.85** | 0.28 | 12.83 | 1.67 | 10.21 | 0.07 | 11.74 | 33.13 | 2.83 | 23.05 |
| 43-51 (mod) | [Cit] IGVRAT [Cit]R | **19.68** | **8.17** | **25.16** | 8.27 | 0.50 | 16.67 | **14.59** | 12.09 | 0.17 | 14.45 | 0.86 | 8.51 | 18.45 |

EXAMPLE 4

Intracellular Staining

Peptides according to the invention with $X^2$ and $X^4$ derived from HCV, Influenza, or CMV were prepared and tested for intracellular staining in an experiment as described above in the “Cell penetration assay”.

| Peptide no. | Antigen | $X^1$ | $X^2$ | $X^3$ | $X^4$ (Different from $X^2$ unless indicated) | $X^5$ | median | n |
|---|---|---|---|---|---|---|---|---|
| 1 | Negative control | | PVVHLTLRQAGDDFSR | | | | 1.00 | 37 |
| 2 | Neg control in scaffold | RRG | PVVHLTL | RRRG | QAGDDFS | | 4.12 | 18 |
| 3 | Positive control | | RQIKIWFQNRRMKWKK | | | | 2.73 | 8 |
| 4 | Positive control (tat) | | YGRKKRRQRRR | | | | 4.43 | 24 |
| 5 | HCV (Native sequence) | | 11 amino acids | G | 11 amino acids | | 1.84 | 18 |
| 6 | HCV | R | 11 amino acids of native seq | RRR | 11 amino acids of native seq | R | 5.35 | 24 |
| 7 | HCV | R | 11 amino acids (1 substitution) | RRR | 11 amino acids (5 substitution) | R | 11.59 | 4 |
| 8 | HCV | RR | 11 amino acids of native seq | RR | 11 amino acids of native seq | | 6.92 | 27 |
| 9 | HCV | RR | 11 amino acids of native seq | RRR | 11 amino acids of native seq | | 3.25 | 21 |
| 10 | HCV (Not scaffold) | EE | 11 amino acids of native seq | EE | 11 amino acids of native seq | | 1.16 | 26 |
| 11 | HCV (Not scaffold) | GG | 11 amino acids of native seq | GG | 11 amino acids of native seq | | 2.01 | 28 |
| 12 | HCV (Native sequence) | | 23 amino acids | | | | 3.01 | 12 |
| 13 | HCV | RR | 13 amino acids | RR | 10 amino acids of native seq | | 21.43 | 8 |
| 14 | HCV | RR | 13 amino acids | RR | 10 amino acids | | 4.81 | 21 |
| 15 | HCV (Not scaffold) | EE | 13 amino acids | EE | 9 amino acids | | 1.16 | 19 |
| 16 | Influenza (Native sequence) | | 23 amino acids | | | | 3.70 | 3 |
| 17 | Flu | BR | 10 amino acids | BRGR | 8 amino acids | | 20.77 | 3 |
| 18 | cmv | R | 9 amino acids | BRR | =$X^2$ | B | 3.86 | 3 |
| 19 | HCV | W | 11 amino acids of native seq | RR | 11 amino acids of native seq | | 17.41 | 13 |
| 20 | HCV | RR | 22 amino acids | RR | 22 amino acids | R | 13.25 | 5 |

Extracellular staining for the same peptides 1-15:

| Peptide no. | Antigen | median | n |
|---|---|---|---|
| 1 | Negative control | 1.00 | 35 |
| 2 | Neg control in scaffold | 1.77 | 20 |
| 3 | Positive control | 9.15 | 19 |
| 5 | HCV Native sequence | 2.08 | 21 |
| 6 | HCV | 2.20 | 29 |
| 7 | HCV | 29.42 | 12 |
| 8 | HCV | 3.06 | 28 |
| 9 | HCV | 2.06 | 23 |
| 10 | HCV (Not scaffold) | 1.95 | 27 |
| 11 | HCV (Not scaffold) | 2.62 | 23 |
| 12 | HCV (Native sequence) | 1.76 | 14 |
| 13 | HCV | 16.80 | 7 |
| 14 | HCV | 17.00 | 16 |
| 15 | HCV (Not scaffold) | 2.38 | 12 |
| 19 | HCV | 1.37 | 19 |
| 20 | HCV | 126.5 | 7 |

Results: It was seen that peptides on scaffold form, compared to native peptides or peptides with other amino acids in X1, X3 and X5 had improved uptake.

The invention claimed is:

1. An isolated cell-penetrating peptide comprising the following structure $$X^1\text{-}X^2\text{-}X^3\text{-}X^4\text{-}X^5 \quad \text{(formula I)},$$

wherein $X^1$ and $X^3$ independently define a linear sequence of any 2 or 3 arginines; $X^2$ and $X^4$ independently define a linear sequence of 8-15 amino acids of a single antigen of HCV, CMV, HPV, or Influenza virus or a variant sequence thereof comprising 1-10 substitutions, additions, or deletions relative to the antigen and sharing at least 50% sequence identity to the corresponding native sequence of said antigen; said sequence $X^4$ being different from $X^2$; and wherein $X^5$ is optionally an arginine or absent; and wherein the sequence of amino acids defined by $X^1$-$X^2$-$X^3$-$X^4$-$X^5$ of formula I does not contain a continuous sequence of four or more arginine residues, which cell-penetrating peptide is of 18-60 amino acids, and wherein the sequence of amino acids defined by $X^1$-$X^2$-$X^3$-$X^4$-$X^5$ of formula I is not found in the native sequence of said antigen.

2. The isolated peptide according to claim 1, wherein, $X^2$ and $X^4$ independently define a linear sequence sharing at least 60% or 70% sequence identity to the native sequence of said antigen.

3. The isolated peptide according to claim 1, wherein the peptide comprises one or more cysteines.

4. The isolated peptide according to claim 1, wherein the N- and/or C-terminal amino acid in $X^2$ is a hydrophilic or polar amino acid.

5. The isolated peptide according to claim 1, wherein the N-terminal amino acid in $X^4$ is a hydrophilic or polar amino acid.

6. The isolated peptide according to claim 1, wherein $X^1$ and/or $X^3$ consists of 2 or 3 arginines.

7. The isolated peptide according to claim 6, wherein $X^1$ consists of RR.

8. The isolated peptide according to claim 6, wherein $X^3$ consists of RR.

9. The isolated peptide according to claim 1, wherein $X^2$ and/or $X^4$ is a linear sequence of 8-12 amino acids.

10. A dimer peptide comprising two peptides monomers, wherein each peptide monomer is as defined in claim 1.

11. A peptide combination comprising two or more peptides according to claim 1.

12. An immunogenic composition comprising at least one peptide according to claim 1 or a dimer peptide comprising two peptide monomers, wherein each peptide monomer comprises an isolated cell-penetrating peptide comprising the following structure $$X^1\text{-}X^2\text{-}X^3\text{-}X^4\text{-}X^5 \quad \text{(formula I)},$$

wherein $X^1$ and $X^3$ independently define a linear sequence of any 2 or 3 arginine's; $X^2$ and $X^4$ independently define a linear sequence of 8-15 amino acids from the same antigen selected from HCV, CMV, HPV, or Influenza virus or a variant sequence thereof comprising 1-10 substitutions, additions or deletions relative to the antigen and sharing at least 50% sequence identity to the native sequence of said antigen; said sequence $X^4$ being different from $X^2$; and wherein $X^5$ is an arginine or absent; which cell-penetrating peptide is of 18-60 amino acids, and wherein the sequence of amino acids defined by $X^1$-X2-X3-$X^4$-$X^5$ of formula I is not found in the native sequence of said antigen; and wherein the sequence of amino acids defined by $X^1$-X2-X3-$X^4$-$X^5$ of formula I does not contain a continuous sequence of four or more arginine residues in combination with a pharmaceutically acceptable diluent or vehicle.

13. The immunogenic composition according to claim 12 in the form of a vaccine composition.

14. The immunogenic composition of claim 12 further comprising an immunological adjuvant.

15. The peptide according to claim 1, wherein $X^5$ is an arginine.

16. The immunogenic composition according to claim 12, wherein $X^5$ is an arginine.

* * * * *